(12) United States Patent
Pogue-Caley et al.

(10) Patent No.: US 8,153,425 B2
(45) Date of Patent: Apr. 10, 2012

(54) DENDRITIC CELL COMPOSITIONS AND METHODS

(75) Inventors: Rebecca Pogue-Caley, Durham, NC (US); Tamara Monesmith, Durham, NC (US); Irina Tcherepanova, Rougemont, NC (US); Lois Dinterman, Kearneysville, WV (US)

(73) Assignee: Argos Therapeutics, Inc., Durham, NC (US)

( * ) Notice: Subject to any disclaimer, the term of this patent is extended or adjusted under 35 U.S.C. 154(b) by 1117 days.

(21) Appl. No.: 11/918,076

(22) PCT Filed: Apr. 7, 2006

(86) PCT No.: PCT/US2006/013159
§ 371 (c)(1),
(2), (4) Date: Oct. 9, 2007

(87) PCT Pub. No.: WO2006/127150
PCT Pub. Date: Nov. 30, 2006

(65) Prior Publication Data
US 2009/0053251 A1    Feb. 26, 2009

(51) Int. Cl.
*C12N 5/0784* (2010.01)
*C12N 5/00* (2006.01)

(52) U.S. Cl. .................................. 435/372; 435/374

(58) Field of Classification Search .................. None
See application file for complete search history.

(56) References Cited

U.S. PATENT DOCUMENTS

2005/0084966 A1    4/2005    Edelson et al.

FOREIGN PATENT DOCUMENTS

| WO | WO 97/29182 | 8/1997 |
|----|-------------|--------|
| WO | WO 98/01538 | 1/1998 |
| WO | WO 02/16560 | 2/2002 |
| WO | WO 03/000907 | 1/2003 |
| WO | WO 03/050271 | 6/2003 |
| WO | WO2004/050855 | 6/2004 |
| WO | WO 2006/031870 | 3/2006 |
| WO | WO 2006/042177 | 4/2006 |

OTHER PUBLICATIONS

Nicolette, C.A. et al., "Dendritic cells for active immunotherapy: Optimizing design and manufacture in order to develop commercially and clinically viable products", Vaccine, 2007, vol. 25S: pp. B47-B60.*

Jonuleit, et al., "Pro-inflammatory cytokines and prostaglandins induce maturation of potent immunostimulatory dendritic cells under fetal calf serum-free conditions" *Eur. J. Immunol.* 1997, 27:3135-3142.

Mohamadzadeh, et al., "Interleukin 15 Skews Monocyte Differentiation into Dendritic Cells with Features of Langerhans Cells" *J. Exp. Med.* vol. 194. No. 7, Oct. 1, 2001 pp. 1013-1019.

Sallusto, et al., "Efficient Presentation of Soluble Antigen by Cultured Human Dendritic Cells is Maintained by Granulocyte/Macrophage Colony-stimulating Factor Plus Interleukin 4 and Downregulated by Tumor Necrosis Factorα" *J. Exp. Med.* vol. 179, Apr. 1994, pp. 1109-1118.

Cella, et al., "Origin, maturation and antigen presenting function of dendritic cells" *Current Opinion in Immunology* 1997, 9:10-16.

Escudier, et al., "Vaccination of metastatic melanoma patients with autologous dendritic cell (DC) derived-exosomes: results of the first phase I clinical trial" *Journal of Translational Medicine* 2005, 3:10.

Morse, et al., "A phase I study of dexosome immunotherapy in patients with advanced non-small cell lung cancer" *Journal of Translational Medicine* 2005, 3:9.

Bender, et al., "Manufacturing Process of a Dendritic Cell Vaccine for Color" POSTER, 8th International Symposium on Dendritic Cells Oct. 17-21, 2004 Brugge, Belgium.

Liu et al., "Adenovirus-medicated CD40 ligan gene engineered denditic cells elicit enhanced CD8+ cytotoxic T-cell activation and antitumjor immunity" *Cancer Gene Ther.* vol. 9, 2002, pp. 202-208.

Koya et al., "Potent maturation of monocyte-derived dendritic cells after CD40L lentiviral gene delivery" *J. Immunother.* vol. 26, No. 5, 2003. pp. 451-460.

Jonuleit, et al., "A Comparison of Two Types of Dendritic Cell as Adjuvants for the Induction of Melanoma-Specific T-Cell Responses in Humans Following Intranodal Injection" *Int. J. Cancer* vol. 93, pp. 243-251 (2001).

Bartels, et al., "Time dependent increase of differential monocyte count on the SYsmex NE-8000" *Clin. Lab. Haem.* vol. 20, pp. 165-168 (1998).

* cited by examiner

*Primary Examiner* — Michael Burkhart
(74) *Attorney, Agent, or Firm* — Elaine T. Sale; Leigh W Thorne

(57) ABSTRACT

Methods are provided for the production of dendritic cells from monocytes that have been incubated at a temperature of 1° C.-34° C. for a period of approximately 6 to 96 hours from the time they are isolated from a subject. After the incubation period, the monocytes can then be induced to differentiate into dendritic cells. Mature dendritic cells made by the methods of the invention have increased levels of one or more of CD80, CD83, CD86, MHC class I molecules, or MHC class II molecules as compared to mature dendritic cells prepared from monocytes that have not been held at 1° C.-34° C. for at least 6 hours from the time they were isolated from a subject. Dendritic cells made by the methods of the invention are useful for the preparation of vaccines and for the stimulation of T cells.

16 Claims, 7 Drawing Sheets

DENDRITIC CELL COMPOSITIONS AND METHODS

FIELD OF THE INVENTION

The present invention relates to methods for the production of dendritic cells and related compositions useful in the treatment of disease.

BACKGROUND OF THE INVENTION

Numerous clinical trials have demonstrated the safety of dendritic cells vaccines, and more that 1000 patients have received dendritic cell vaccines with no serious adverse events associated with the therapy and clinical responses in one half of patients (Ridgeway (2003) Cancer Invest 21:873-876). For example, a recent study showed that vaccination using dendritic cells loaded with four melanoma peptides (gp100, melan-A/MART-1, tyrosine melanoma antigen (MAGE-3), KLH and flu matrix resulted in regression of metastatic melanoma after four bimonthly vaccinations (Banchereau et al. (2001) Cancer Res 61:6451-6458).

A common method for preparing dendritic cells (DCs) is to collect peripheral blood mononuclear cells (PBMCs) from a subject, and then differentiate the monocytes, which are a small proportion of the PBMCs, into DCs. It was widely believed in order to act as suitable precursors for the in vitro manufacture of dendritic cells, monocytes must be either frozen or cultured soon after isolation from a subject. Accordingly, in previous clinical trials where dendritic cell vaccines were made from monocytes, the PBMCs or monocytes were either cultured at approximately 37° C. or frozen within a few hours of the collection of PBMCs from a patient. However, practical manufacturing considerations can limit the widespread use of vaccines processed by a method that requires culturing or freezing freshly isolated PBMCs or monocytes. The differentiation of PBMCs into DCs takes about one week, requires a GMP facility, and skilled technicians. Accordingly, providing facilities and personnel for manufacturing DC vaccines at or near each clinical site where PBMCs are obtained from a patient would likely be cost prohibitive.

A commercially viable model for manufacturing DC vaccines is to provide one or a relatively small number of facilities that can manufacture DC vaccines from patient PBMCs or monocytes collected at a clinical site and then shipped to a manufacturing site. However, such a model cannot be applied to current DC production methods that require fresh PBMCs or monocytes. Freezing fresh monocytes requires additional manipulations at the collection site following leukapheresis, and therefore is not a desirable alternative. Accordingly, there is a need to develop methods for manufacturing DC vaccines using PBMCs or monocytes that have been stored during shipment to a manufacturing facility. The present invention satisfies this need and provides additional advantages as well.

SUMMARY OF THE INVENTION

The inventors have discovered methods which allow the preparation of dendritic cells and dendritic cell vaccines from monocytes which have be stored at 1-34° C. for time periods of 6-96 hours following isolation from a subject. The ability to manufacture DCs from stored monocytes allows greater flexibility and shipment of the monocytes from the site of collection to a manufacturing facility. In addition, the inventors have found that the dendritic cell vaccines manufactured from stored monocytes are phenotypically superior to dendritic cells manufactured from fresh monocytes. For example, the dendritic cell vaccines manufactured from stored monocytes have increased levels of costimulatory molecules, such as CD80, CD83 and CD86, as well as higher levels of MHC class I and MHC class II molecules as compared to dendritic cells manufactured from fresh monocytes.

Thus, in one aspect, the invention provides a method for producing dendritic cells from monocytes, comprising:
  a. providing monocytes that have been incubated at a temperature of 1° C.-34° C. for a period of 6 to 96 hours from the time they are isolated from a subject; and
  b. inducing the differentiation of said monocytes into dendritic cells.

In a preferred embodiment, the monocytes are obtained by leukapheresis to collect peripheral blood mononuclear cells (PBMCs) that comprise monocytes.

Preferably, differentiation is induced by contacting the monocytes with a culture medium comprising an effective amount of a composition that induces the differentiation of monocytes into immature dendritic cells, such as, but not limited to, GM-CSF; GM-CSF and IL-4: GM-CSF and IL-13; GM-CSF and IL-15; and IFNα. The immature dendritic cells can then be matured to produce mature dendritic cells.

The mature dendritic cells manufactured by the methods of the invention are phenotypically different than prior art mature dendritic cells. For example, the invention provides mature monocyte derived dendritic cell, wherein the steady state ratio of ALOX15 RNA to actin RNA or GAPDH RNA in the cell is less than 1.0. This is a decreased ratio as compared to the ratio of ALOX15 to Actin or GAPDH RNA in mature dendritic cells prepared from fresh monocytes. In another embodiment, the invention provides a mature monocyte derived dendritic cell, wherein the steady state ratio of CD52 RNA to actin RNA or GAPDH in the cell is greater than 1.0. In yet another embodiment, the invention provides a mature monocyte derived dendritic cell, wherein the steady state ratio of TLR1 RNA, TLR2 RNA, IL-1β RNA or CD69 RNA to actin RNA or GAPDH RNA in the cell is less than 1.0.

In still another embodiment, the invention provides a composition comprising mature monocyte derived dendritic cells, wherein the mature dendritic cells have increased levels of one or more of CD80, CD83, CD86, MHC class I molecules, or MHC class II molecules as compared to mature dendritic cells prepared from fresh monocytes. In addition, the invention provides mature monocyte derived dendritic cells having altered steady state levels of ALOX15 RNA, CD52 RNA, TLR1 RNA, TLR2 RNA, IL-1β RNA or CD69 RNA.

The dendritic cells prepared by the methods of the invention are particularly useful for preparing vaccines. Thus, related dendritic cell compositions and vaccines are provided as well. In a preferred embodiment, the vaccine is autologous to the subject. Preferably, the dendritic cell vaccine is loaded with antigen from a cancer cell or pathogen present in the subject.

Surprisingly, the inventors have found that dendritic cell vaccines frozen with DMSO are stable in the presence of DMSO for at least two hours after thawing. Accordingly, the invention provides the use of an antigen-loaded dendritic cell for the preparation of a frozen medicament for the treatment or prevention of cancer or pathogen infection, wherein the medicament comprises at least 2% DMSO and is ready for administration upon thawing. In another embodiment, the invention provides a method of vaccinating a subject, comprising:
  a. thawing a frozen dendritic cell vaccine comprising at least 2% DMSO, and b. administering the thawed vaccine to the subject without altering the ratio of cells to DMSO prior to administration.

Preferably the concentration of DMSO is approximately 10%.

In another embodiment, the invention provides an antigen-loaded dendritic cell, wherein said cell is differentiated in vitro from a monocyte and is capable of surviving in vitro for at least 24 hours following freezing in the presence of ≧5% DMSO and thawing. In a preferred embodiment, the antigen loaded dendritic cell is capable of surviving in vitro for at least 24 hours following freezing in the presence of ≧10% DMSO and thawing.

In another embodiment, the invention provides a dendritic cell vaccine, comprising approximately 5-15% DMSO, wherein said vaccine is ready for administration to a subject.

DETAILED DESCRIPTION OF THE INVENTION

Figure 1:
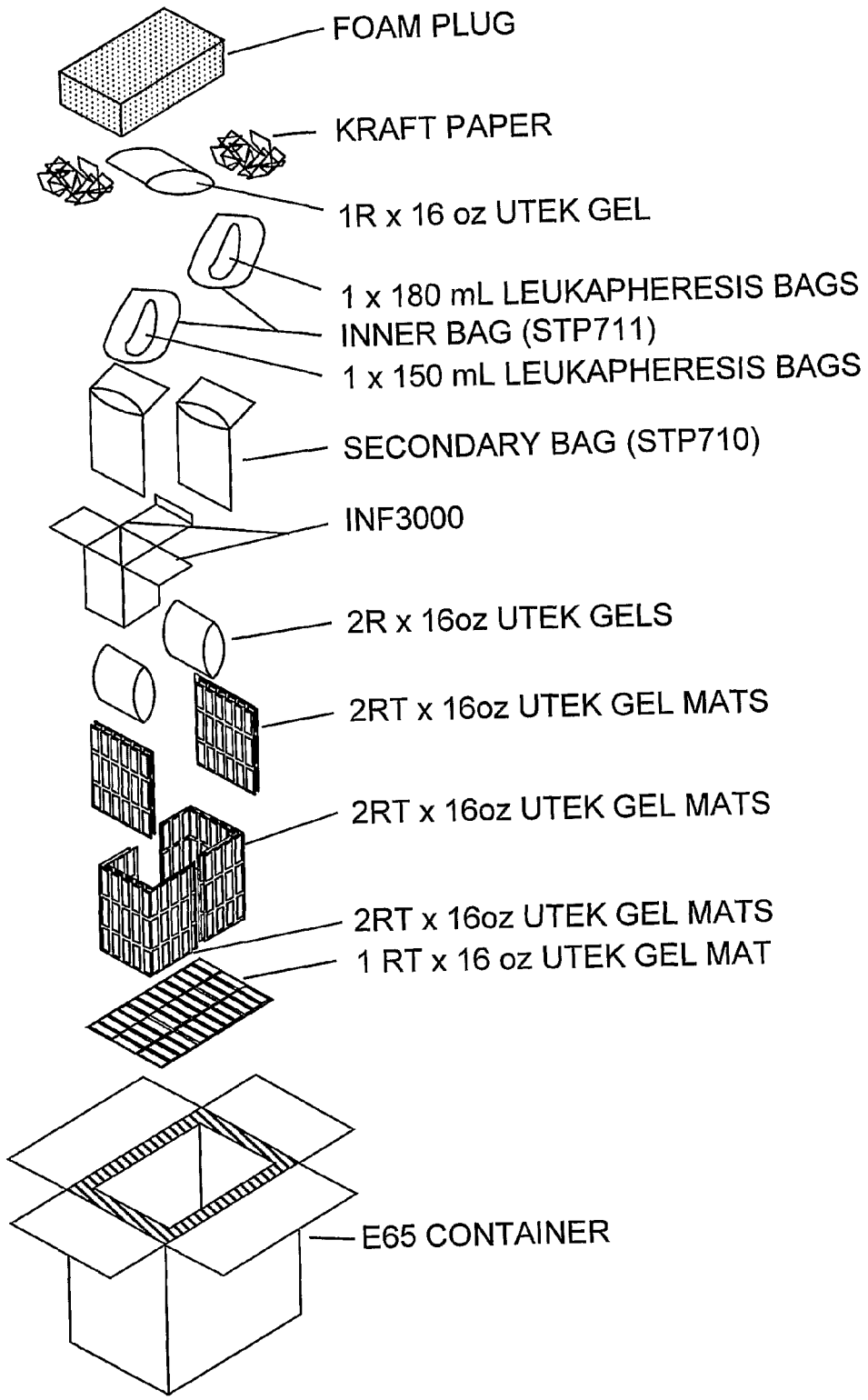
FIG. 1: Diagram of a preferred shipping container and packaging materials for the temperature controlled shipping of monocytes (e.g, leukapheresis product).

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. See, e.g., Sambrook et al. Molecular Cloning: A Laboratory Manual, $2^{nd}$ edition (1989); Current Protocols in Molecular Biology (F. M. Ausubel et al. eds. (1987)); the series Methods in Enzymology (Academic Press, Inc.); PCR: A Practical Approach (M. MacPherson et al. IRL Press at Oxford University Press (1991)); PCR 2: A Practical Approach (M. J. MacPherson, B. D. Hames and G. R. Taylor eds. (1995)); Antibodies, A Laboratory Manual (Harlow and Lane eds. (1988)); Using Antibodies, A Laboratory Manual (Harlow and Lane eds. (1999)); and Animal Cell Culture (R. I. Freshney ed. (1987)).

DEFINITIONS

As used herein, certain terms may have the following defined meanings.

As used in the specification and claims, the singular form "a," "an" and "the" include plural references unless the context clearly dictates otherwise. For example, the term "a cell" includes a plurality of cells, including mixtures thereof.

The term "antigen" is well understood in the art and includes substances which are immunogenic, i.e., immunogens, as well as antigenic epitopes. It will be appreciated that the use of any antigen is envisioned for use in the present invention and thus includes, but is not limited to, a self-antigen (whether normal or disease-related), an infectious antigen (e.g., a microbial antigen, viral antigen, etc.), or some other foreign antigen (e.g., a food component, pollen, etc.). The term "antigen" or alternatively, "immunogen" applies to collections of more than one immunogen, so that immune responses to multiple immunogens may be modulated simultaneously. Moreover, the term includes any of a variety of different formulations of immunogen or antigen. In preferred embodiments, the antigen is from a cancer cell or a pathogen. Preferably, the cancer cell is a renal cancer cell, a multiple myeloma cell or a melanoma cell. Preferred pathogens are HIV and HCV. In preferred embodiments, the antigen is delivered to the antigen presenting cell (APC) in the form of RNA isolated or derived from a cancer cell or a pathogen. "Derived from" includes, but is not limited recombinant variants of naturally occurring sequences, including fusions to unrelated or related sequences. Methods for RT-PCR of RNA extracted from any cell (e.g., a cancer cell or pathogen cell), and in vitro transcription are disclosed in copending U.S. provisional patent application No. 60/525,076, and PCT/US05/053271, the contents of which are incorporated by reference.

By "cancer" is meant the abnormal presence of cells which exhibit relatively autonomous growth, so that a cancer cell exhibits an aberrant growth phenotype characterized by a significant loss of cell proliferation control. Cancerous cells can be benign or malignant. In various embodiments, the cancer affects cells of the bladder, blood, brain, breast, colon, digestive tract, lung, ovaries, pancreas, prostate gland, or skin. The definition of a cancer cell, as used herein, includes not only a primary cancer cell, but also any cell derived from a cancer cell. This includes metastasized cancer cells, and in vitro cultures and cell lines derived from cancer cells. Cancer includes, but is not limited to, solid tumors, liquid tumors, hematologic malignancies, renal cell cancer, melanoma, breast cancer, prostate cancer, testicular cancer, bladder cancer, ovarian cancer, cervical cancer, stomach cancer, esophageal cancer, pancreatic cancer, lung cancer, neuroblastoma, glioblastoma, retinoblastoma, leukemias, myelomas, lymphomas, hepatoma, adenomas, sarcomas, carcinomas, blastomas, etc.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the term "cytokine" refers to any one of the numerous factors that exert a variety of effects on cells, for example, inducing growth or proliferation. Non-limiting examples of cytokines which may be used alone or in combination in the practice of the present invention include, interleukin-2 (IL-2), stem cell factor (SCF), interleukin-3 (IL-3), interleukin-4 (IL-4), interleukin-6 (IL-6), interleukin-11 (IL-11), interleukin-12 (IL-12), interleukin-13 (IL-13), interleukin-15 (IL-15), granulocyte-colony stimulating factor (G-CSF), granulocyte macrophage-colony stimulating factor (GM-CSF), interleukin-1 beta (IL-1β), interferon-γ (IFNγ), tumor necrosis factor-α (TNFα), prostaglandin $E_2$ (PGE$_2$), MIP-11, leukemia inhibitory factor (LIF), c-kit ligand, thrombopoietin (TPO) and flt3 ligand. Cytokines are commercially available from several vendors such as, for example, Genzyme (Framingham, Mass.), Genentech (South San Francisco, Calif.), Amgen (Thousand Oaks, Calif.), R&D Systems (Minneapolis, Minn.) and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the invention.

The term "dendritic cells (DCs)" refers to a diverse population of morphologically similar cell types found in a variety of lymphoid and non-lymphoid tissues, Steinman (1991) Ann. Rev. Immunol. 9:271-296. Dendritic cells constitute the most potent and preferred APCs in the organism. Dendritic cells can be differentiated from monocytes, and possess a distinct phenotype from monocytes. For example, a particular differentiating marker, CD14 antigen, is not found in dendritic cells but is possessed by monocytes. It has been shown that mature DCs can provide all the signals necessary for T cell activation and proliferation. Also, mature dendritic cells are not phagocytic, whereas the monocytes and immature dendritic cells are strongly phagocytosing cells. Immature DCs are capable of capturing antigens by endocytosis, phagocytosis, macropinocytosis or adsorptive pinocytosis and receptor mediated antigen uptake, and are phenotypically $CD80^-$ or $CD80^{low}$, $CD83^-$ or $CD83^{low}$, $CD86^{low}$, and have high intracellular concentrations of MHC class II molecules. Mature DCs have a veiled morphology, a lower capacity for endocytosis and are phenotypically $CD80^{high}$, $CD83^{high}$, $CD86^{high}$ in comparison to immature DCs. Preferably, the mature DCs secrete IL-12 p70 polypeptide or protein, and/or secrete significantly reduced levels (0 to 500 pg/ml per million DCs) of IL-10. IL-10 and IL-12 levels can be determined by ELISA of culture supernatants collected at up to 36 hrs post induction of DC maturation from immature DCs. Wierda W. G. et al (2000) Blood 96: 2917. Ajdary S et al (2000) Infection and Immunity 68: 1760. See Banchereau and Steinman (1998) Nature 392:245 for a review.

An "effective amount" is an amount sufficient to effect beneficial or desired results. An effective amount can be administered in one or more administrations, applications or dosages.

As used herein, "expression" refers to the processes by which polynucleotides are transcribed into mRNA and/or mRNA is translated into peptides, polypeptides, or proteins. If the polynucleotide is derived from genomic DNA of an appropriate eukaryotic host, expression may include splicing of the mRNA. Regulatory elements required for expression include promoter sequences to bind RNA polymerase and transcription initiation sequences for ribosome binding. For example, a bacterial expression vector or cassette includes a promoter (e.g., lac promoter) and for transcription initiation the Shine-Dalgarno sequence and the start codon AUG (Sambrook et al. (1989) supra). Similarly, a eukaryotic expression vector or cassette typically includes a heterologous or homologous promoter for RNA polymerase II, a Kozak sequence, the start codon AUG, a termination codon for detachment of the ribosome and a downstream polyadenylation signal. Such vectors can be obtained commercially or assembled by the sequences described in methods known in the art.

The term "genetically modified" means containing and/or expressing a foreign gene or nucleic acid sequence which in turn, modifies the genotype or phenotype of the cell or its progeny. In other words, it refers to any addition, deletion or disruption to a cell's endogenous nucleotides.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated", "separated" or "diluted" polynucleotide, peptide, polypeptide, protein, antibody, or fragment(s) thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragment(s) thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as its glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature. An isolated mammalian cell is separated from where it is normally found in the body, or is removed from the body. For example, leukocytes collected by leukopheresis are "isolated", and dendritic cells differentiated from monocytes in vitro are "isolated".

The terms "major histocompatibility complex" or "MHC" refers to a complex of genes encoding cell-surface molecules that are required for antigen presentation to T cells and for rapid graft rejection. In humans, the MHC is also known as the "human leukocyte antigen" or "HLA" complex. The proteins encoded by the MHC are known as "MHC molecules" and are classified into Class I and Class II MHC molecules. Class I MHC molecules include membrane heterodimeric proteins made up of an α chain encoded in the MHC noncovalently linked with the β2-microglobulin. Class I MHC molecules are expressed by nearly all nucleated cells and have been shown to function in antigen presentation to $CD8^+$ T cells. Class I molecules include HLA-A, B, and C in humans. Class II MHC molecules also include membrane heterodimeric proteins consisting of noncovalently associated α and β chains. Class II MHC molecules are known to function in $CD4^+$ T cells and, in humans, include HLA-DP, DQ, and DR.

By monocytes is meant $CD14^+$ peripheral blood mononuclear cells capable of differentiating into immature dendritic cells in response to GM-CSF and IL-4.

"Pathogen", as used herein, refers to any disease causing organism or virus, and also to attenuated derivatives thereof.

A "pharmaceutical composition" is intended to include the combination of an active agent (such as an antigen-loaded DC) with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as heat-inactivated serum plus 10% DMSO plus 5% dextrose, phosphate buffered saline solution, water, and emulsions, such as an oil/water or water/oil emulsion, and various types of wetting agents. The compositions also can include adjuvants, stabilizers and preservatives. For examples of carriers, stabilizers and adjuvants, see Remington's Pharm. Sci. 18$^{th}$ Ed. (Mack Publ. Co., Easton (1990)).

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In addition to a native nucleic acid molecule, a nucleic acid molecule of the present invention may also comprise modified nucleic acid molecules.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

As used herein "subject" refers to a mammal, including, but not limited to, humans and other primates, rodents, dogs and cats. Preferably, the subject is a human.

The inventors have discovered that immature dendritic cells, mature dendritic cells and antigen loaded dendritic cells can be produced from monocytes stored at 1° C.-34° C. for approximately 6 to 96 hours following collection of the monocytes from a patient. These results are surprising, as it was commonly believed critical to prepare dendritic cells from freshly isolated monocytes, rather than from monocytes that had been stored at ambient temperatures for a significant length of time. Moreover, monocyte-derived DC vaccines used in clinical trials performed prior to the instant invention have been prepared by culturing monocytes within less than 6 hours following collection from a patient, or by freezing PBMCs shortly after collection, and storing the PBMCs for subsequent thawing and culturing of monocytes.

Not only have the inventors found that it is possible to make dendritic cells and dendritic cell vaccines from monocytes that have been stored at 1° C.-34° C. for approximately 6 to 96 hours, they have also surprisingly discovered that dendritic cells made by this method are phenotypically superior to the dendritic cells made from fresh monocytes. The method of manufacture and the characteristics of dendritic cell vaccines produced by these methods are particularly relevant to vaccine potency, successful commercialization over a widespread area, and ease of administration. First, the mature dendritic cells manufactured using the methods of the invention, when compared to DCs produced by prior art methods, express increased levels CD80, CD83 and CD86 costimulatory molecules, as well as increased levels of MHC class I and MHC class II molecules, all of which are indicative of DC maturity and potency. In addition, mature DCs of the invention are able to induce IL-2 production from memory T cells in an antigen specific fashion.

Second, it would not be commercially feasible to establish dendritic cell manufacturing capabilities nearby each site where patient PBMCs will be collected. Therefore, successful widespread commercialization of an autologous dendritic cell vaccine will depend on the ability to ship PBMCs, or monocytes isolated from PBMCs to centralized manufacturing facilities for differentiation into immature and mature dendritic cells and preparation of vaccines. However, prior to the instant invention, it was widely thought that PBMCs must be frozen or cultured shortly after removal from a patient. The methods of the invention solve this problem by allowing the processing of PBMCs or monocytes isolated from PBMCs which have been shipped by overnight or longer delivery.

Third, antigen-loaded dendritic cells are typically frozen in DMSO and stored until thawing, washing and resuspending in a DMSO-free pharmaceutically acceptable carrier prior to administration to a patient. The washing step was included in prior DC vaccine clinical trials because it was thought that DMSO has detrimental effects on unfrozen or thawed DCs. Surprisingly, the inventors have discovered that DMSO has no noticeable detrimental effect on dendritic cells. Thus, there is no need to wash and resuspend the thawed DC vaccine prior to administration. Omitting this step increases the ease of administration and decreases both the risk of contamination and of adverse effects to the DCs due to additional manipulations.

Accordingly, in one aspect, the invention provides a method for producing dendritic cells from monocytes, comprising:

a. providing monocytes that have been incubated at a temperature of 1° C.-34° C. for a period of approximately 6 to 96 hours from the time they are removed from a subject; and b. inducing the differentiation of the incubated monocytes into dendritic cells.

As used herein, "monocyte" refers to a $CD14^+$ leukocyte having the capacity to differentiate into a dendritic cell. The monocyte may be from any mammal, and preferably is a human monocyte. The monocytes can be provided and incubated in compositions such as, but not limited to, blood, blood fractions (e.g., white blood cells (WBCs), buffy coats, peripheral blood mononuclear cells (PBMCs), etc, and as well as in compositions further enriched for monocytes. In a preferred embodiment, the monocytes are provided together with other peripheral blood mononuclear cells (PBMCs), for example, as a leukapheresis product. In another embodiment, the monocytes are enriched from PBMCs, or isolated directly from peripheral blood. Methods of isolating monocytes or PBMCs containing monocytes are known to those of skill in the art. In preferred embodiments, the monocytes are collected together with other PBMCs by leukapheresis. Methods of leukapheresis are known in the art. In a preferred embodiment of the invention, PBMCs comprising monocytes are collected from a subject by leukapheresis at a hospital, clinic, doctor's office, etc. Leukapheresis is a procedure by which the white blood cells are removed from a subject's blood, the remainder of which is then transfused back into the subject. The leukapheresis product is typically a blood fraction enriched for PBMCs, with low levels of contaminating red blood cells, granulocytes and platelets. Methods and equipment for performing leukapheresis are well known in the art. See, for example gambrobct.com/Products_&_Services/ for detailed information on leukapheresis. Examples of leukapheresis apparatuses include the COBESpectra™ manufactured by GAMBRO BCT, and the CS3000 Plus Blood Cell Separator manufactured by Baxter Fenwal.

Monocytes can be enriched from blood or blood fractions (e.g., PBMCs), during or after the 1° C.-34° C. incubation period. As used herein, "enriching monocytes" means a method which increases the proportion of monocytes with respect to other cell types that were present at the start of the method. Methods for enriching monocytes from PBMCs, blood or other blood fractions are known to those of skill in the art and include, but are not limited to elutriation, FACS, panning, magnetic sorting, low density Ficoll gradient centrifugation, and the like. Preferably, monocytes are enriched from PBMCs by elutriation. In one alternative embodiment, monocytes are enriched from PBMCs following the 6-96 hour incubation period by selection for monocytes which adhere to plastic during cell culture. In another embodiment, monocytes are enriched by immunomagnetic selection. The immunomagnetic selection may be positive selection to bind monocytes, or may be negative selection, to bind cells which are not monocytes (e.g., T cells, B cells, etc.)

Once isolated from a subject, monocytes (e.g., purified monocytes, enriched monocytes, PBMCs comprising monocytes, etc.) are incubated at a temperature of 1° C.-34° C. for a period of approximately 6 to 96 hours from the time they are isolated from a subject. As used herein, the time at which monocytes or PBMCs containing monocytes are isolated from a subject refers to the time at the completion of the process of removing the cells from the subject. For example, where PBMCs are isolated from a patient over the course of a four hour leukapheresis procedure, the time of isolation would be the time at which collection of PBMCs by leukapheresis ends.

Preferably, the monocytes are incubated for 6 to 96 hours at a temperature of 3° C.-34° C., or 4° C.-32° C. or 5° C.-30° C., more preferably at a temperature of 6° C.-28° C., even more preferably at a temperature of 6° C.-27° C., 8° C.-26° C. or about 14° C.-24° C. Preferred lower temperature ranges are 6° C., 7° C., 8° C., 9° C., 10° C., 11° C., 12° C., 13° C. and 14° C. Preferred upper temperature ranges are 20° C., 21° C., 22° C., 23° C., 24° C., 25° C., 26° C., 27° C., 28° C., 29° C., 30° C., 31° C., 32° C., 33° C. and 34° C. Preferably, the period of incubation is 8 to 72 hours, more preferably 10 to 48 hours, even more preferably 12 to 24 hours, and most preferably, 15 to 22 hours. Other preferred ranges of incubation times include 8 to 48 hours, 10 to 30 hours, 26 to 72 hours and 48 to 80 hours. Preferred lower limits of incubation times can be selected from 6, 7, 8, 10, 12, 14, 16, 20, 22, 24, 26, 28, 30, 36 and 48 hours. Preferred upper limits of incubation times can be selected from 24, 26, 28, 30, 36, 48, 60, 72, 84 and 96 hours.

Monocytes in any form (e.g., monocytes in blood, blood fractions, PBMCs, purified monocytes, etc.) may be shipped from a clinical site to a dendritic cell manufacturing site during the 1° C.-34° C. incubation period. Preferably, the monocytes are shipped in a temperature controlled container. Methods of maintaining the temperature of the monocytes between 1° C.-34° C. during the incubation period are known to those of skill in the art. For example, the monocytes can be incubated in an incubator or a room at 1° C.-34° C. Preferably, the monocytes are subjected to some motion (either occasional or continuous) during the incubation period. The motion can be the motion associated with shipping. In another embodiment, the cells can be gently rocked or rotated during incubation. While not wishing to be bound by theory, it is thought that the motion may prevent cell damage associated with compaction during settling.

During the 6-96 hour incubation period at 1° C.-34° C., the monocytes are incubated without culturing. By "without culturing", is meant that during the 6 to 96 hour incubation period, the monocytes are not cultured in a mammalian cell culture medium (including, but not limited to, physiologically appropriate concentrations (e.g., about 1x) of culture mediums such as RPMI, DMEM, X-VIVO 15, AIM-V, StemSpan H2000, and the like) at a temperature of about 36-38° C. Rather, monocytes processed by the methods of the invention are incubated at 1° C.-34° C., preferably in blood or blood fractions (e.g., serum, plasma, leukapheresis product (e.g., PBMCs), buffy coat, etc.) saline or biological buffers such as phosphate buffer saline (PBS). Most preferably, the leukapheresis product containing monocytes is incubated at 1° C.-34° C. in the leukapheresis collection container (e.g., a blood collection bag). While the leukapheresis product may be transferred to another container at the beginning or during the incubation period, it is preferable to avoid unnecessary transfers, which could increase the likelihood of contamination.

During or after the 6-96 hour incubation at 1° C.-34° C., the monocytes can be enriched prior to differentiation step. Manipulations may be performed on the monocytes or PBMCs, etc., during the period of incubation, so long as the manipulations are performed at 1° C.-34° C. In particular, PBMCs may be further purified, or monocytes may be enriched from PBMCs during this period of incubation. Such manipulations include, but are not limited to, centrifugation, elutriation, tangential flow filtration, Ficoll density gradient, dilute Ficoll density gradient centrifugation, dilute Percoll density gradient centrifugation, antibody panning, magnetic cell sorting, positive or negative immunomagnetic selection, and the like. In one embodiment, monocytes can be enriched from PBMCs after the incubation period by culture in a container (preferably a plastic container) and selection for adherent monocytes.

Following incubation at a temperature of 1° C.-34° C. for a period of approximately 6 to 96 hours, and an optional step of further enrichment of the monocytes, the monocytes are induced to differentiate into dendritic cells. Typically, monocytes are differentiated into immature dendritic cells and then the immature dendritic cells then can be matured into mature dendritic cells. A variety of methods for differentiating monocytes into dendritic cells, and for maturing the dendritic cells are known to those of skill in the art.

In one embodiment, monocytes are cultured in a medium comprising a composition that induces the differentiation of monocytes into immature or mature dendritic cells. Compositions which induce the differentiation of monocytes into immature dendritic cells are known to those of skill in the art. Such compositions include, but are not limited to, GM-CSF+ IL-4; GM-CSF+IL-13; GM-CSF+IL-15; IFN$\alpha$; and GM-CSF+TNF$\alpha$. Preferably the composition which induces differentiation is GM-CSF+IL-4. The concentrations of GM-CSF and IL-4 may range from about 400 to 2000 U/ml of each cytokine. Preferably, the concentration of GM-CSF and IL-4 is 500 to 1000 units/ml of each cytokine. In one embodiment, the monocytes are contacted with GM-CSF and IL-4 for about 4-7 days, most preferably for about 5-6 days, during which time the monocytes differentiate into immature dendritic cells.

Following differentiation of monocytes into immature dendritic cells, the immature dendritic cells can be matured into mature dendritic cells. Methods for maturing dendritic cells are known to those of skill in the art. In one embodiment, the immature dendritic cell are matured by contact with a medium comprising GM-CSF, IL-4 and a maturation cocktail (PGE$_2$, TNF$\alpha$, IL-6 and IL-1$\beta$). See for example, Jonuliet et al. (1997) Eur J Immunol 27:3135-3142, the contents of which are incorporated by reference.

In an alternative maturation method, immature dendritic cells are signaled with a first signal, comprising IFN-$\gamma$, followed by a second signal comprising CD40L. For example, in one embodiment, immature dendritic cells are contacted with PGE$_2$, IFN-$\gamma$ and CD40L, preferably in the presence of GM-CSF and IL-4. In a preferred embodiment, the contacting with CD40L is effected upon translation of a recombinant CD40L mRNA within the dendritic cells. Preferably, the dendritic cell is transiently transfected with an mRNA encoding CD40L or an active fragment thereof.

Most preferably, immature dendritic cells are contacted with PGE$_2$, TNF$\alpha$, and IFN$\gamma$, preferably in the presence of GM-CSF and IL-4, to produce mature dendritic cells. The maturity of the dendritic cells can be further increased by transfection, preferably transient transfection, with an RNA encoding CD40L. Preferably, the dendritic cells are transfected with an RNA encoding CD40L and/or RNA encoding one or more antigens or epitopes of interest. The above maturation methods are described in U.S. application Ser. No. 11/246,387 the contents of which are incorporated by reference.

In preferred embodiments of the invention, the dendritic cells are loaded with one or more antigens. Antigen loaded dendritic cells are useful as vaccines and for the in vitro stimulation of T cells. Antigens can be loaded into immature or mature dendritic cells. If antigens are loaded into immature dendritic cells, the immature dendritic cells can then be matured by the process of loading itself, or by other maturation methods described herein or alternative maturation methods known to those of skill in the art. The antigen(s) can be loaded as the antigen itself (e.g., proteins, peptides, epitopes, cell lysates, viral particles, etc.) or can be loaded as a nucleic acid(s) encoding antigen(s). Preferably, the antigen is loaded as a nucleic acid encoding the antigen. More preferably, the nucleic acid is an RNA, most preferably an mRNA. In a preferred embodiment mRNA encoding one or more antigens is cotransfected with mRNA encoding CD40L. Preferably, the antigen is autologous to the subject, and is used to prepare an antigen loaded autologous DC vaccine for administration to the subject. Methods for loading dendritic cells with peptide and protein antigens, cells, cell or tissue lysates, viruses or viral particles, nucleic acids and the like are known to those of skill in the art.

In a preferred embodiment, the antigen is loaded by electroporation of a dendritic cell (mature or immature) with a nucleic acid, preferably an mRNA. Preferably, the dendritic cells are transfected with approximately 0.25 to 4 micrograms RNA per 106 dendritic cells, most preferably with about 2 µg RNA per $10^6$ dendritic cells. In one embodiment, 1 microgram tumor RNA per million DC is used per transfection. In another embodiment, 0.25 to 1.0 µg each of four RNAs encoding four separate antigens from a pathogen (e.g., HIV) is used per $10^6$ dendritic cells.

The antigen can be from any source. However, in preferred embodiments, the antigen or antigen(s) are autologous to the subject. By autologous to the subject is meant that the antigen is obtained or derived from the subject. As non-limiting examples, the antigens may be from cancer cells or tumor tissue obtained from a subject. The cancer antigens could be loaded into dendritic cells as cancer cells, cancer cell or tissue lysates, extracts from cancer cells or tissues, purified or cloned components of cancer cells or tissues, total RNA or total mRNA, or selected RNA or mRNA from such cells or tissues, whether present in extracts, purified, amplified, in vitro translated and the like. Alternatively, the antigen may be obtained or derived from a pathogen or pathogen-infected cells present in a subject.

The methods of the invention are particularly useful for the treatment or prevention of cancer and pathogen infection. In preferred embodiments, the cancer is renal cell carcinoma, melanoma, breast cancer, chronic lymphocytic leukemia, multiple myeloma, lung cancer, colon cancer, pancreatic cancer, stomach cancer or prostate cancer.

The term pathogen refers to any virus or organism which is involved in the etiology of a disease and also to attenuated derivatives thereof. Such pathogens include, but are not limited to, bacterial, protozoan, fungal and viral pathogens such as *Helicobacter*, such as *Helicobacter pylori, Salmonella, Shigella, Enterobacter, Campylobacter*, various mycobacteria, such as *Mycobacterium leprae, Bacillus anthracis, Yersinia pestis, Francisella tularensis, Brucella* species, *Lep-* tospira interrogans, Staphyloccus, (e.g., *S. aureus*), Streptococcus, Clostridum, Candida albicans, Plasmodium, Leishmania, Trypanosoma, human immunodeficiency virus (HIV), hepatitis C virus (HCV), human papilloma virus (HPV), cytomegalovirus (CMV), human T-lymphotrophic virus (HTLV), herpesvirus (e.g., herpes simplex virus type 1, herpes simplex virus type 2, coronavirus, varicella-zoster virus, and Epstein-Barr virus (EBV)), papilloma virus, influenza virus, hepatitis B virus, poliomyelitis virus, measles virus, mumps virus, and rubella virus. Preferably the pathogen is a viral pathogen, more preferably a retroviral pathogen, and most preferably HIV or HCV.

Dendritic cells, whether mature or immature, antigen loaded or not, can be frozen in a composition comprising a cryoprotectant. Numerous cryoprotectants are known to those of skill in the art. Examples of cyroprotectants include, but are not limited to, dimtheylsulfoxide (DMSO), glycerol, ethanol, methanol, acetamide, glycerol monoacetate, propane-diol, polyethylene glycol, ethylene glycol, i-erythritol, D-ribitol, D-mannitol, D-sorbitol, D-lactose, i-inositol, choline chloride, amino acids, albumin (preferably human serum albumin), polyvinyl pyrrolidone, dextran, sucrose, Ficoll, inorganic salts, and hydroxyethyl starch. In a preferred embodiment, the cyroprotectant is DMSO. Preferably, the concentration of DMSO is 2-20%, more preferably 5-15%, and most preferably approximately 10%. Also, the freezing medium may contain one or more polyol compounds derived from carbohydrates, such as glucose, dextrose, sucrose, etc., preferably in a concentration of from 2-30%, more preferably from 5-10%, most preferably 5% dextrose. Methods for freezing dendritic cells are known to those of skill in the art. See, for example U.S. patent application 20040253574, the contents of which are incorporated by reference. Preferably, the cryoprotectant is dimethylsulfoxide (DMSO). In preferred embodiments, the concentration of DMSO is 5% to 20%. Most preferably, the concentration of DMSO in the composition is approximately 10%.

Surprisingly, dendritic cells and dendritic cell vaccines made by the methods of the invention are capable of surviving in vitro for at least 24 hours post-thaw following freezing in the presence of 5%-20% DMSO and thawing. Because the antigen-loaded dendritic cells of the invention are resistant to DMSO, it is not necessary to wash the cell prior to administering the dendritic cell vaccine. Accordingly, the thawed dendritic cell vaccines of the invention are ready for administration to a subject at any time after thawing. Eliminating the washing step reduces the risk of contamination and avoids further manipulations that may damage the dendritic cells. Thus, in one embodiment, the invention provides a method for the administration of an antigen loaded dendritic cell vaccine, comprising thawing a frozen dendritic cell vaccine comprising at least 2% to 20% DMSO, and administering the vaccine to a subject without altering the ratio of dendritic cells to DMSO prior to administration. Preferably, the concentration of DMSO in the vaccine is approximately 5-20%, and more preferably 10%.

In another embodiment, the invention provides the use of an antigen-loaded dendritic cell for the preparation of a frozen medicament for the treatment or prevention of cancer or pathogen infection, wherein the medicament comprises at least 2% DMSO and is ready for administration upon thawing.

The methods of the invention allow the production of novel dendritic cells with increased functionality and increased levels of maturity markers. For example, in one aspect the invention provides mature monocyte derived dendritic cells, wherein the mature dendritic cells have increased levels of one or more of CD80, CD83, CD86, MHC class I molecules, or MHC class II molecules as compared to mature dendritic cells prepared from fresh monocytes.

In yet another embodiment, the invention provides a mature monocyte derived dendritic cell, wherein the dendritic cell can elicit antigen-specific IL-2 production from a memory T cell. Methods for measuring IL-2 are known in the art. Cell surface markers and expression of other molecules which are characteristic of memory T cells, and which distinguish them from other types of T cells, are disclosed in FIG. 10.35 of Immunobiology, $6^{th}$ Edition, Eds. Janeway et al., Garland Science Publishing, New York, N.Y., 2005; the content of which is incorporated by reference. For example, memory T cells express high levels of CD44, CD45RO, CD45RA, Bcl-2, IFNγ, CD127 and Ly6C; moderate levels of CD122, and CXCR4; low levels of FasL, and are CD69 and CD25 negative.

As disclosed herein, microarray analysis of steady state RNA levels shows altered gene expression between dendritic cells produced from day old monocytes as compared to dendritic cells produced from fresh monocytes. Thus, in one embodiment, the invention provides a mature monocyte-derived dendritic cell, wherein the steady state ratio of ALOX15 RNA to either β-actin RNA or GAPDH RNA in the cell is less that 1.0. Preferably, the ratio is between 0.2 to 0.7, more preferably between 0.4 to 0.5, and most preferably about 0.45.

In another embodiment, the invention provides a mature monocyte derived dendritic cell, wherein the steady state ratio of CD52 RNA to β-actin RNA or GAPDH in the cell is greater than 1.0. Preferably, the ratio is between 1.2 to 5.0, more preferably between 1.5 to 2.2, or between 1.8 to 1.9, and most preferably the ratio is 1.86.

In still another embodiment, the invention provides a mature monocyte derived dendritic cell, wherein the steady state ratio of TLR1 RNA, TLR2 RNA, IL-1β RNA or CD69 RNA to β-actin RNA or GAPDH RNA in the cell is less than 1.0. Preferably the ratio is between 0.2 to 0.9, and more preferably between 0.5 to 0.8.

The human ALOX15 mRNA (SEQ ID NO:1) and allelic variants thereof can be detected using the Affymetrix probes of SEQ ID NOs:2-12. The human IL-1β mRNA (SEQ ID NO:13) and allelic variants thereof can be detected using the Affymetrix probes of SEQ ID NOs:14-24. The human TLR1 mRNA (SEQ ID NO:25) and allelic variants thereof can be detected using the Affymetrix probes of SEQ ID NOs:26-36. The human TLR2 mRNA (SEQ ID NO:37) and allelic variants thereof can be detected using the Affymetrix probes of SEQ ID NOs:38-48. The human CD69 mRNA (SEQ ID NO:49) and allelic variants thereof can be detected using the Affymetrix probes of SEQ ID NOs:50-60. The human CD52 mRNA (SEQ ID NO:61) and allelic variants thereof can be detected using the Affymetrix probes of SEQ ID NOs:62-77. The human GAPDH mRNA (SEQ ID NO:78) and allelic variants thereof can be detected using the Affymetrix probes of SEQ ID NOs:79-98. The human β-actin mRNA (SEQ ID NO: 99) and allelic variants thereof can be detected using Affymetrix probes of SEQ ID NOs:100-119.

RNA steady state expression levels can be detected by microarray, preferably using the Affymetrix Human Genome U133 Plus 2.0 Array. Alternatively, hybridization can be performed using the gene specific probes listed in the paragraph above. Preferably, RNA samples extracted from dendritic cells can be applied to the Human Genome U133 Plus 2.0 Array (Affymetrix, Santa Clara, Calif.) according to the manufacture's instruction (Genechip® Expression Analysis Technical Manual, 2004). Briefly, three micrograms of total RNA spiked with Genechip® Poly-A RNA Control Kit (Affymetrix, Santa Clara, Calif.) are converted to first-strand cDNA using SuperScript™ II reverse transcriptase. Second-strand cDNA synthesis is followed by in vitro transcription for linear amplification of each transcript and incorporation of biotinylated CTP and UTP. The cRNA products are fragmented to around 100 nucleotides, and hybridized for 16 hours to the microarrays. The microarrays are then washed at low (6×SSPE) and high (100 mM MES, 0.1 M NaCl) stringency and stained with streptavidin-phycoerythrin.

Fluorescence is amplified by adding biotinylated anti-streptavidin and an additional aliquot of streptavidin-phycoerythrin stain. The GeneChip® Scanner 3000 (Affymetrix, Santa Clara, Calif.) is used to collect fluorescence signal at 3 µm resolution after excitation at 570 nm. The average signal from two sequential scans is calculated for each microarray feature of interest. Scanned images were analyzed with Genechip® Operating Software v1.1 (Affymetrix, Santa Clara, Calif.). Preferably, high linear correlation ($R^2>0.95$) of 4 control RNAs included in Poly-A RNA Control Kit (Affymetrix, Santa Clara, Calif.) is confirmed as a control for the success of the labeling process.

Profile data for all genes, or just the genes of interest (e.g., ALOX15, IL-1β, TLR1, TLR2, CD69 and/or CD52, as well as β-actin and/or GAPDH) are imported into the computer program GeneSpring™ and normalized. Three steps are performed in the normalization step according to the standard method suggested by GeneSpring™ for Affymetrix arrays.

1) data transformation (all values less than 0.01 were set to 0.01)
2) Normalization to the $50^{th}$ percentile.
3) Normalization to the median.

The ratio of steady state mRNA of interest (ALOX15, IL-1β, TLR1, TLR2, CD69 or CD52 mRNA) to steady state GAPDH or β-Actin mRNA can then be determined by dividing the normalized expression of the mRNA of interest by the normalized expression of GAPDH or β-actin mRNA.

The antigen-loaded dendritic cells of the invention are useful as vaccines in the treatment or prevention of disease or for the activation of T cells, which can then be used in therapy. For example, antigen loaded dendritic cells can be used to elicit an immune response against an antigen. They may be used as vaccines to prevent future infection or disease, or to activate the immune system to treat ongoing disease, such as, but not limited to pathogen infection or cancer. The antigen loaded dendritic cells may be formulated for use as vaccines or pharmaceutical compositions with suitable carriers such as physiological buffers or other injectable liquids. The vaccines or pharmaceutical compositions would be administered in therapeutically effective amounts sufficient to elicit an immune response.

Preferably, the dendritic cells are loaded with an antigen autologous to the subject from which the dendritic cell is derived, and administered to the same subject. See for example, U.S. Pat. No. 5,853,719 (the contents of which is incorporated by reference), which describes the preparation and uses of antigen loaded dendritic cells and particularly RNA loaded dendritic cells. Alternatively the dendritic cell may be loaded with an antigen that is not autologous to the intended recipient of the DC therapy. Examples of such antigens include, but are not limited to antigens that are known therapeutic targets, such as telomerase, prostate specific antigen, and other tumor markers, or known antigens from a pathogen.

Methods for Collecting Monocytes or PBMCs Comprising Monocytes

A variety of methods for collecting monocytes and PBMCs comprising monocytes from a subject are known to those of ordinary skill in the art. See for example, gambrobct.com/Products_&_Services/ for detailed information on leukapheresis for the collection PBMCs and elutriation for the purification of monocytes. In a preferred embodiment, a leukapheresis product and plasma are collected in separate sterile, disposable, single-use cytopheresis bags is collected using the AutoPBSC (Automated Peripheral Blood Stem Cell) procedure on a Gambro BCT COBE Spectra (Gambro BCT, Lakewood, Colo.).

In one alternative method to leukapheresis, PBMCs are obtained by collecting blood in a heparinized syringe, dilution in PBS, layering over Histopaque 1077 (Sigma), centrifugation and recovery of PBMCs at the interface. See Woodhead et al. (2000) International Immunol 12:1051-1061. Additional methods of collecting, purifying or fractionating PBMCs are known to those of ordinary skill in the art.

Following collection of the leukapheresis product or other blood product, monocytes contained therein are incubated at 1-34° C. for 6-96 hours. In one embodiment, the leukapheresis product is collected in a bag and then transported to the vaccine manufacturing facility in a temperature-monitored shipping container maintained at 1-34° C., preferably at about 6-28° C., and most preferably at 8-26° C. Gel packs, such as those disclosed in U.S. Pat. No. 4,102,807, which aid in the prevention of temperature changes, can be included in the shipping container. For example, the monocytes can be shipped in an insulated container (e.g., ThermoSafe™ model E65 polyurethane foam insulated container), and packed with ThermoSafe™ U-tek gel packs and gel mats as shown in FIG. 1. For example, in the packing procedure shown in FIG. 1, a 16 oz U-tek gel mat adjusted to a temperature of −1° C. is laid flat in the bottom of the E65 container. Two 16 oz U-tek gel mats (−1° C.) are folded and placed between the first gel mat and the short wall of the E65 container. Two 16 oz U-tek gel (adjusted to +18° C.) are then placed vertically next to the previous gel mats. A ThermoSafe™ INF3000 transplant container is placed between the gels. The leukapheresis bags are placed in a sealed inner bag (STP711). A device which records the temperature of the inner bag can be used to monitor the temperature during shipment. One such device is the ThermoSafe™ DataLogger. The inner bag is placed in a sealed outer bag (STP710) and then the bags are placed in the INF3000 container. A 16 oz U-tek gel (+18° C.) is placed on top of the closed INF300 container, topped with Kraft paper and then a 4" foam plug. The box is then sealed with tape and ready for shipment.

During or after the incubation period at 1-34° C., the leukapheresis product can be further processed or purified, for example by Ficoll density gradient centrifugation at room temperature in 50 ml conical tubes to separate and concentrate the mononuclear cell fraction that includes dendritic cell precursors (monocytes). Preferably, after multiple washing steps with phosphate buffered saline (PBS), the cell concentration and cell viability can be determined.

Enrichment for Monocytes

Methods of enriching for monocytes are know to those of ordinary skill in the art, and include, but are not limited to, density gradient centrifugation (e.g, dilute Ficoll density gradient centrifugation, dilute Percoll density gradient centrifugation, etc.), elutriation, adherence to plastic, tangential flow filtration, fluorescence activated cell sorting (FACS), immunological cell separation techniques (antibody panning to select monocytes or to remove non-monocytes (e.g., leukocytes, macrophages, granulocytes, etc), differential lysis, magnetic cell sorting, etc.), culture in plastic culture bags coated with plastic microcarrier beads, etc. See, for example, O'Doherty et al. (1993) J Exp Med 178:1067-1076; Young et al. (1990) J Exp Med 171:1315-1332; Freudenthal et al. (1990) PNAS 87:7698-7702; Bernhard et al. (1995) Cancer Res 55:1099-1104; Caux et al. (1992) Nature 360:258-261; Read et al. (2003) "Evaluation of a Closed Automated System to Isolate Peripheral Blood Monocytes for Dendritic Dell (DC) Immunotherapy", Ninth annual meeting of the ISCT; Mu et al. (2003) Scand J Immunol 58:578-586; Maffei et al. (2000) Transfusion 40:1419-1420; mitenyibiotec.com; Meyer-Wentrup et al. (2003) J Hematother Stem Cell Res 12:289-299; and WO 2004/000444, the contents of which are incorporated by reference. For example, magnetic cell sorting can be used to enrich form monocytes by positive selection (CD14+ cells) or by negative selection (i.e., removal of cells that are not monocytes; e.g., CD3+, CD19+ and CD2+ cells).

Preferably, monocytes are enriched from the leukapheresis product by elutriation, an automated method to isolate monocytes from the subject leukapheresis. Methods of leukapheresis are known in the art. For example, elutriation can be performed on the Gambro BCT Elutra™ Cell Separation System (Gambro BCT, Lakewood, Colo.). Elutriation buffer can be prepared by adding 1000 mL of 5% Human Albumin Serum (HSA) to a 4 L bag of Hank's Balanced Salt Solution (HBSS). The cells can be fractionated by elutriation according to the manufacturer's protocol. In a preferred embodiment, a modified version of the manufacturer's (Gambro) protocol is used for elutriation, where the final rotor off fraction is the fourth fraction instead of the fifth fraction. CBC with differential analysis can performed on the monocyte fraction to verify purity and recovery. Alternatively, monocyte purity can be assessed by immunophenotyping with CD14. The enriched monocytes can then be differentiated into dendritic cells, or can be frozen and stored for later use. In one embodiment, the cells are frozen in 25 ml or 50 mL freezing bags. Examples of freezing bags include Cryocyte™ freezing bags, Origen™ freezing bags (Cryostore) and Pall™ freezing bags. Preferably, each freezing bag contains 15 mL of up to $3 \times 10^9$ cells in culture medium (e.g., AIM V, X-VIVO, RPMI, etc.) with approximately 10-12% DMSO and 10-20% heat inactivated, filtered plasma, about 107 to 507 mg/L final concentration of $CaCl_2$ and about 44 to 241 mg/L final concentration of $MgSO_4$. The cells can be frozen using a controlled rate freezer, then stored cryogenically.

In an alternative embodiment, after incubation of PBMCs and purification by Ficoll density gradient, the PBMCs are resuspended in AIM-V® medium and seeded in T150 cm² flasks at $2.0 \times 10^8$ cells per flask. In the event that an insufficient number of PBMCs are obtained, the PBMCs may be frozen and combined with a second leukapheresis. Monocytes are selected from the mononuclear cell population of PBMCs by adhesion to sterile tissue culture plastic flasks for one to two hours at 37° C., 5% $CO_2$, $\geq$75% humidity. Non-adherent and semi adherent cells are removed. PBS is added to the flasks to remove the remaining non-adherent cells, semi-adherent cells and residual medium. The remaining adherent cells are predominantly monocytes, and represent a population of enriched monocytes.

Methods for Differentiating Monocytes into Dendritic Cells

A variety of methods for differentiating monocytes into dendritic cells are known to those of ordinary skill in the art. See U.S. Pat. No. 6,607,722, WO 97/29182, Romani, et al. (1994) J. Exp. Med. 180:83-93; Sallusto and Lanzavecchia (1994) J. Exp. Med. 179:1109 and on, and Reddy et al. (1997) Blood 90:3640-3646; the contents of which are incorporated by reference. Most of these methods involve culturing monocytes in the presence of cytokines which induce the differentiation of monocytes into dendritic cells. Examples of alternative methods for differentiating monocytes into dendritic cells include, but are not limited to exposure to physical perturbation (e.g., shearing), irradiation in the presence of a photo-activatable agent capable of forming photoadducts with cellular DNA components, and/or treatment with a DNA binding agent, followed by incubation with disease effector agents, such as microbes, fungi, viruses, and malignant cells. See U.S. Pat. No. 6,607,722, the contents of which are incorporated by reference.

In one embodiment, monocytes are differentiated into dendritic cells by culture in medium comprising a composition that induces differentiation of monocytes into dendritic cells. Suitable media for the culture of monocytes, immature and mature dendritic cells includes, but is not limited to, AIM-V, X-VIVO-15, RPMI, DMEM, and the like. Compositions that induce the differentiation of monocytes into dendritic cells are known in the art, and include, but are not limited to, GM-CSF plus IL-4; GM-CSF plus IL-13; and IFN$\alpha$.

In a preferred embodiment, enriched monocytes are differentiated into dendritic cells by culture in the presence of GM-CSF and IL-4 (see, e.g., WO 97/29182; Sallusto and Lanzavecchia (1994) J. Exp. Med. 179:1109; and Romani et al. (1994) J. Exp. Med. 180:83-93). Briefly, enriched monocytes, preferably at a concentration of $1 \times 10^6$ cells/ml are cultured in AIM V medium, X-VIVO 15 medium, or other suitable medium in the presence 800 U/ml GM-CSF and 500 U/ml IL-4 for approximately 4-7 days, preferably 6 days at 37° C., 5% $CO_2$, $\geq$75% humidity to allow the differentiation of monocytes into immature dendritic cells. Cytokine concentrations can be varied. For example, preferred concentrations of GM-CSF are 500 to 1500 U/ml, more preferably 700 to 1000 U/ml, most preferably 800 U/ml. Preferred concentrations of IL-4 are 400-1500 U/ml, more preferably 450 to 1000 U/ml, most preferably 500 U/ml. IL-13 or IL-15 can be used in place of or in addition to IL-4. IFN$\alpha$ can be used in place of GM-CSF plus IL-4, IL-13 or IL-15. As the monocytes differentiate into dendritic cells, they progressively lose expression of CD14 and acquire CD80 expression consistent with the phenotype of dendritic cells in the immature state.

Methods for the Maturation of Immature Dendritic Cells into Mature Dendritic Cells Methods of maturing immature dendritic cells into mature dendritic cells are known to those of ordinary skill in the art, and include, but are not limited to, antigen uptake and/or contact with compositions that induce maturation. Compositions that induce maturation of immature dendritic cells include, but are not limited to, monocyte conditioned medium; PBMC conditioned medium; fixed *Staphylococcus aureus* (Pansorbin™); lipopolysachamides (LPS); other bacterial cell products, such as monophosphoryllipid A (MPL), lipoteichoic acid, etc.; phosphorylcholine; calcium ionophores; phorbol esters such as PMA; heat-shock proteins; nucleotides, such as ATP, etc.; lipopeptides; Toll-like receptor 4; artificial ligands for Toll-like receptors; double stranded RNA, such as poly-I:C, etc.; immunostimulant DNA sequences; maturation cocktail (TNF-$\alpha$, IL-6, IL-1$\beta$ and PGE2); GM-CSF, IL-4 and maturation cocktail (TNF$\alpha$, IL-6, IL-1$\beta$ and PGE$_2$), GM-CSF, IL-4, PGE$_2$ and sequential signaling of IFN$\gamma$ followed by signaling with CD40L; and the like. See, for example, Cisco et al. (2004) J Immunol 172: 7162-7168; Jonluit et al. (1997) Eur J Immunol 27:3135-3142; U.S. patent application 20040203143; PCT application PCT/US2005/036304 and U.S. patent application Ser. No. 11/246,387, the contents of which are incorporated by reference.

In one embodiment, a maturation cocktail containing TNFα, IL-6, IL-1β and PGE$_2$ is added to a culture of immature dendritic cells. The cells are then cultured overnight (approximately 12 hours or more) to produce mature dendritic cells.

In one alternative embodiment, immature dendritic cells are transfected, preferably by electroporation, with mRNA encoding CD40L, and optionally with mRNA encoding one or more antigens, and then cultured overnight (approximately 12 hours or more) in the presence of IFNγ and optionally PGE$_2$ to produce mature dendritic cells. A human CD40L cDNA and protein are shown in SEQ ID NO:120 and SEQ ID NO:121, respectively. Other CD40L mRNAs are known to those of skill in the art.

In a preferred embodiment, a maturation formulation in AIM V medium is added directly to the immature DC to give a final concentration of TNF-α (10 ng/ml), IFN-γ (1000 U/ml), and PGE$_2$ (1 μg/ml). The cells can then cultured overnight (approximately 12 hours or more) to produce mature dendritic cells. Maturation can optionally be further increased by exposure of the cells to CD40 Ligand (CD40L), either added to the culture media, or more preferably expressed within the cell. CD40L can be expressed constitutively or transiently. Preferably, the mature dendritic cells are transfected with an mRNA encoding CD40L, and optionally with mRNA encoding one or more antigens of interest.

Antigens

Any antigen can be loaded into immature or mature dendritic cells. The antigen will then be processed and presented by the mature DCs. Examples of antigens include, but are not limited to, viral particles, bacteria, or other pathogens, proteins, and fragments thereof, polypeptides, pathogen lysates, pathogen extracts, pathogen nucleic acids, cancer cells, cancer cell proteins and fragments thereof, cancer cell lysates, cancer cell extracts and cancer cell nucleic acids. Antigens can be naturally occurring, chemically processed or recombinantly produced. The antigens can be delivered to the cells as polypeptides, proteins or as nucleic acids using methods known in the art.

An antigen may be delivered in its "natural" form in that no human intervention was involved in preparing the antigen or inducing it to enter the environment in which it encounters the dendritic cell. Alternatively or additionally, the antigen may comprise a crude preparation, for example of the type that is commonly administered in a conventional allergy shot or in a tumor lysate. The antigen may alternatively be substantially purified, e.g., at least about 90% pure.

Where the antigen is a peptide, it may be generated, for example, by proteolytic cleavage of isolated proteins. Any of a variety of cleavage agents may be utilized including, but not limited to, pepsin, cyanogen bromide, trypsin, chymotrypsin, etc. Alternatively, peptides may be chemically synthesized, preferably on an automated synthesizer such as is available in the art, or recombinantly expressed. In addition, recombinant techniques may be employed to create a nucleic acid encoding the peptide of interest, and to express that peptide under desired conditions. Alternatively, antigen encoding nucleic acids may be purified or derived from a cell, tissue or virus.

The antigen can have a structure that is distinct from any naturally-occurring compound. In certain embodiments of the invention, the antigen is a "modified antigen" in that the antigen has a structure that is substantially identical to that of a naturally-occurring antigen but that includes one or more deviations from the precise structure of the naturally-occurring compound.

For instance, where the naturally-occurring antigen is a protein or polypeptide antigen, a modified antigen as compared with that protein or polypeptide antigen would have an amino acid sequence that differs from that of the naturally-occurring antigen in the addition, substitution, or deletion of one or more amino acids, and/or would include one or more amino acids that differ from the corresponding amino acid in the naturally-occurring antigen by the addition, substitution, or deletion of one or more chemical moieties covalently linked to the amino acid. In one aspect, the naturally-occurring and modified antigens share at least one region of at least 5 amino acids that are at least 75% identical. Those of ordinary skill in the art will appreciate that, in comparing two amino acid sequences to determine the extent of their identity, the spacing between stretches (i.e., regions of at least two) of identical amino acids need not always be precisely preserved. Naturally-occurring and modified protein or polypeptide antigens can show at least approximately 80% identity, more alternatively 85%, 90%, 95%, or greater than 99% identity in amino acid sequence for at least one region of at least 5 amino acids. Often, it may be useful for a much longer region (e.g., 10, 20, 50, or 100 or more amino acids) of amino acid sequence to show the designated degree of identity.

In preferred embodiments, the antigen is delivered as a polynucleotide or gene encoding the antigen, so that expression of the gene results in antigen production either in the individual being treated (when delivered in vivo) or the cell culture system (when delivered in vitro). Techniques for generating nucleic acids including an expressible gene or mRNA, and for introducing such nucleic acids into an expression system in which any protein encoded by the expressible gene will be produced are known in the art and briefly described infra. Preferably, the antigen is delivered as an mRNA. RNA or mRNA obtained from a cell (for example a cancer cell, pathogen cell or pathogen-infected cell) can be loaded directly into dendritic cells. Alternatively, RNA or mRNA can be amplified prior to loading. In one embodiment, total or targeted mRNA is amplified by RT-PCR using a primer containing a sense promoter to make a cDNA expression construct. RNA transcribed in vitro from the expression construct can then be used to load the cells. Methods for isolating, amplifying, in vitro transcribing the RNA and loading RNA or other nucleic acids into dendritic cells are known to those of skill in the art. See, for example, PCT/US04/39539 and U.S. provisional application 60/522,310, the contents of which are incorporated by reference.

In one embodiment of the invention, the antigen is one or more HIV proteins or fragments thereof. As a non-limiting example, plasma from an HIV infected patient can serve as a source for isolation of HIV RNA. In one embodiment, a portion of the plasma is centrifuged, and the supernatant is collected and filtered using 0.22 μm filters and stored at −20° C. until use in formulation of the dendritic cell vaccine. The HIV RNA present in plasma is amplified by RT-PCR and in vitro transcription reactions to provide a sufficient quantity of amplified HIV RNA for loading into dendritic cells. Briefly, viral RNA is reverse transcribed in to single-stranded (ss) DNA using a reverse transcriptase, appropriate reaction buffers and random hexamers or targeted reverse primers. The single-stranded cDNA is then amplified by PCR into double-stranded DNA in a primary PCR reaction using multiplex primers. The identity of region(s) amplified in the primary PCR reaction is determined by the selection of specific primers complimentary to target sequences which flank those regions. The product of the primary PCR reaction is purified using a QIAquick® PCR Purification Kit and then serves as the template in a second round or nested PCR amplification. In this round of amplification, the 5' primers(s) contains an overhang with an RNA polymerase binding site (e.g., a T7 promoter), and the 3' primer contains an overhang with poly T stretches. The modifications introduced by the overhanging regions in a nested round of PCR enable transcription of the PCR product in vitro and successful translation upon delivery into dendritic cells. Purification of the in vitro transcribed RNA is performed using the Qiagen RNeasy® Kit, and the RNA is eluted in nuclease-free water. If necessary, ethanol precipitation is performed to concentrate the RNA. The RNA is re-suspended in nuclease-free water and passed through a 0.8/0.2 µm polyethersulfone (PES) filter, then dispensed into 0.5 ml safe-lock polypropylene tubes and loaded into DC or cryopreserved at $\leq -150°$ C. for until thawing prior to transfection.

In another preferred embodiment, RNA or mRNA is extracted from one or more cancer cells. The RNA or mRNA can be loaded directly into dendritic cells, or it can first be amplified by RT-PCR and in vitro transcription using the methods described in PCT/US04/39539.

Antigen Loading of Dendritic Cells

Dendritic cells may be loaded with one or more antigens as immature dendritic cells, mature dendritic cells, or during differentiation from immature to mature dendritic cells. Dendritic cells are capable of ingesting antigens, such as proteins, peptides, viruses, cells, cell lysates, and the like. Accordingly, antigen loading can be performed simply by contacting the dendritic cell with the antigen or nucleic acid encoding the antigen. Other methods for loading dendritic cells are known to those of skill in the art, including, but not limited to nucleic acid transfection, exosomes, viral vectors, microparticle delivery, etc. See for example, Mitchell et al. (2000) Curr Opin Mol Ther 2:176-181; Zitovogel et al. (1998) Nature 4:594-600; Jenne et al., (2001) Trends Immunol 22:102-106, and U.S. patent publication 2005/0158856 the contents of which are incorporated by reference. One or more antigens may be loaded directly into the dendritic cells, or nucleic acids encoding one or more antigens may be loaded (transfected) into the dendritic cells. In a preferred embodiment, the dendritic cells are loaded with nucleic acids encoding one or more antigens. Preferably, the nucleic acid is an mRNA.

Method of transfecting nucleic acids into dendritic cells are known to those of ordinary skill in the art and include, but are not limited to, passive transfection, lipid-mediated transfection, cationic lipid-mediated transfection (e.g., DOTAP), cationic peptide mediated transfection, electroporation. See Nair et al. (1998) Nat Biotechnology 16:364-369; Van Tendeloo et al. (2001) Blood 98:49-56; Saeboe-Larssen et al. (2002) J Immunol Methods 259:191-203; Boczkowski et al (2000) Cancer Res 60:1028-1034; Gilboa et al. Immunol Rev (2004) 199:251-263; U.S. provisional application 60/583,579; and U.S. patent application Ser. No. 10/177,390, the contents of which are incorporated by reference.

Loading Dendritic Cell by Peptide Pulsing

Methods for loading dendritic cells with proteins, polypeptides, peptides, cell or tissue extracts and other types of antigens are known to those of ordinary skill in the art. In a preferred embodiment, immature dendritic cells are loaded with one or more antigens. In one embodiment of the invention, peptides, polypeptides and/or cell or tissue extracts are loaded simply by incubation with immature dendritic cells in culture medium.

Antigen Loading by Electroporation Followed by Maturation of Immature Dendritic Cells Using a Cytokine Cocktail In one embodiment of the invention, immature dendritic cells are harvested by tapping the culture flask to dislodge the cells. Cells in suspension are then transferred to conical tubes. PBS is added to the culture flask to remove the remaining floating cells and residual medium, which is added to the conical flask. Some immature dendritic cells may remain adherent to the flask. Detachment of these cells is promoted by adding PBS and incubating the flasks at anywhere from 2° C. up to room temperature. At the end of the incubation period, the flasks are tapped and the dislodged cells are added to the conical tubes. The total cell suspension is then pelleted, washed in PBS and re-suspended in chilled ViaSpan® at $4 \times 10^7$/ml in 0.5 ml and placed on ice. DCs are mixed with mRNA at 2 µg/$10^6$ cells for mRNA encoding antigen(s) and placed in a 4 mm gap electroporation cuvette and electroporated at a pulse of 275-350V, 100-300Ω and 150 µF, and preferably at 325V, 200Ω. Immediately after electroporation, DCs are washed in X-VIVO 15 medium and re-suspended at $1 \times 10^6$/ml in X-VIVO 15 supplemented with GM-CSF (800 U/ml), IL-4 (500 U/ml) and $PGE_2$ (1 µg/ml), TNF-α (10 ng/ml), IL-1β (10 ng/ml) and IL-6 (100 ng/ml). The immature dendritic cells are then incubated overnight at 37° C., 5% $CO_2$, $\geq 75\%$ humidity to produce stably mature dendritic cells. Mature dendritic cells are then washed in PBS.

Antigen Loading by Electroporation and Maturation Using CD40L

In one embodiment of the invention, immature dendritic cells are matured using CD40L and IFN-γ. Preferably, immature DCs are transfected with 4 µg CD40L mRNA per 106 and mRNA (2 µg/$10^6$ cells) encoding one or more antigens by electroporation as described above, and then are cultured overnight in X-VIVO 15 supplemented with GM-CSF (800-1000 U/ml), IL-4 (500-1000 U/ml), IFN-γ (500-1000 U/ml) or TNF-α (10 ng/ml) and $PGE_2$ (1 µg/ml) to generate stable mature dendritic cells. Dendritic cells matured by this process secrete higher levels of IL-12 (a T cell growth factor), and minimal IL-10, as compared to dendritic cell matured by the cytokine cocktail process described above.

Antigen Loading by Electroporation of Mature Dendritic Cells

Mature Dendritic cells can be loaded with antigen by methods known to those of skill in the art. In one non-limiting embodiment of the invention, on the sixth day after initiating differentiation of monocytes into immature dendritic cells, a maturation formulation in AIM V medium is added directly to the immature DC to give a final concentration of TNF-α (10 ng/ml), IFN-γ (1000 U/ml), and $PGE_2$ (1 µg/ml). The cells are then cultured overnight to produce mature dendritic cells. The DC are then harvested and co-electroporated with 1 µg of antigen encoding RNA and optionally with 4 µg of CD40L RNA per $10^6$ cells. Post-electroporation, the cells are cultured for 4 hours at $1 \times 10^6$ cells AIM V medium supplemented with GM-CSF (800 U/mL), and IL-4 (500 U/mL). The cells can then be formulated for administration to a subject without freezing, or formulated for freezing. For freezing, the cells are preferably formulated in heat inactivated autologous plasma, 10% DMSO, and 5% dextrose at $2 \times 10^7$ cells/mL. Cryogenic vials are filled with 0.7 mL for a total number of $1.4 \times 10^7$ cells per vial. Vials are then frozen in alcohol boxes at $-85°$ C. for a minimum of 4 hours and transferred to the cryogenic freezer for storage. The frozen dendritic cell vaccine can then be thawed and administered to a subject without washing or reformulation.

Flow Cytometry Analysis of DCs to Assess Maturation

In a preferred method, $10^6$ DCs are harvested and re-suspended in chilled PBS/1% FCS. Phycoerythrin (PE) or FITC conjugated antibodies specific for MHC molecules (HLA-ABC, HLA-DR), co-stimulatory molecules (CD80, CD86), maturation markers (CD83) and monocyte markers (CD14) are mixed with $1 \times 10^5$ DCs per well in a 96 well plates (BD Biosciences) and incubated at 4° C. for a minimum of 15 minutes. Isotype matched antibodies were used as controls.

After thorough washing, fluorescence analysis was performed with a FACScalibur flow cytometer (BD Biosciences) using CellQuest software (BD Biosciences).

Vaccine Formulation

Methods for formulating dendritic cell vaccines are known to those of skill in the art. In a preferred embodiment, the mature dendritic cells are washed and resuspended in heat-inactivated plasma (preferably autologous plasma) and 10% dextrose at a concentration of $4 \times 10^7$ cells/ml. The cells can then be diluted 1:1 with a mixture of heat-inactivated plasma and 20% DMSO to give a final concentration of 5% dextrose, 10% DMSO in heat-inactivated plasma. The target final filled formulation is $1.4 \times 10^7$ cells/0.7 ml in a container suitable for cyropreservation. The dendritic cells can then be administered to a patient or frozen, preferably at −85° C., and stored in cryogenic freezer (preferably in a dry liquid nitrogen freezer designed to prevent contamination), preferably at a temperature of $\leq -150°$ C. The frozen vaccine can then be shipped to a clinical site for patient administration (preferably by intradermal injection). Upon thawing, the vaccine can be administered directly to the patient without further processing.

Other suitable formulations for administration can include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, immunostimulants, cytokines and adjuvants.

In a preferred embodiment, mature dendritic cells are suspended in heat-inactivated autologous plasma and 10% dextrose, at a final concentration of $4 \times 10^7$ cells/ml. These cells are then diluted 1:1 with a mixture of heat-inactivated autologous plasma and 20% DMSO to give a final concentration of $2 \times 10^7$ cells/ml in heat inactivated autologous plasma which contains 5% dextrose and 10% DMSO. The final filled formulation is $1.4 \times 10^7$ cells/0.7 ml in a container suitable for cyropreservation. The vaccine is then frozen and stored at $\leq 150°$ C. in a dry liquid nitrogen freezer. The vaccine is ready for administration after thawing, without the need for washing and resuspending.

Methods of Administration

The dendritic cell vaccine can be administered by a variety of methods, such as, but not limited to, injection (e.g., subcutaneous, intradermal, intravenous, intralymphatic, intraarticular, intramuscular, intraperitoneal), by continuous infusion, sustained release from implants, etc. DC vaccines have typically been administered at two to four week intervals. The dendritic cell vaccine can be administered with physiologically acceptable carriers, buffers, diluents, adjuvants, immunomodulators, etc. Preferably, the dendritic cell vaccine is autologous to the patient it is administered to, or is HLA matched.

The dose of cells (e.g., activated T cells, or dendritic cells) administered to a subject is in an effective amount, effective to achieve the desired beneficial therapeutic response in the subject over time, or to inhibit growth of cancer cells, or to inhibit infection. A preferred dose is approximately $10^7$ cells. Biological response modifiers are optionally added for treatment by the DCs or activated T cells of the invention. For example, the cells are optionally administered with an adjuvant, or cytokine such as GM-CSF, IL-12 or IL-2.

Methods to Assess Immunogenicity of Antigen-Loaded Dendritic Cells or Educated T Cells The immunogenicity of the antigen-loaded dendritic cells or educated T cells produced by the methods of the invention can be determined by well known methodologies including, but not limited to the following:

$^{51}$Cr-release lysis assay. Lysis of peptide-pulsed $^{51}$Cr-labeled targets by antigen-specific T cells can be compared. "More active" compositions will show greater lysis of targets as a function of time. The kinetics of lysis as well as overall target lysis at a fixed timepoint (e.g., 4 hours) may be used to evaluate performance. Ware, C. F. et al. (1983) J. Immunol. 131:1312.

Cytokine-release assay. Analysis of the types and quantities of cytokines secreted by T cells upon contacting modified APCs can be a measure of functional activity. Cytokines can be measured by ELISA or ELISPOT assays to determine the rate and total amount of cytokine production. Fujihashi, K. et al. (1993) J. Immunol. Meth. 160:181; Tanquay, S. and Killion, J. J. (1994) Lymphokine Cytokine Res. 13:259.

In vitro T cell education. The compositions of the invention can be assayed for the ability to elicit reactive T cell populations from normal donor or patient-derived PBMC. In this system, elicited T cells can be tested for lytic activity, cytokine-release, polyclonality, and cross-reactivity to the antigenic epitope. Parkhurst, M. R. et al. (1996) J. Immunol. 157:2539.

Proliferation Assays. T cells will proliferate in response to reactive compositions. Proliferation can be monitored quantitatively by measuring, for example, 3H-thymidine uptake. Caruso, A. et al. (1997) Cytometry 27:71.

Transgenic animal models. Immunogenicity can be assessed in vivo by vaccinating HLA transgenic mice with the compositions of the invention and determining the nature and magnitude of the induced immune response. Alternatively, the hu-PBL-SCID mouse model allows reconstitution of a human immune system in a mouse by adoptive transfer of human PBL. These animals may be vaccinated with the compositions and analyzed for immune response as previously mentioned in Shirai, M. et al. (1995) J. Immunol. 154:2733; Mosier, D. E. et al. (1993) Proc. Natl. Acad. Sci. USA 90:2443.

Primate models. A non-human primate (chimpanzee) model system can be utilized to monitor in vivo immunogenicities of HLA-restricted ligands. It has been demonstrated that chimpanzees share overlapping MHC-ligand specificities with human MHC molecules thus allowing one to test HLA-restricted ligands for relative in vivo immunogenicity. Bertoni, R. et al. (1998) J. Immunol. 161:4447.

Monitoring TCR Signal Transduction Events. Several intracellular signal transduction events (e.g., phosphorylation) are associated with successful TCR engagement by MHC-ligand complexes. The qualitative and quantitative analysis of these events have been correlated with the relative abilities of compositions to activate effector cells through TCR engagement. Salazar, E. et al. (2000) Int. J. Cancer 85:829; Isakov, N. et al. (1995) J. Exp. Med. 181:375).

Methods for Isolating and Characterizing Immune Cells

Cell isolation or immunoassays for detection of cells during cell purification can be performed in any of several configurations, e.g., those reviewed in Maggio (ed.) (1980) Enzyme Immunoassay CRC Press, Boca Raton, Fla.; Tijan (1985) "Practice and Theory of Enzyme Immunoassays," Laboratory Techniques in Biochemistry and Molecular Biology, Elsevier Science Publishers B.V., Amsterdam; Harlow and Lane, supra; Chan (ed.) (1987) Immunoassay: A Practical Guide Academic Press, Orlando, Fla.; Price and Newman (eds.) (1991) Principles and Practice of Immunoassays Stockton Press, NY; and Ngo (ed.) (1988) Non-isotopic Immunoassays Plenum Press, NY.

Cells can be isolated and characterized by flow cytometry methods such a FACS analysis. A wide variety of flow-cytometry methods are known. For a general overview of fluorescence activated flow cytometry see, for example, Abbas et al. (1991) Cellular and Molecular immunology W.B. Saunders Company, particularly chapter 3, and Kuby (1992) Immunology W.H. Freeman and Company, particularly chapter 6. FACS machines are available, e.g., from Becton Dickinson.

Labeling agents which can be used to label cell antigen include, but are not limited to monoclonal antibodies, polyclonal antibodies, proteins, or other polymers such as affinity matrices, carbohydrates or lipids. Detection proceeds by any known method, such as immunoblotting, western blot analysis, tracking of radioactive or bioluminescent markers, capillary electrophoresis, or other methods which track a molecule based upon size, charge or affinity.

The following examples are intended to illustrate, rather than to limit the invention.

EXAMPLES

Example 1

Dendritic Cell Prepared from Day-Old Leukapheresis

Peripheral blood mononuclear cells (PBMCs) were collected from 4 human donors by leukapheresis and transported by overnight delivery to a dendritic cell manufacturing facility in temperature-monitored shipping containers maintained at a temperature of 8° C.-26° C. The day of delivery, the leukapheresis product underwent Ficoll density gradient centrifugation in 50 ml conical tubes (800×g) for 20 minutes at room temperature (approximately 19-22° C.) to separate and concentrate the mononuclear cell fraction that includes the dendritic cell precursors (monocytes). After two washing steps with phosphate buffered saline (PBS), cell concentration and cell viability were determined. After the third centrifugation/washing step with PBS, mononuclear cells were resuspended in StemSpan™ H2000 medium (StemCell Technologies, Inc.) and seeded in T150 cm$^2$ flasks at 2.0×10$^8$ cells per flask. Monocytes were then selected from the mononuclear cell population by adhesion to the sterile tissue culture plastic flask for 1-2 hours at 37° C., 5% $CO_2$, ≧75% humidity. Non-adherent and semi-adherent cells (primarily lymphocytes) were discarded. The remaining adherent cells, which were predominantly monocytes, were cultured in StemSpan™ H2000 medium containing GM-CSF (800 U/ml) and IL-4 (500 U/ml). These cells were incubated for 6 days at 37° C., 5% $CO_2$, ≧75% humidity to allow the differentiation of monocytes into immature dendritic cells.

The immature dendritic cell-rich population was harvested by gently tapping the flasks to dislodge the cells. Cells in suspension were transferred to conical tubes. Additional PBS was added to the flasks to remove the remaining floating cells and residual media and added to the cell suspension in the conical tubes. Detachment of the remaining adherent cells was completed by adding PBS and incubating the flasks at 2-8° C. for approximately 10 minutes. While these cells were incubating, the cell suspension in the conical tubes was centrifuged, and the cell pellet was resuspended in PBS. At the end of the incubation period, the flasks were gently tapped and the contents added to the cell suspension in the conical tubes. The total cell suspension was pelleted and resuspended in PBS, and a sample was removed for cell concentration, cell viability and immunophenotyping. The following four sets of cell markers were examined by flow cytometry: monocyte lineage markers (CD3, CD14, CD19, and CD56), indication of presence of dendritic cells (CD11c), an antigen presenting cell marker (HLA-DR), and a mature dendritic cell marker (CD83). The immature dendritic cell-enriched preparation expressed insignificant levels of lineage markers and CD83, and high levels of CD11c and HLA-DR.

Immature dendritic cells were washed once with OPTI-MEM® I reduced serum medium (GIBCO™) with HEPES buffer, L-glutamine, without phenol red. The dendritic cells were then transfected with amplified tumor RNA by electroporation at a ratio of approximately 2 µg of RNA per 10$^6$ dendritic cells. Electroporation was performed in 4 mm gap cuvettes containing 600 µL of a cell suspension containing 5×10$^7$ cells/ml, at a pulse of 500 V for 500 µs. After electroporation, transfected cells were transferred into T150 flasks (one cuvette per flask) containing StemSpan H2000™ medium (serum free culture medium), supplemented with IL-4 (500 U/ml) and GM-CSF (800 U/ml). Transfected cells were incubated at for 2-3 hours at 37° C., 5% $CO_2$, ≧75% humidity to allow the cells to recover from electroporation.

The immature electroporated dendritic cells were matured in StemSpan H2000™ medium, supplemented with IL-4 (500 U/ml) and GM-CSF (800 U/ml) and a maturation cocktail (IL-1β at 5 ng/ml, IL-6 at 150 ng/ml, TNF-α at 5 ng/ml and $PGE_2$ at 1 µg/ml) at 37° C., 5% $CO_2$, ≧75% humidity for 20-24 hours. All cytokines, as well as $PGE_2$, were reconstituted or diluted (in the case of $PGE_2$) in PBS with 1% HSA. Prior to the dilution step, $PGE_2$ was reconstituted in ethanol. Mature dendritic cells were then rinsed with PBS prior to adding cell dissociation buffer (trypsin free) and then washed three times with PBS to remove the cell dissociation buffer. Samples were collected for cell concentration, viability and immunophenotyping. A comparison of the immunophenotyping of immature and mature dendritic cells is shown in Table 1.

TABLE 1

|  | Donor 39 | Donor 40 | Donor 41 | Donor 42 | Average | S.D. |
| --- | --- | --- | --- | --- | --- | --- |
| Immature DCs |  |  |  |  |  |  |
| % viability (Trypan) | 96.0 | 95.0 | 96.0 | 97.0 | 96.0 | 0.8 |
| % yield (PBMC) | 6.1 | 2.3 | 1.9 | 6.0 | 4.1 | 2.3 |
| IMMUNOPHENOTYPE |  |  |  |  |  |  |
| Gated on small + large cells |  |  |  |  |  |  |
| % CD3+ | 1.2 | 1.4 | 0.8 | 0.9 | 1.1 | 0.3 |
| % CD19+ | 1.9 | 11.7 | 3.5 | 4.8 | 5.5 | 4.3 |
| % CD14+ | 1.4 | 0.3 | 0.3 | 0.0 | 0.5 | 0.6 |
| % CD56+ | 1.0 | 1.1 | 0.8 | 1.0 | 1.0 | 0.1 |
| CD3+CD19+CD14+CD56+ | 5.5 | 14.5 | 5.4 | 6.7 | 8.0 | 4.4 |

TABLE 1-continued

|  | Donor 39 | Donor 40 | Donor 41 | Donor 42 | Average | S.D. |
|---|---|---|---|---|---|---|
| Gated on large cells | | | | | | |
| % CD11c+ | 99.6 | 97.8 | 99.7 | 99.7 | 99.2 | 0.9 |
| % CD80+ | 26.6 | 77.3 | 37.0 | 46.6 | 46.9 | 21.9 |
| % CD83+ | 2.2 | 2.5 | 2.3 | 8.2 | 3.8 | 2.9 |
| % CD86+ | 92.1 | 42.4 | 66.2 | 82.0 | 70.7 | 21.7 |
| % HLA-DR+ | 90.8 | 74.9 | 72.4 | 42.7 | 70.2 | 20.1 |
| Mature DCs | | | | | | |
| Tumor Source | Melanoma | Renal CC | Renal CC | Melanoma | | |
| % viability (Trypan) | 93.0 | 83.0 | 88.0 | 91.0 | 88.8 | 4.3 |
| % yield (PBMC) | 73.0 | 72.0 | 61.0 | 57.3 | 65.8 | 7.9 |
| IMMUNOPHENOTYPE | | | | | | |
| Gated on small + large cells | | | | | | |
| % CD3+ | 1.2 | 1.2 | 0.9 | 1.0 | 1.1 | 0.2 |
| % CD19+ | 2.3 | 11.3 | 2.2 | 5.3 | 5.3 | 4.3 |
| % CD14+ | 1.4 | 0.4 | 0.9 | 0.1 | 0.7 | 0.6 |
| % CD56+ | 1.0 | 1.4 | 2.0 | 0.9 | 1.3 | 0.5 |
| CD3+CD19+CD14+CD56+ | 5.9 | 14.3 | 6.0 | 7.3 | 8.4 | 4.0 |
| Gated on large cells | | | | | | |
| % CD11c+ | 99.6 | 98.9 | 99.4 | 99.6 | 99.4 | 0.3 |
| % CD80+ | 90.8 | 92.8 | 92.9 | 91.8 | 92.1 | 1.0 |
| % CD83+ | 75.0 | 50.8 | 79.2 | 72.9 | 69.5 | 12.7 |
| % CD86+ | 99.4 | 94.2 | 98.8 | 99.1 | 97.9 | 2.5 |
| % HLA-DR+ (MHC class II) | 97.5 | 97.2 | 98.1 | 93.9 | 96.7 | 1.9 |

Transfected mature dendritic cells were suspended in autologous plasma at a final concentration of $2 \times 10^7$ cells/ml. The cells were then diluted 1:1 with a mixture of 80% plasma and 20% DMSO to give a final concentrations of $3 \times 10^6$ or $1 \times 10^7$ cells/ml in 90% plasma with 10% DMSO, then frozen in cryovials using controlled-rate freezing, and stored at $\leq -150°$ C.

Example 2

Dendritic Cell Vaccines Prepared from Day-Old Leukapheresis Product Remain Viable for at Least 2 Hours Post Thaw in 10% DMSO A frozen dendritic cell vaccine prepared as described in Example 1 was thawed at 37° C., and kept at 20-25° C. or at 2-8° C. for 2 hours. Viability was determined immediately post-thaw and at 30 minute intervals for up to two hours. Viability immediately post-thaw at 37° C. was 92%. The results are shown in Table 2, and confirm that the vaccine can be thawed and stored in 10% DMSO for at least two hours.

TABLE 2

|  | Viability (%) | |
|---|---|---|
| Post-thaw time (minutes) | 20-25° C. Post-thaw | 2-8° C. Post-thaw |
| 30 | 91 | 88 |
| 60 | 89 | 86 |
| 90 | 89 | 80 |
| 120 | 87 | 83 |

Example 3

Isolation of Mononuclear Cells from a Patient and Differentiation of Monocytes into Immature Dendritic Cells Peripheral blood mononuclear cells and plasma were collected from a patient or volunteer by leukapheresis at room temperature at a clinical site. The leukapheresis product (PBMCs) and serum were shipped overnight in a temperature controlled container maintained in a temperature range of 6-28° C. The day following leukapheresis, the PBMCs were purified by Ficoll density gradient centrifugation in 50 ml conical tubes at room temperature to separate and concentrate the mononuclear cell fraction that includes monocytes (the dendritic cell precursors) and leukocytes. The mononuclear cells were washed several times in phosphate buffered saline (PBS), and the cell concentration was determined. After the final centrifugation/washing step with PBS, mononuclear cells were resuspended in AIM-V medium and seeded in T150 cm$^2$ flasks at $2.0 \times 10^8$ cells per flask. Monocytes were then selected from the mononuclear cell population by adhesion to sterile tissue culture flasks for one to two hours at 37° C., 5% $CO_2$, $\geq 75$% humidity. Nonadherent and semi-adherent cells were removed by gentle washing with PBS. The remaining adherent cells, which were predominantly monocytes, were cultured in X-VIVO 15 culture medium containing 1000 U/ml GM-CSF and 1000 U/ml IL-4. The cells were incubated for 6 days at 37° C., 5% $CO_2$, $\geq 75$% humidity to allow differentiation of monocytes into immature dendritic cells.

Following in vitro culture, the immature dendritic cell-rich population was harvested by tapping the flasks to dislodge the cells. Cells in suspension were transferred to conical tubes. PBS was added to the flasks to remove the remaining floating cells and residual medium, and then added to the cell suspension in the same conical tubes. Detachment of remaining adherent immature dendritic cells was promoted by incubation in PBS at 2-8° C. At the end of the incubation period, the flasks were tapped and the contents added to the cell suspension in the same conical tubes. The total cell suspension was then pelleted and resuspended in PBS, and a sample was removed to determine the cell concentration.

Immature dendritic cells were washed and resuspended in ViaSpan and transfected with 2 μg antigen-encoding mRNA per $10^6$ dendritic cells. Electroporation was performed in 4 mm gap cuvettes containing 0.4 ml of the cell suspension ($4\times10^7$ cells/ml) at a pulse of 300V, 100Ω and 150 μF. After electroporation, transfected cells were diluted with X-VIVO 15 medium, centrifuged and resuspended in X-VIVO 15 medium (serum free) supplemented with GM-CSF (800 U/ml), IL-4 (500 U/ml), IL-1β (10 ng/ml), IL-6 (150 ng/ml), TNF-α (10 ng/ml) and $PGE_2$ (1 μg/ml). The cells were incubated at 37° C., 5% $CO_2$, ≧75% humidity overnight to mature.

Transfected mature dendritic cells were suspended in heat-inactivated autologous plasma and 10% dextrose, at a final concentration of $4\times10^7$ cells/ml. The cells were then diluted 1:1 with a mixture of 20% DMSO to give a final concentration of $2\times10^7$ cells/ml in heat-inactivated autologous plasma which contains 10% DMSO and 5% dextrose, and then frozen in sterile cryovials at ≦150° C.

Example 4

Physical and Functional Characterization of Dendritic Cells Prepared from Monocytes Incubated Overnight at 6-28° C.

The data in this example supports the functionality and feasibility of producing RNA transfected dendritic cells from day-old apheresis product. Dendritic cells were prepared by the method described in Example 3. The data below shows that dendritic cells can be reproducibly manufactured at the appropriate yield from a single day-old apheresis product and that the resulting cells (1) exhibit a classical mature phenotype, (2) can be efficiently transfected with RNA, and (3) can be cryopreserved with high post-thaw viability.

Immunophenotype of DCs. The mature DCs were extensively characterized by FACS staining for molecular markers that should be present or absent from the final cell preparation. HLA-DR, CD83, CD86, CD80, CD1a, and CD209 should show high expression and CD14, CD56, CD19, and CD3 should show low expression. Table 3 (below) shows the results (mean and standard deviation for percent positive cells) compiled from 11 consecutive runs of producing dendritic cell vaccines from PBMCS obtained from different healthy donors.

TABLE 3

Expression of Cell Surface Markers in DCs produced from Day Old Monocytes

| Marker | % positive cells (Mean) | % positive cells Standard Dev. |
| --- | --- | --- |
| HLA-DR | 99.08 | 1.21 |
| CD83 | 91.46 | 4.97 |
| CD14 | 0.87 | 0.89 |
| CD56 | 6.45 | 6.85 |
| CD19 | 1.57 | 0.71 |
| CD3 | 2.33 | 0.66 |
| CD86 | 98.87 | 1.66 |
| CD80 | 83.73 | 25.50 |
| CD1a | 56.15 | 19.45 |
| CD209 | 95.73 | 4.81 |

These data, along with photomicrographs (not shown) demonstrate that the DCs produced by the methods of the invention conditions exhibit the classical DC phenotype and morphology. Furthermore, the relatively low standard deviations are indicative of the reproducibility of the process.

Yield, phenotype and viability. The dendritic cell methods have been thoroughly tested and shown to reproducibly generate high-quality RNA-transfected mature dendritic cells. Table 4 shows the outcome of 11 vaccine runs using total amplified tumor cell line RNA as the antigen payload and normal donor dendritic cells as the vehicle.

TABLE 4

Summary of release test results for DC vaccine product generated in 11 consistency runs

| Consistency Run | MatDC Phenotype | | | Post Thaw | |
| --- | --- | --- | --- | --- | --- |
| | CD14 | CD83 | HLA-DR | Viability | Doses |
| 1 | 1.5% | 86.6% | 99.7% | 81% | 5 |
| 2 | 0.7% | 95.0% | 100.0% | N/A | 2 |
| 3 | 2.9% | 94.8% | 99.9% | 93% | 22 |
| 4 | 0.3% | 89.6% | 96.1% | 88% | 15 |
| 5 | 2.0% | 81.2% | 97.7% | 64% | 17 |
| 6 | 0.5% | 92.7% | 100.0% | 88% | 34 |
| 7 | 0.1% | 85.8% | 98.7% | 84% | 20 |
| 8 | 0.6% | 95.2% | 99.5% | 85% | 12 |
| 9 | 0.5% | 93.0% | 99.8% | 83% | 18 |
| 10 | 0.3% | 96.4% | 99.8% | 90% | 38 |
| 11 | 0.2% | 95.6% | 98.6% | 88% | 12 |
| Mean ± SD For 11 Runs | 0.9% ± 0.9% | 91.4% ± 5.0% | 99.0% ± 1.2% | 84% ± 8% | 17.7 ± 10.8 |

Matured RNA-transfected DCs express CCR7 and are migratory. In addition to the mature DC markers described above, CCR7 expression, which is critical for lymph node migration of the DCs in vivo, was evaluated. In this study FACS analysis with a CCR7-specific antibody was used to examine thawed RNA-transfected DCs produced using the full-scale GMP process (consistency runs 3, 4, 6, 7, 8, and 10). The results are shown in Table 5 below:

TABLE 5

Percentage of CCR7+ Dendritic Cells

|  | IgG isotype control | CCR7 antibody |
|---|---|---|
| Run #3 | 0.37* | 41.9 |
| Run #4 | 0.12 | 44.6 |
| Run #6 | 0.14 | 42.42 |
| Run #7 | 0.65 | 42.96 |
| Run #8 | 0.17 | 26.94 |
| Run #10 | 0.13 | 32.76 |

*% positive cells

In addition to demonstrating the physical presence of CCR7 on the DCs after maturation, it was demonstrated that DCs also have migratory capacity using the collagen gel matrix spontaneous migration assay, which indicates that the expressed CCR7 is also functional (data not shown).

Figure 2:
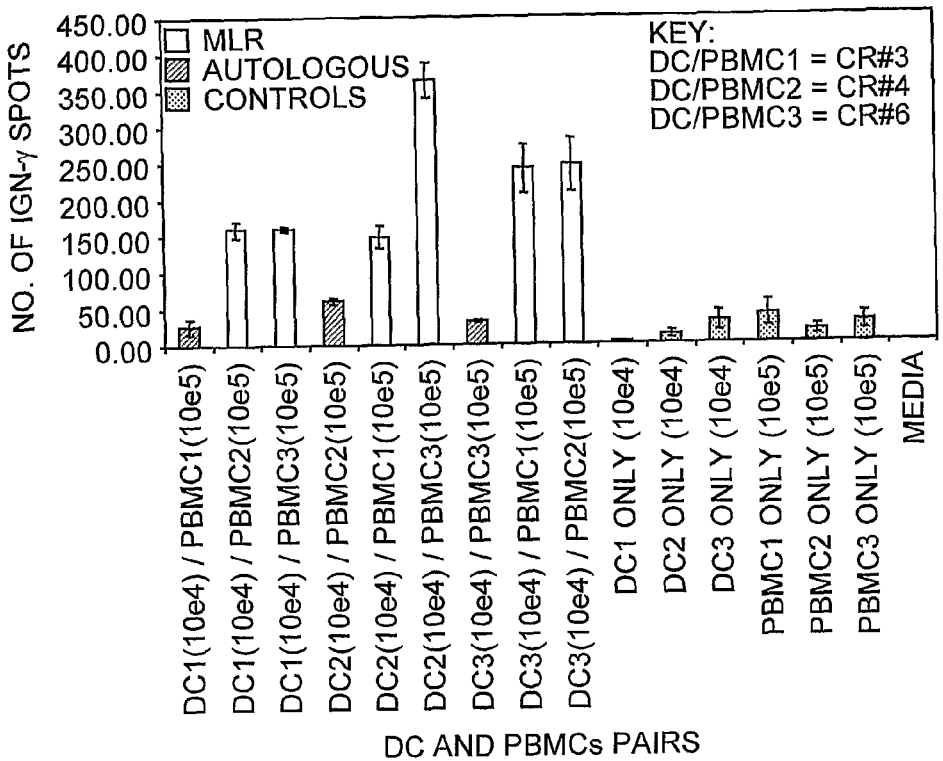
FIG. 2: RNA-transfected DCs provide functional costimulatory support. DCs were tested for the ability to stimulate INF-γ production from PBMC in a mixed lymphocyte (MLR) assay. Thawed DCs manufactured from 3 different donors were paired with previously frozen PBMCs from each donor. All pairwise combinations were tested using ELISPOT (INF-γ) as the readout. Columns 1, 4, and 7 represent DCs paired with autologous PBMCs. Columns 2, 3, 5, 6, 8 and 9 represent DCs paired with non-autologous PBMCs. Columns 10-12 represent DC only controls. Columns 13-14 represent PBMC only controls.

RNA-transfected DCs provide functional costimulatory support. The experiments described above show that the manufactured DCs express all of the critical costimulatory markers, while the experiments below demonstrate that these molecules are functional. To this end, the ability of the DCs to stimulate interferon gamma (IFN-γ) production from PBMCs in an allo mixed lymphocyte (MLR) assay was determined using thawed DCs manufactured from 3 different donors along with previously frozen PBMCs from each donor. The expectation was that DCs would not stimulate INF-γ production from their HLA-matched autologous PBMCs but would do so when mixed with non-autologous PBMCs. All pair wise combinations were tested using ELISPOT (INF-γ) as the readout. The data is presented in FIG. 2. The result of this experiment demonstrates that, as anticipated, only mismatched DC/PBMC combinations elicit INF-γ production, a property which requires expression of functional MHC and costimulatory molecules.

Figure 3:
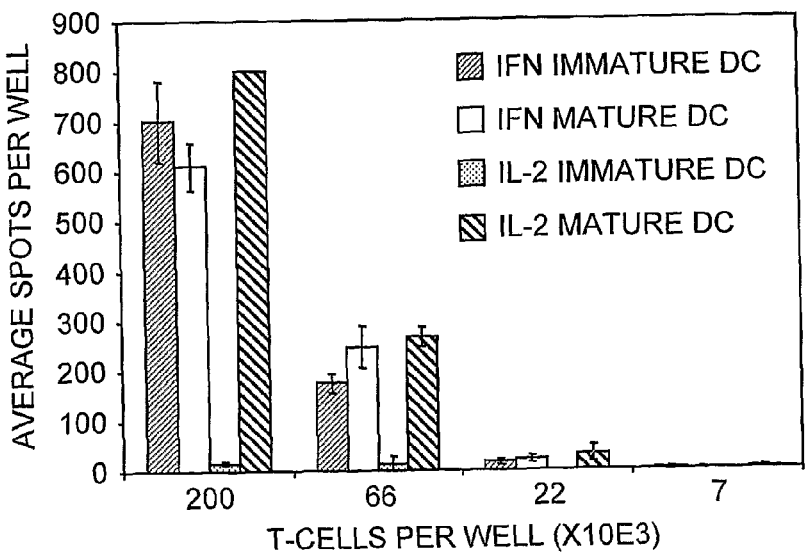
FIG. 3: Cytokine cocktail matured DCs were compared to immature DCs from the same donor in their ability to stimulate Th1 cytokine production from autologous T cells. Both populations of DCs were transfected with RNA encoding Flu matrix protein and used to stimulate Flu-specific memory CTL from autologous PBMCs. The results of the ELISPOT analyses (# spots/well as a function of input PBMC) are shown. Each set of four columns is arranged in the following order: IFNγ production elicited from Flu-specific T memory cells by immature DCs, IFNγ production elicited from Flu-specific T memory cells by mature DCs; IL-2 production elicited from Flu-specific T memory cells by immature DCs; and IL-2 production elicited from Flu-specific T memory cells by mature DCs.

Matured DCs have added functionality. In this experiment, the cytokine cocktail used to mature the DCs post-transfection and pre-freeze contains TNF-α, IL-1β, IL-6, and PGE$_2$. To demonstrate that matured DCs are superior to the immature DCs, the ability of these two populations (from the same donor) to stimulate T$_H$1 cytokine production from autologous T cells. Both populations of DCs were transfected with RNA encoding Flu matrix protein and used to stimulate Flu-specific memory CTL from autologous PBMCs. FIG. 3 below shows the results of the ELISPOT analyses (# spots/well as a function of input PBMC). No statistical difference between immature and mature DCs to elicit INF-γ production from Flu-specific memory T cells was observed. However, only the mature DCs could also elicit IL-2 production from these cells. IL-2 induction is considered to be an important because (1) induced IL-2 secretion sustains autocrine antigen-specific CTL proliferation and (2) low production of INF-γ and IL-2 has recently been shown to correlate with increased mortality risk in HIV patients and in a recent study, lack of secretion of INF-γ or IL-2 has resulted in impaired T cell function and an inability to maintain central memory responses. For simplicity, the negative controls were not graphed. The average number of spots observed from the PBMC alone (i.e., no DCs) was 9.7 (INF-γ) and 1.3 (IL-2). This experiment was repeated with vaccines made from the PBMCs of 3 independent donors and the results were qualitatively identical. Accordingly, the mature DCs have added and superior functionality compared to the immature DCs.

Figure 4:
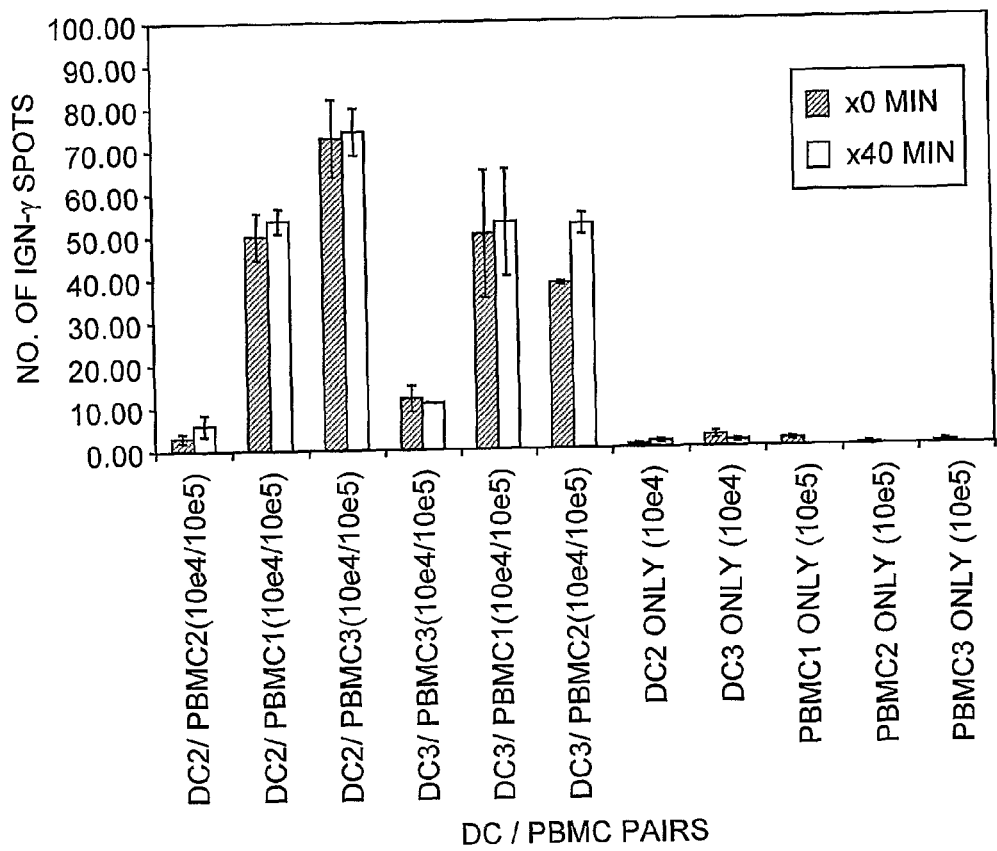
FIG. 4: Two vials each of two RNA-loaded dendritic cells preparations made from day-old PBMCs obtained from 2 different healthy donors were thawed. One vial from each donor was immediately tested in an allo MLR assay while the second vial from each preparation was allowed remain at room temperature for 40 minutes before being assayed by the same method. The PBMCs used in this experiment included autologous cells from each donor as well as a third sample of PBMCs from a donor unrelated to either. The readout for this assay was ELISPOT (INF-γ).

Post-thaw RNA-transfected DCs are stable. While clinical protocols may specify immediate injection of the dendritic cell vaccine upon thawing, unforeseen circumstances could arise that might delay administration. To demonstrate that the DCs would remain viable and functional if thawed but not immediately injected, the following experiment was performed. Two vials each of 2 dendritic cell preparations corresponding to 2 different healthy donors were thawed. One vial from each donor was immediately tested in an allo MLR assay while the second vial from each preparation was allowed remain at room temperature for 40 minutes before being assayed by the same method. The PBMCs used in this experiment included autologous cells from each donor as well as a third sample of PBMCs from a donor unrelated to either. The readout for this assay was ELISPOT (INF-γ). The result of this experiment is shown in FIG. 4 and indicates that there is no appreciable difference in function between the DCs assayed immediately upon thawing and those that remained at room temperature for 40 minutes. In addition to this functional assay, cell viability post-thaw and 40 minutes post-thaw by trypan dye exclusion was determined and identical results were obtained (data not shown).

Figure 5:
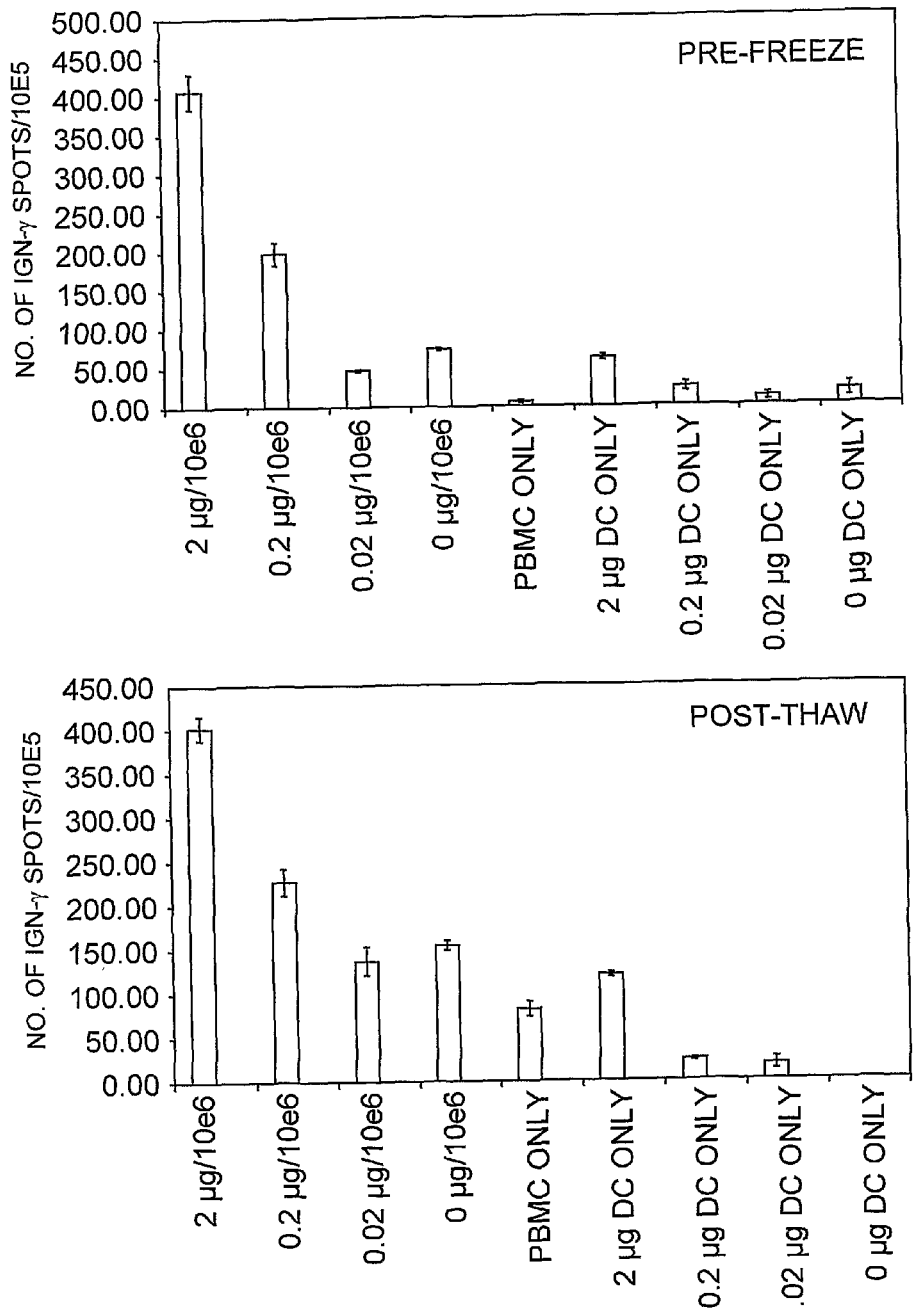
FIG. 5: The functionality of DCs pre-freeze versus post-thaw was assessed by the ability of the DCs to stimulate a memory Flu-specific response from autologous PBMC as a function of decreasing Flu mRNA concentration used for transfection. The assay readout was ELISPOT (INF-γ).

Freeze-thaw does not affect DC function. To assess whether DC function is adversely affected by the freeze-thaw process, the functionality of DCs pre-freeze and post-thaw was compared. Functionality was assessed by the ability of the DCs to stimulate a memory Flu-specific response from autologous PBMC as a function of decreasing Flu mRNA concentration used for transfection. The assay readout was ELISPOT (INF-γ). Results are shown in FIG. 5 below and indicate that the freeze-thaw process has no effect on the functionality of the DCs in this assay. A constant amount of GFP mRNA (0.5 µg) was mixed in to monitor transfection efficiencies. Post-thaw samples were thawed after being frozen for 24 hours.

Figure 6:
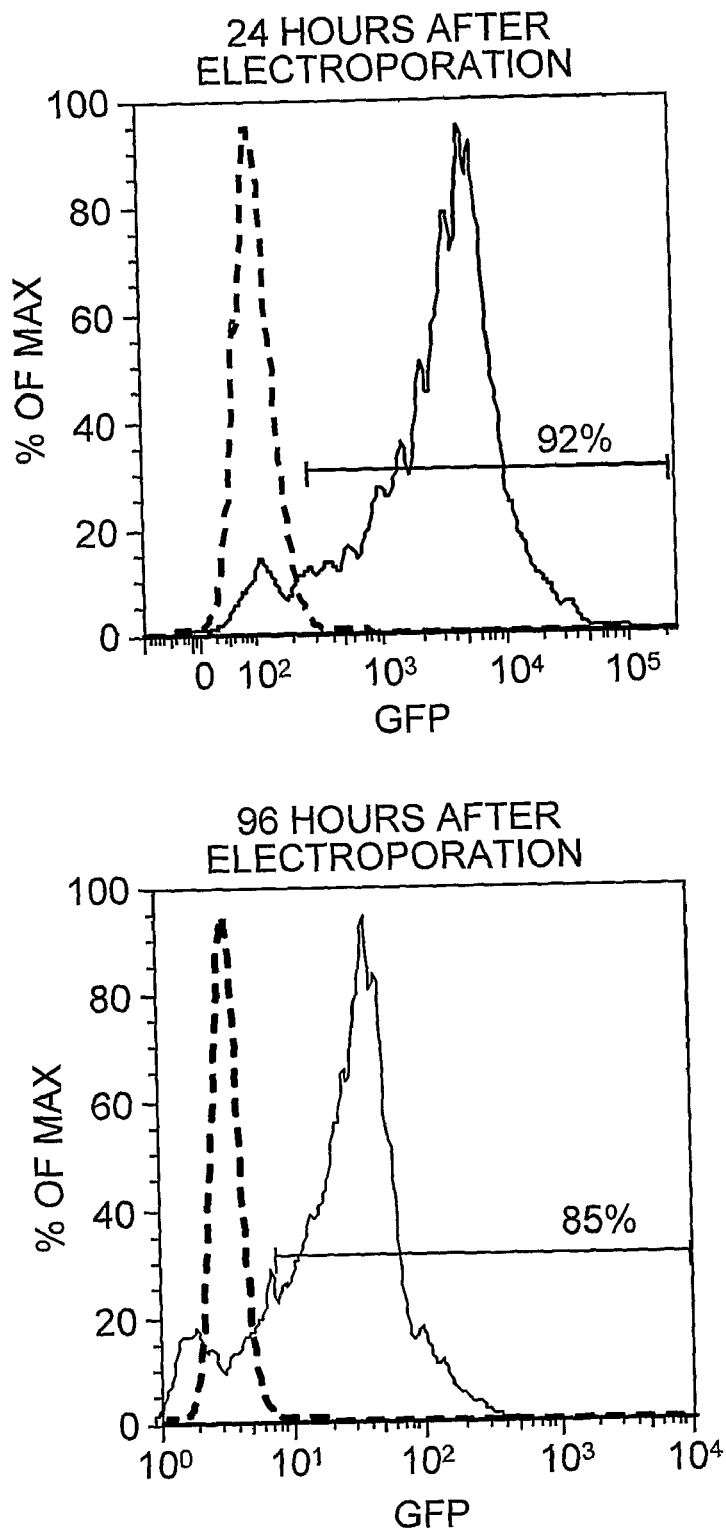
FIG. 6: Flow cytometry assessment of GFP expression by DCs following electroporation with RNA encoding GFP. Untransfected (dashed line).

Protein expression after electroporation of DCs with mRNA. As a first step, we assessed whether transfection of DCs with mRNA leads to the proper expression of the mRNA-encoded protein. For preparation of DCs, PBMCs (either fresh or frozen) obtained by leukapheresis from healthy volunteers were enriched for monocytes by adherence to plastic flask following a 2-hour incubation in vitro. After washing, adherent cells were cultured for six days in X-VIVO 15 medium supplemented with recombinant granulocyte/macrophage-colony stimulating factor (rGM-CSF) and interleukin-4 (rIL-4) to generate immature DCs (iDCs). iDCs were then electroporated (300V, 150 µF, 100Ω) with RNA encoding viral or control proteins and induced to mature for 24 hours in X-VIVO 15 medium supplemented with IL-1β, IL-4, IL-6, GM-CSF, TNF-α and prostaglandin E$_2$ (PGE$_2$). To test the expression of protein following transfection, DCs were electroporated with RNA encoding the Green Fluorescent Protein (GFP) and expression was measured by flow cytometry. As shown in FIG. 6, a large fraction of mature DCs produced from day-old monocytes expresses high levels of GFP up to four days after transfection, confirming that this method is efficient at promoting long-term protein expression in DCs.

Next, the ability of autologous DCs transfected by electroporation with mRNA encoding the CMV pp 65 protein to induce CD4 and CD8 T cell responses in PBMCs from CMV-infected individuals was determined. CMV-infected subjects were identified by stimulating PBMCs from several blood donors with well-defined immunodominant peptides derived from the pp 65 protein and measuring IL-2/IFN-γ secretion as well as cell proliferation in both CD4 and CD8 T cells. Individuals in which positive CMV-specific T cell responses were detected and who agreed to undergo leukapheresis after informed consent were selected for further studies.

Figure 7:
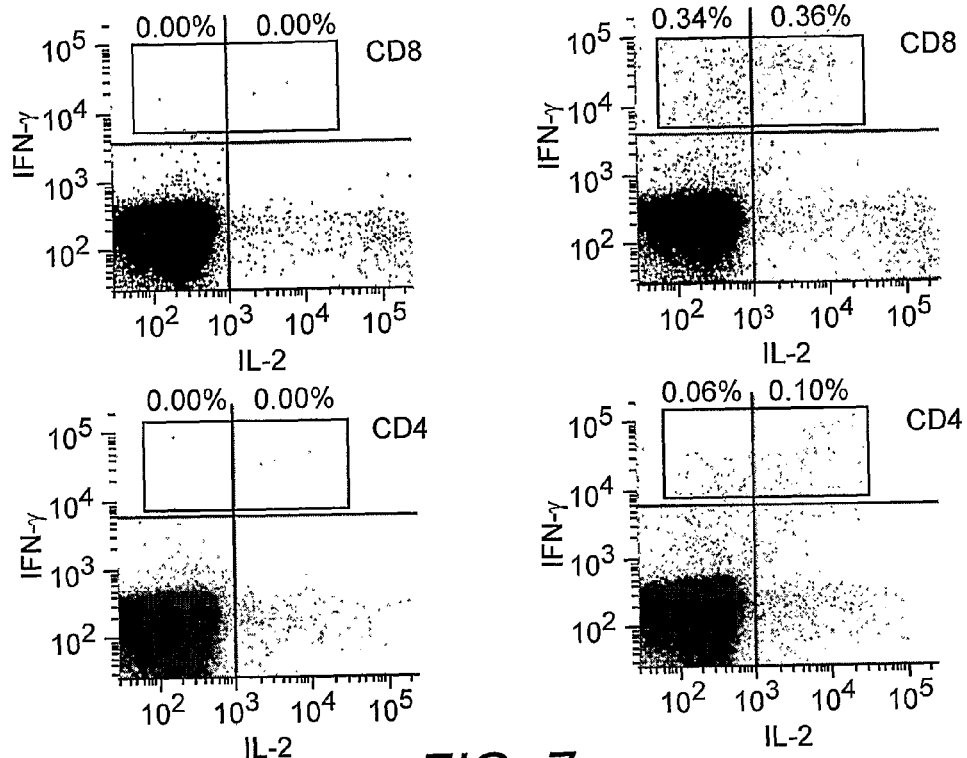
FIG. 7: Intracellular cytokine staining: IL-2/IFN-γ on CD4 and CD8 T cells following stimulation with DC transfected with RNA encoding GFP (negative control, left panels) or CMV pp 65 (right panels).
Figure 8:
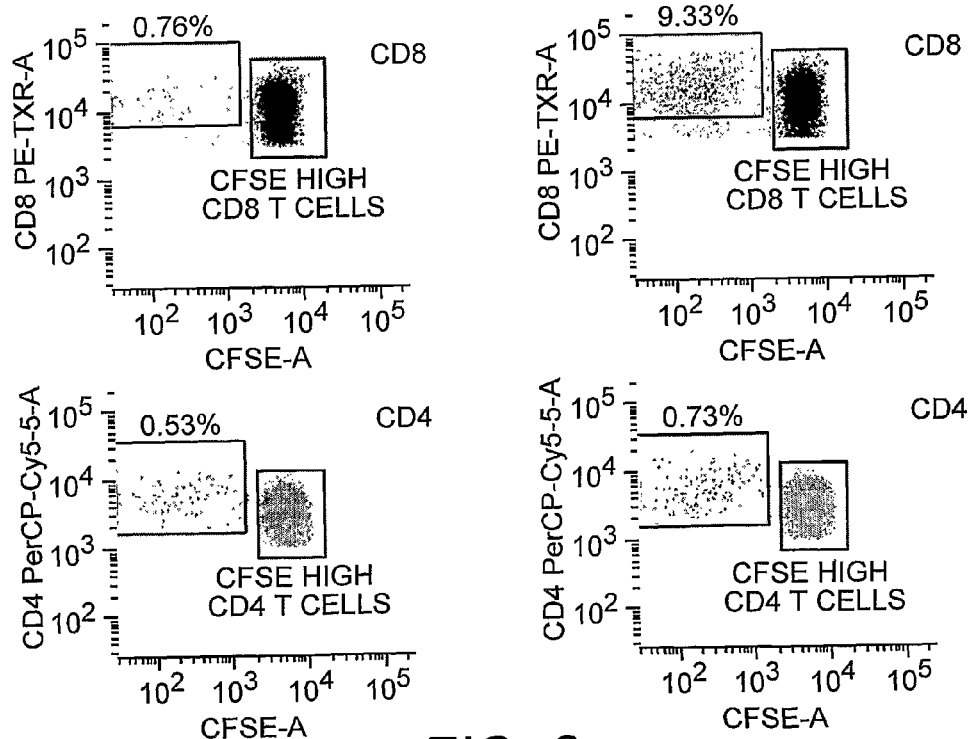
FIG. 8: CSFE dilution in CD4 and CD8 T cells following stimulation with DCs transfected with RNA encoding GFP (negative control, left panels) or CMV pp 65 (right panels).

DCs from these individuals were prepared as described above. Mature DCs transfected with RNA encoding the CMV pp 65 protein were then incubated for 16 hours (ICS) or 6 days (proliferation) with autologous PBMCs at a 1/40 ratio. After stimulation, IL-2 and IFN-γ secretion (FIG. 7) and proliferation (FIG. 8) of CMV-specific CD4 and CD8 T cells was assessed by flow cytometry. DCs electroporated with CMV pp 65 RNA selectively induced high IFN-γ and IL-2 expression as well as proliferation of CD8 T cells from CMV-infected subjects. However, this protocol induces minimal CD4 T cell activation, as shown by the low level of cytokine secretion and proliferation detected in CD4 T cells (FIGS. 7 and 8, lower panels).

Example 5

Comparison of Differentiation of Monocytes into Dendritic Cells Using 500 U/ml or 1000 U/ml IL-4

PBMC's from day-old leukapheresis maintained at a temperature of 6-28° C. were washed and seeded @~2×10$^8$/flask in AIM-V media for a 2 hour adherence step. After 2 hours, non-adherent cells were removed, and adherent cells were washed and resuspended in X-VIVO 15 supplemented with 1000 U/ml GM-CSF and either 500 U/ml or 1000 U/ml IL-4; incubated @ 37° C. for 6 days. In addition, for culture in X-VIVO 15 supplemented with 1000 U/ml GM-CSF and 500 U/ml IL-4, the effect of changing the medium on day 3 was compared to culture for 6 days without a change in medium. Specifically, on day 3, media was removed along with cells in suspension; the flask was gently washed with X-VIVO media to harvest loosely adherent cells; and the media and wash were centrifuged @ 1300 rpm for 8 minutes to pellet cells. The cells were resuspended in fresh X-VIVO 15 medium supplemented with 1000 U/ml GM-CSF and 500 U/ml IL-4; the media and cells added back into flasks still containing the adherent cells; and the flasks were incubated @ 37° C. for a further three days.

Figure 9:
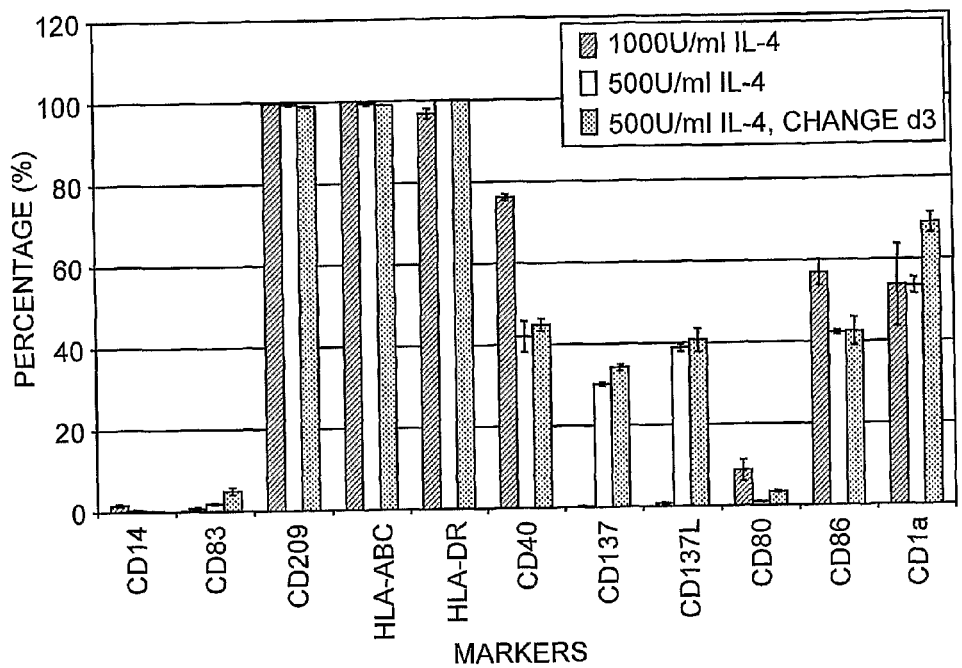
FIG. 9: Phenotypes of day 6 immature dendritic cells (iDCs) prepared from day old leukapheresis product.
Figure 10:
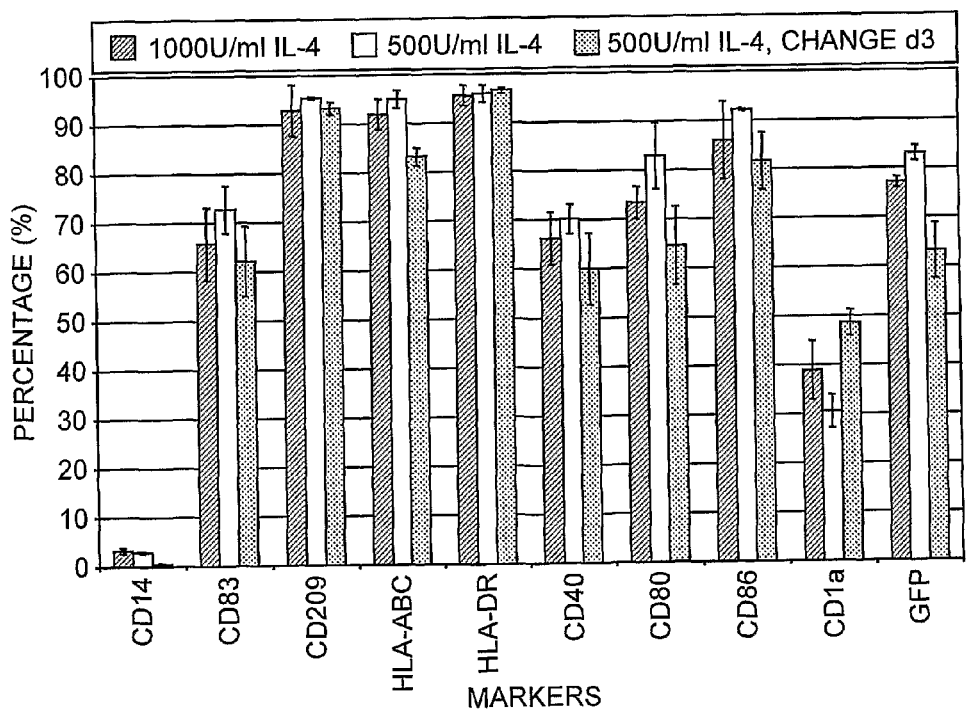
FIG. 10: Phenotypes of day 7 mature dendritic cells (mDCs) prepared from day old leukapheresis product.

All flasks were harvested individually for electroporation. Day 6 DCs were transfected with 2 μg GFP mRNA per 10$^6$ cells (20 μg GFP mRNA per 5×10$^6$ cells), resuspended in X-VIVO 15 and seeded at 1×10$^6$/ml; supplemented with 800 U/ml GM-CSF and 500 U/ml IL-4 and matured with cytokine cocktail (TNFα-10 ng/ml; IL-1β-10 ng/ml; IL-6-100 ng/ml; PGE$_2$-1 μg/ml). The DC's were incubated overnight @ 37° C.; 5% CO$_2$. Phenotyping was undertaken on immature DC's on day 6 (immature DC; FIG. 9) and 24 hours post transfection (mature DC; FIG. 10). The yield (% Rec) and viability (% V) for each culture condition immediately post transfection and at 24 hour post transfection is shown in Tables 6A-C.

TABLE 6A

1000 U/ml IL-4

|  | DC yield day 6 | % Rec | % V | DC per Tn | DC @0 hr post Tn | % Rec | % V | DC @24 hr post Tn | % Rec | % V |
|---|---|---|---|---|---|---|---|---|---|---|
| F1 | 3.76 × 10$^7$ | 21 | 97 | 5 × 10$^6$ | 2.08 × 10$^6$ | 42 | 81 | 1.03 × 10$^6$ | 21 | 84 |
| F2 | 3.88 × 10$^7$ | 22 | 94 | 5 × 10$^6$ | 2.41 × 10$^6$ | 48 | 84 | 8.80 × 10$^5$ | 18 | 91 |
| F3 | 4.44 × 10$^7$ | 25 | 96 | 5 × 10$^6$ | 2.06 × 10$^6$ | 41 | 83 | 8.10 × 10$^5$ | 16 | 84 |
| pooled |  |  |  | 2 × 10$^7$ | 1.04 × 10$^7$ | 52 | 80 | 7.40 × 10$^6$ | 37 | 94 |
| pooled |  |  |  | 2 × 10$^7$ | 1.11 × 10$^7$ | 56 | 93 | 7.50 × 10$^6$ | 38 | 93 |

TABLE 6B

500 U/ml IL-4

|  | DC yield day 6 | % Rec | % V | DC per Tn | DC @0 hr post Tn | % Rec | % V | DC @24 hr post Tn | % Rec | % V |
|---|---|---|---|---|---|---|---|---|---|---|
| F1 | 4.16 × 10$^7$ | 23 | 97 | 5 × 10$^6$ | 2.81 × 10$^6$ | 56 | 77 | 1.19 × 10$^6$ | 24 | 87 |
| F2 | 4.23 × 10$^7$ | 24 | 97 | 5 × 10$^6$ | 2.43 × 10$^6$ | 49 | 84 | 1.32 × 10$^6$ | 26 | 85 |
| F3 | 3.87 × 10$^7$ | 22 | 96 | 5 × 10$^6$ | 3.26 × 10$^6$ | 65 | 84 | 1.52 × 10$^6$ | 30 | 89 |

TABLE 6C

500 U/ml IL-4, change medium on day 3

|  | DC yield day 6 | % Rec | % V | DC per Tn | DC @0 hr post Tn | % Rec | % V | DC @24 hr post Tn | % Rec | % V |
|---|---|---|---|---|---|---|---|---|---|---|
| F1 | 2.81 × 10$^7$ | 16 | 94 | 5 × 10$^6$ | 1.79 × 10$^6$ | 36 | 62 | 9.6 × 10$^5$ | 19 | 82 |
| F2 | 2.82 × 10$^7$ | 16 | 93 | 5 × 10$^6$ | 2.37 × 10$^6$ | 47 | 69 | 9.0 × 10$^5$ | 18 | 83 |
| F3 | 2.06 × 10$^7$ | 11 | 85 | 5 × 10$^6$ | 2.15 × 10$^6$ | 43 | 71 | 1.07 × 10$^6$ | 21 | 84 |

Example 6

Enrichment of Monocytes by Elutriation and Differentiation into Immature and Mature DCs Elutriation, also known as counter-flow centrifugation, was performed on the Elutra™ Cell Separation System (Gambro BCT, Lakewood, Colo.) as an automated method to isolate monocytes from a day old leukapheresis, which had been shipped to the manufacturing facility from a collection site by overnight delivery in a temperature controlled (6-28° C.) container. Elutriation buffer was prepared by adding 1000 mL of 5% Human Albumin Serum (HSA, Baxter Healthcare, Westlake, Calif.) to a 4 L bag of Hank's Balanced Salts Solution (HBSS, Cambrex Bio Science, Walkersville, Md.). This elutriation buffer was added to the day old pheresis product in a volume equal to that of the pheresis. The Elutra™ Cell Separation System (Gambro BCT, Lakewood, Colo.) was primed with elutriation buffer and the pheresis product was loaded. After the elutriation procedure was performed, monocytes were collected from the rotor off fraction. The monocytes were stored frozen.

Frozen elutriated monocytes were thawed, and then differentiated at 1 million cells/mL in X-VIVO 15 (Cambrex Bioscience, Walkersville, Md.) with 800 U/mL GM-CSF (Berlex Laboratories, Richmond, Calif.) and 500 U/mL IL-4 (R&D Systems, Minneapolis, Minn.) in flasks for 5 days to produce immature dendritic cells (iDC). The iDC were harvested, and antigen loaded with amplified RCC tumor RNA using electroporation. Cells were cultured with 800 U/ml GM-CSF, 500 U/ml IL-4 and maturation cytokines (TNF-α, IL-1β, IL-6, and $PGE_2$) and harvested after 24 hours of culture. Cell count and viability for the mature dendritic cells (mDC) were determined using Trypan blue exclusion by the ViCell (Beckman Coulter Inc., Fullerton, Calif.). The resulting mDC were phenotyped. The cells cultured in flasks were 99% CD83+ and 0.2% CD14+. The yield of mDC was 34% of the CD14+ cells cultured in flasks.

Example 7

Comparison of Expression of Co-Stimulatory Molecules in DC Prepared from Fresh vs. Day-Old Leukapheresis Peripheral blood was collected from 3 healthy human donors on three separate days by leukapheresis and transported to the University of Montreal within 30 minutes post collection. Twenty mL of the leukapheresis was removed and autologous plasma was prepared by centrifugation. The leukapheresis volume was divided into two equal parts. One part was processed immediately to generate "fresh" monocytes while the second part was stored as 20 mL aliquots in five 50 mL conical tubes to generate cells from a "day old pheresis". The tubes were placed in a plastic container within a box that was stored tilted on a rocking platform between 16-20° C. for 24 hours. Following the incubation period, the PBMCs were separated using Ficoll density gradient.

A mononuclear cell fraction that includes the dendritic cell precursors (monocytes) was separated from both fresh and day old pheresis using a Ficoll density gradient. The Leukapheresis was layered onto Ficoll in 50 mL conical tubes and tubes were centrifuged (800×g) for 20 minutes at room temperature. Cells were washed four times with phosphate buffered saline (PBS), and counted to determine cell concentration and cell viability. To obtain a highly purified monocyte population, the mononuclear fraction was further purified using CD14 microbeads (Miltenyi). $1 \times 10^9$ cells were resuspended in 8 mL of buffer containing PBS, 0.5% BSA, and 2 mM EDTA (Miltenyi buffer). 2 mL of CD14 microbeads were added to each 50 mL tube containing the $1 \times 10^9$ cells and incubated at 4° C. for 15 minutes. The cells were washed in 100 mL of the same buffer, centrifuged at 300×g and resuspended in 20 mL of Miltenyi buffer. The cell suspension was applied to four LS columns situated under magnetic field (Miltenyi Quadromax™). Following application of the cells using gravity flow, the columns were washed three times with 3 mL of Miltenyi buffer. The monocytes were eluted twice in the absence of a magnetic field with 5 mL of Miltenyi buffer and centrifuged at 300×g for 10 minutes. Purity of both the eluate and flow through fractions were determined with flow cytometry using antibodies specific for CD3, CD19, CD16, CD56, CD14, and CD209. The eluate fraction contained 88-98% monocytes and less than 2% small cells. The nonadherent fractions contained only a small percentage (2%) of monocytes. Total RNA was extracted from a portion of the purified monocytes (50 million) at this time.

To prepare mature differentiated DCs, 50 million monocytes were seeded into T150 $cm^2$ flasks in X-VIVO medium containing IL-4 and GM-CSF at 37° C. for five days. A cytokine cocktail (TIP) containing tumour necrosis factor, interferon gamma, and prostaglandin E2 was added to the cells on day five. Cells were harvested on day six of culture and at this time were termed "TIP-DCs". The dendritic cell-rich population was harvested by gently tapping the flasks to dislodge the cells, additional phosphate buffered saline (PBS) washes and detachment of the remaining adherent cells by incubating in PBS and at 2-8° C. for approximately 10 minutes. The total cell suspension was pelleted and resuspended in PBS, and analyzed for cell concentration, cell viability and immunophenotyping. The following sets of cell markers were examined by flow cytometry: monocyte lineage markers (CD3, CD14, CD19, CD16, and CD56), indication of presence of dendritic cells (CD11c, CD1a, and CD209), an antigen presenting cell marker (HLA-II), markers of migration (CD38 and CCR7) and markers for mature dendritic cells (CD83 and CD86).

20 million TIP-DCs were resuspended in 600 μl of ViaSpan™ and electroporated with CD40L RNA at a ratio of 4 μg of RNA per one million dendritic cells. Electroporation was performed in 4 mm gap cuvettes, at a pulse of 300V for 300 μs. After electroporation, cells were transferred into T75 flasks (one cuvette per flask) containing X-VIVO medium (serum free culture medium), supplemented with IL-4 and GM-CSF. Transfected cells were incubated at for 4 hours at 37° C., 5% $CO_2$, ≧75% humidity to allow the cells to recover from electroporation. After this cells were further matured and termed "PME-CD40L DCs". RNA was isolated from a portion of the PME-CD40L DCs generated.

PME-CD40L DCs were frozen in 90% autologous plasma with 10% DMSO, in cryovials using controlled-rate freezing, and stored at ≦−85° C. A frozen dendritic cell vaccine prepared as described above was thawed at 37° C., and kept at 20-25° C. for 30 minutes. Viability was determined immediately post-thaw and at 10 minute intervals up to 30 minutes. Post Thaw PME-CD40L DCs were analyzed by flow cytometry using antibodies specific for monocyte lineage markers (CD14), dendritic cell markers (CD11c, CD1a, and CD209), an antigen presenting cell marker (HLA-II), markers of migration (CD38 and CCR7) and markers for mature dendritic cells (CD80, CD83 and CD86).

Results
Generation of Monocytes

The data from the three donors demonstrates that positive selection using CD14 bead results in 88-98% pure population of monocytes (Table 7). The maximum amount of small cell contamination is 2% (Table 7). The nonadherent (flow through) fraction contained up to 2% of monocytes (large cells) in all three donors (data not shown). Therefore, there is no significant loss of monocytes in the nonadherent fraction. The small cell population contamination present in the eluate is composed primarily of T cells as evident from high CD3 expression and lower CD19, 16 or 56 markers expression (data not shown). There were no visible differences in expression of CD83, CD86, CD11C, HLA-I, or HLA-II markers in the eluate fraction between fresh and day old leukapheresis.

TABLE 7

Monocyte Summary

| Donor | Monocytes | Fraction | % Large cells | % Small cells | % CD14+ |
|---|---|---|---|---|---|
| 1 | Fresh | Eluate | 97-98 | <1-1.5 | 99 |
| 1 | Day old | Eluate | 88-89 | 0.8-1.5 | 99 |
| 2 | Fresh | Eluate | 98-99 | 0.9-1.4 | 99 |
| 2 | Day old | Eluate | 94-98 | 1-2 | 98 |
| 3 | Fresh | Eluate | 97-98 | <1 | 99 |
| 3 | Day old | Eluate | 89-90 | <1 | 97 |

TIP-DCs

Monocytes were very pure initially (90%), and the purity was further improved during the differentiation process as the percentage of large cells in the TIP-DCs from all three donors was 98-99% and, thus, the percentage of small cells was less than 2% (data not shown). Analysis of the phenotype of TIP-DCs with flow cytometry revealed there was a difference in the expression of CD83 between TIP-DCs generated from fresh and day old leukapheresis. The percentage of positive cells refers to the number of cells positive for a marker under investigation. The percentage of DCs expressing the surface maturation marker CD83 was lower in TIP-DCs from all 3 donors prepared from fresh leukapheresis than those prepared from day old leukapheresis (Table 8). There were no other differences in any other markers from the TIP-DCs generated from fresh and day old leukapheresis.

TABLE 8

TIP-DC summary

| Donor | Leukapheresis | % CD83+ | % CD86+ |
|---|---|---|---|
| 1 | Fresh | 26 | 90 |
|   | Day old | 59 | 81 |
| 2 | Fresh | 40 | 74 |
|   | Day old | 51 | 85 |
| 3 | Fresh | 57 | 98 |
|   | Day old | 87 | 98 |

PME-CD40L DCs
4 Hours Post Transfection

The DCs post-transfection (PME-CD40L DCs) were analyzed for expression of CD154 (CD40L) four hours after transfection. PME-CD40L DCs from day old leukapheresis expressed more CD40L in donors 1 and 2 four hours after transfection than PME-CD40L DCs generated from fresh leukapheresis (Table 9). There was also a difference in the mean fluorescence intensity (MFI) of CD40L between the PME-CD40L DCs generated from fresh and day old pheresis in donors one and two (Table 9).

Post-Thaw PME-CD40L DCs

PME-CD40L DCs were analyzed for expression of a variety of DC markers after thawing. There were differences in the phenotype of the post thaw PME-CD40L DCs generated from fresh versus day old leukapheresis. The mean fluorescence intensity of CD40L expression in PME-CD40L DCs prepared from fresh leukapheresis was lower than DCs prepared from day old Leukapheresis (Table 9).

There was also a trend suggesting that, in two donors the transfection efficiency (of percent positive of CD40L expression) is lower in DCs generated from fresh leukapheresis (Table 9).

TABLE 9

Summary of CD154 Expression in PME-CD40L DC

| Donor | Leukapheresis | PME-CD40L DC | % CD154+ | CD154 MFI |
|---|---|---|---|---|
| 1 | Fresh | 4 hrs post electroporation | 35 | 26 |
|   | Day Old | 4 hrs post electroporation | 63 | 51 |
| 2 | Fresh | 4 hrs post electroporation | 40 | 41 |
|   | Day Old | 4 hrs post electroporation | 50 | 60 |
| 3 | Fresh | 4 hrs post electroporation | 58 | 61 |
|   | Day Old | 4 hrs post electroporation | 52 | 35 |
| 1 | Fresh | Post Thaw | 21 | 31 |
|   | Day Old | Post Thaw | 38 | 50 |
| 2 | Fresh | Post-Thaw | 16 | 39 |
|   | Day Old | Post-Thaw | 30 | 44 |
| 3 | Fresh | Post-Thaw | 60 | 56 |
|   | Day Old | Post-Thaw | 56 | 64 |

Percent positive cells measured by flow cytometry revealed that, in two out of three cases, more cells are stained positive with CD83 antibodies in dendritic cells generated from the day old portion of the leukapheresis (Table 10).

TABLE 10

Phenotype of Post Thaw PME-CD40L DC

| Donor | Leukapheresis | % CD83+ | % CD86+ | % CD80+ |
|---|---|---|---|---|
| 1 | Fresh | 50 | 97 | 95 |
|   | Day old | 86 | 99 | 99 |
| 2 | Fresh | 57 | 97 | 98 |
|   | Day old | 71 | 99 | 94 |
| 3 | Fresh | 90 | 98 | 97 |
|   | Day old | 89 | 99 | 97 |

While the difference in percent positive cells for CD80, CD83, and CD86 is not always higher in the DC generated from day old leukapheresis (Donor 3, Table 10), the mean fluorescent intensity of cells generated from day old leukapheresis stained with specific antibodies is higher in all donors (Table 11). In addition to CD80, CD86, and CD83, HLA-I and HLA-II exhibited the same result (Table 11). The mean fluorescent intensity signal correlates with a higher protein level expression per cell and expression of CD80, CD83, CD86, HLA-I and HLA-II molecules is upregulated in a mature DC. Therefore the phenotype of these cells reflects a more mature status of dendritic cells obtained from day old portion in all three donors. These changes reflect the maturation status of the DC. Taken together data obtained with measure of percent positive cells as well as mean fluorescent intensity allows us to conclude that cells generated from day old portion of a leukapheresis exhibit a more mature phenotype.

TABLE 11

MFI of Post Thaw PME-CD40L DCs

| Donor | Leukapheresis | CD83 MFI | CD86 MFI | CD80 MFI | HLA-I MFI | HLA-II MFI |
|---|---|---|---|---|---|---|
| 1 | Fresh | 55 | 97 | 48 | 330 | 145 |
|   | Day old | 73 | 282 | 71 | 904 | 338 |
| 2 | Fresh | 43 | 66 | 47 | 249 | 115 |
|   | Day old | 55 | 123 | 55 | 383 | 214 |
| 3 | Fresh | 27 | 104 | 38 | 630 | 175 |
|   | Day old | 53 | 219 | 57 | 974 | 182 |

Example 8

Microarray Analysis of Gene Expression in Fresh vs. Day Old Monocytes and Dendritic Cells Prepared Therefrom The RNA samples from fresh monocytes and day old monocytes (monocytes which had been incubated at 16-20° C. for 24 hours following leukapheresis), and RNA from DCs prepared from fresh and day old monocytes, as described in Example 8, were applied to the Human Genome U133 Plus 2.0 Array (Affymetrix, Santa Clara, Calif.) according to the manufacture's instruction (Genechip® Expression Analysis Technical Manual, 2004). Briefly, three micrograms of total RNA spiked with Genechip® Poly-A RNA Control Kit (Affymetrix, Santa Clara, Calif.) was converted to first-strand cDNA using SuperScript™ II reverse transcriptase. Second-strand cDNA synthesis was followed by in vitro transcription for linear amplification of each transcript and incorporation of biotinylated CTP and UTP. The cRNA products were fragmented to around 100 nucleotides, and hybridized for 16 hours to the microarrays. The microarrays were then washed at low (6×SSPE) and high (100 mM MES, 0.1 M NaCl) stringency and stained with streptavidin-phycoerythrin.

Fluorescence was amplified by adding biotinylated anti-streptavidin and an additional aliquot of streptavidin-phycoerythrin stain. The GeneChip® Scanner 3000 (Affymetrix, Santa Clara, Calif.) was used to collect fluorescence signal at 3 um resolution after excitation at 570 nm. The average signal from two sequential scans was calculated for each microarray feature. Scanned images were analyzed with Genechip® Operating Software v1.1 (Affymetrix, Santa Clara, Calif.). High linear correlation ($R^2$>0.95) of 4 control RNAs included in Poly-A RNA Control Kit (Affymetrix, Santa Clara, Calif.) was confirmed to guarantee the success of the labeling process.

All profile data were imported into the computer program Genespring and was normalized according to sample type (ie monocyte samples to monocyte and dendritic samples to dendritic). Three steps were performed in the normalization step and were according to the standard method suggested by Genespring for Affymetrix arrays.

4) data transformation (all values less than 0.01 were set to 0.01)
5) Normalization to the $50^{th}$ percentile.
6) Normalization to the median.

The data was first filtered for flags with missing spots. The data was then analyzed with a one way anova without random prediction models with a confidence level ranging from p. 05 or p. 1. The list of filtered genes generated was then analyzed for either fold changes, level of expression, or confidence. This was performed using the samples as averages or as individual samples. Level of expression between fresh and day monocytes or dendritic cells were compared prior to or after an anova. The lists of genes were compared to one another and those overlapping in several lists were chosen for their reliability. Genes with altered steady state RNA levels in dendritic cells prepared from day old monocytes versus dendritic cell prepared from fresh monocytes are listed in Table 12A. Descriptions of these genes are listed in Table 12B. Genes with altered steady state RNA levels in day old monocytes versus fresh monocytes are listed in Table 13A. Descriptions of these genes are listed in Table 13B. These results demonstrate that fresh monocytes are phenotypically different from day old monocytes, and that dendritic cells prepared from fresh monocytes are phenotypically different from dendritic cells prepared from day old monocytes.

TABLE 12A

Genes with Altered Steady State RNA Levels in Dendritic Cells prepared from Day Old Monocytes as compared to Dendritic Cells Prepared from Fresh Monocytes

| Gene Symbol | Affymetrix Identifier | NCBI | Unigene | Fold | P value | Change in Day Old |
|---|---|---|---|---|---|---|
| ALOX15 | 207328_at | NM_001140 | Hs.73809 | 5.8 | 0.0699 | Decrease |
|  | 1558517_s_at | AK094804 | Hs.24181 | 5.5 | 0.0957 | Decrease |
| KRT17; PC; K17; PC2; PCHC1 | 212236_x_at | NM_000422 | Hs.2785 | 5 | 0.0759 | Decrease |
| KCNJ2 | 231513_at, 206765_at | NM_000891 | Hs.1547 | 4.5 | 0.0507 | Decrease |
| YWHAZ | 214848_at | NM_003406, NM_145690 | Hs.492407 | 4.3 | 0.0581 | Decrease |
| IL1B | 205067_at, 39402_at | NM_000576 | Hs.126256 | 3.7 | 0.0752 | Decrease |
| PTX3 | 206157_at | NM_002852 | Hs.127657 | 3.5 | 0.0408 | Decrease |
| FYN | 216033_s_at, 210105_s_at | NM_002037, NM_153047, NM_153048 | Hs.390567 | 3.5 | 0.0724 | Decrease |
| GALNT3 | 203397_s_at | NM_004482 | Hs.170986 | 3.3 | 0.0295 | Decrease |
| FLJ20073 | 219691_at | NM_017654 | Hs.65641 | 3 | 0.0262 | Decrease |
| CDK6 | 243808_at | NM_001259 | Hs.119882 | 3 | 0.00634 | Decrease |

TABLE 12A-continued

Genes with Altered Steady State RNA Levels in Dendritic Cells prepared from Day Old Monocytes as compared to Dendritic Cells Prepared from Fresh Monocytes

| Gene Symbol | Affymetrix Identifier | NCBI | Unigene | Fold | P value | Change in Day Old |
|---|---|---|---|---|---|---|
| CD69 | 209795_at | NM_001781 | Hs.208854 | 2.6 | 0.0145 | Decrease |
| TLR1 | 210176_at | NM_003263 | Hs.111805 | 2.193 | 0.456 | Decrease |
| TLR2 | 204924_at | NM_003264 | Hs.519033 | 2 | 0.089 | Decrease |
| ENO3 | 204483_at | NM_001976 NM_053013 | Hs.224171 | 6 | 0.0588 | Increase |
| CD52 | 34210_at | NM_001803 | Hs.276770 | 5 | 0.0925 | Increase |
| TRPS1 | 234351_x_at | NM_014112 | Hs.253594 | 4 | 0.067 | Increase |
| FLJ21069 (RSNL2) | 226425_at | NM_024692 | Hs.122927 | 3.7 | 0.0806 | Increase |
| TNS | 218864_at | NM_022648 | Hs.471381 | 3.5 | 0.019 | Increase |
| CPEB1 | 219578_s_at | NM_030594 | Hs.459132 | 3.2 | 0.0779 | Increase |
| RAB9P40 | 203150_at | NM_005833 | Hs.19012 | 3 | 0.0357 | Increase |
| PIR | 207469_s_at | NM_001018109 NM_003662 | Hs.495728 | 3 | 0.0559 | Increase |
| CALM2 | 235190_at | NM_001743 | Hs.468442 | 3 | 0.0913 | Increase |
| ABCG2 | 209735_at | NM_004827 | Hs.480218 | 3 | 0.0985 | Increase |
| A2M | 217757_at | NM_000014 | Hs.212838 | 3 | 0.0384 | Increase |
|  | 232750_at |  | Hs.550958 | 3 | 0.0207 | Increase |
| APEX2 | 204408_at | NM_014481 | Hs.555936 | 4.3038 | 0.027 | Increase |
| THBD | 203888_at | NM_000361 | Hs.2030 | 6.5432 | 0.122 | Decrease |
| DNASE1L3 | 205554_s_at | NM_004944 | Hs.476453 | 3.9148 | 0.108 | Decrease |
| PKIB | 223551_at | NM_032471 | Hs.486354 | 3.6986 | 0.130 | Decrease |
| PTGER3 | 210375_at | NM_000957 | Hs.445000 | 28.2 | 0.0979 | Decrease |
| CAMTA1 | 213268_at | NM_015215 | Hs.397705 | 6.4 | 0.0897 | Decrease |
| PLS3 | 201215_at | NM_005032 | Hs.496622 | 6.4 | 0.0436 | Decrease |
| TREM1 | 219434_at | NM_018643 | Hs.283022 | 5.2 | 0.031 | Decrease |
| TMEPAI | 217875_at | NM_020182 | Hs.517155 | 5.5 | 0.0784 | Decrease |
| CHI3L1 | 209396_at | NM_001276 | Hs.382202 | 6.5 | 0.0367 | Increase |

TABLE 12B

Description of Genes Listed in Table 12A

| Gene Symbol | Go Description | |
|---|---|---|
| ALOX15 | Arachidonate 15-lipoxygenase | Electron transport, lipid metabolism, inflammatory response, leukotriene biosynthesis, leukotriene metabolism |
|  | CDNA FLJ37485 fis Clone BRAWH2014379 | |
| KRT17; PC; K17; PC2; PCHC1 | Keratin 17 | Epidermis development |
| KCNJ2 | Potassium inwardly-rectifying channel, subfamily J, member 2 | Ion transport |
| YWHAZ | Tyrosine 3-monooxygenase/tryptophan 5-monooxygenase activation protein, zeta polypeptide | Protein domain specific binding |
| IL1B | Interlukin 1, beta | immune response, inflammatory response |
| PTX3 | Pentraxin-related gene, rapidly induced by IL-1 beta | Inflammatory response |
| FYN | FYN oncogene related to SRC, FGR, YES | Protein amino acid phosphorylation, protein amino acid phosphorylation intracellular signaling cascade protein kinase cascade protein amino acid phosphorylation calcium ion transport |
| GALNT3 | UDP-N-acetyl-alpha-D-galactosamine-polypeptide N-acetylgalactosaminyltransferase 3 (GalNAc-T3) | Carbohydrate metabolism |
| FLJ20073 | Sterile alpha motif domain containing 9 | Binding |
| CDK6 | Cyclin-dependent kinase 6 | Regulation of progression through cell cycle G1 phase of mitotic cell cycle protein amino acid phosphorylation cell proliferation |
| CD69 | CD69 antigen (p60, early T-cell activation antigen) | Defense response, cell surface receptor linked signal transduction |

TABLE 12B-continued

Description of Genes Listed in Table 12A

| Gene Symbol | | Go Description |
|---|---|---|
| TRL1 | Toll-like receptor 1 | inflammatory response, immune response |
| TRL2 | Toll-like receptor 2 | Induction of apoptosis, inflammatory response, signal transduction, immune response |
| ENO3 | Enolase 3 (beta, muscle) | Glycolysis |
| CD52 | CD52 antigen (CAMPATH-1 antigen) | integral to plasma membrane |
| TRPS1 | Trichorhinophalangeal syndrome 1 | Skeletal development transcription regulation of transcription, DNA-dependent transcription from RNA polymerase II promoter NLS-bearing substrate import into nucleus |
| FLJ21069, RSNL2 | Restin-line 2 | |
| TNS | Tensin1 | Intracellular signaling cascade |
| CPEB1 | Cytoplasmic polyadenylation element binding protein 1 | mRNA processing |
| RAB9P40 | Rab9 effector protein with kelch motifs | Receptor mediated endocytosis, vesicle docking during exocytosis |
| PIR | Pirin (iron-binding nuclear protein) | Transcription cofactor activity iron ion binding metal ion binding |
| CALM2 | Calmodulin 2 (phosphorylase kinase, delta) | G-protein coupled receptor protein signaling pathway |
| ABCG2 | ATP-binding cassett, sub-family G (WHITE), member 2 | Transport response to drug transport |
| A2M | Alpha-2 macroglobulin | Intracellular protein transport protein homooligomerization |
| | CDNA FLJ13750 fis, clone PLACE 3000331 | |
| APEX2 | APEX nuclease (apurinic/apyrimidinic endonuclease) 2 | DNA repair response to DNA damage stimulus |
| THBD | Thrombomodulin | Transmembrane receptor activity, calcium ion binding, sugar binding, receptor activity, calcium ion binding receptor activity |
| DNASE1L3 | DNASE1L3 | DNA catabolism, apoptosis, DNA metabolism |
| PKIB | Protein kinase (cAMP-dependent, catalytic) inhibitor beta | Negative regulation of protein kinase activity |
| PTGER3 | Prostaglandin E receptor 3 (subtype EP3) | Transcription, DNA-dependant, signal transduction, cell death, G-protein coupled receptor protein signaling pathway |
| CAMTA1 | Calmodulin binding transcription activator 1 | WNT receptor signaling pathway |
| PLS3 | Plastin 3 (T isoform) | Actin binding calcium ion binding actin binding |
| TREM1 | Triggering receptor expressed on myeloid cells 1 | Humoral immune response intracellular signaling cascade |
| TMEPAI | Transmembrane, prostate androgen induced RNA | Integral to membrane |
| CHI3L1 | Chitinase-3-like 1 (cartilage glycoprotein-39) | Carbohydrate metabolism chitin catabolism |

TABLE 13A

Genes with Altered Steady State RNA Levels in Day Old Monocytes as compared to Fresh Monocytes

| Gene Symbol | Affymetrix Identifier | NCBI | Unigene | Fold | P value | Change in Day Old |
|---|---|---|---|---|---|---|
| ADM | 202912_at | NM_001124 | Hs.440147 | 6.67 | 0.020 | Increase |
| Est | 230127_at | AW044663 | Hs.232417 | 5.29 | 0.017 | Increase |
| PPARD | 242218_at | NM_006238 | Hs.485196 | 5.29 | 0.040 | Increase |
| CIAS1 | 216016_at | NM_004895, NM_183395 | Hs.159483 | 4.60 | 0.030 | Increase |
| SLC6A6 | 211030_s_at | NM_003043 | Hs.529488 | 3.30 | 0.020 | Increase |
| Est | 243423_at | AF150368 | Hs.205098 | 3.40 | 0.015 | Increase |
| WTAP | 1560274_at | NM_004906, NM_152857, NM_152858 | Hs.446091 | 3.30 | 0.008 | Increase |
| | 1556072_at | AK097861 | Hs.517397 | 3.90 | 0.010 | Increase |

TABLE 13A-continued

Genes with Altered Steady State RNA Levels in Day Old Monocytes as compared to Fresh Monocytes

| Gene Symbol | Affymetrix Identifier | NCBI | Unigene | Fold | P value | Change in Day Old |
|---|---|---|---|---|---|---|
| APAF1 | 204859_s_at | NM_013229 | Hs.552567 | 3.00 | 0.020 | Decrease |
| CCR2 | 206978_at | NM_000647, NM_000648 | Hs.511794 | 4.05 | 0.004 | Decrease |
| SLC35A5 | 218519_at | NM_017945 | Hs.237480 | 4.12 | 0.030 | Decrease |
| RPE | 225039_at | NM_006916, NM_199229 | Hs.282260 | 4.12 | 0.040 | Decrease |
| TRPS1 | 222651_s_at | NM_014112 | Hs.253594 | 4.17 | 0.020 | Decrease |
| OXR1 | 222553_x_at | NM_181354 | Hs.148778 | 4.22 | 0.006 | Decrease |
| TRIM14 | 203148_s_at | NM_014788 NM_033219 NM_033220 NM_033221 | Hs.555909 | 4.22 | 0.040 | Decrease |
| MRF2 | 212614_at | NM_032199 | Hs.535297 | 4.22 | 0.040 | Decrease |
| TNFSF10 | 214329_x_at | NM_003810 | Hs.478275 | 4.37 | 0.040 | Decrease |
| DKFZp434L142 | 219872_at | NM_001031700 NM_016613 | Hs.535739 | 4.42 | 0.030 | Decrease |
| LOC115294 (PCMTD1) | 232382_s_at | NM_052937 | Hs.308480 | 4.15 | 0.030 | Decrease |
| LOC201895 | 227052_at | NM_174921 | Hs.205952 | 4.88 | 0.040 | Decrease |
| PAG1 | 227354_at | NM_018440 | Hs.266175 | 5.03 | 0.046 | Decrease |
| DMXL1 | 203791_at | NM_005509 | Hs.181042 | 5.46 | 0.002 | Decrease |
| CX3CR1 | 205898_at | NM_001337 | Hs.78913 | 10.88 | 0.030 | Decrease |

TABLE 13B

Description of Genes Listed in Table 13A

| Gene Symbol | | Go description |
|---|---|---|
| ADM | Adrenomedullin | cAMP biosynthesis, progesterone biosynthesis, Signal transuction, cell-cell signaling, pregnancy, excretion |
| Est | Transcribed locus | |
| PPARD | Peroxisome proliferative activated receptor, delta | Transcription regulator |
| CIAS1 | Cold autoinflammatory syndrome 1 | Apoptosis, induction of apoptosis, inflammatory response, signal transduction |
| SLC6A6 | Solute carrier family 6 member 6 | Amino acid metabolism, integral to plasma membrane |
| Est | Transcribed locus | |
| WTAP | Wilms tumor 1 associated protein | |
| APAF1 | Hypothetical protein apoptotic peptidase activating factor | regulation of apoptosis |
| CCR2 | Chemokine (C-C motif) receptor 2 | Chemotaxis, inflammatory response, cellular defense response, signal transduction |
| SLC35A5 | Solute carrier family 35, member A5 | Carbohydrate transport, nucleotide-sugar transport |
| RPE | Ribulose-5-phosphate-3-epimerase | Carbohydrate metabolism |
| TRPS1 | Trichorhinophalangeal syndrome I | Transcription factor activity |
| OXR1 | Oxidation resistance 1 | Response to oxidative stress |
| TRIM14 | Tripartite motif-containing 14 | Compartment specification |
| MRF2 | AT rich interactive domain 5B (MRF1-like) | Transcription, negative regulation of transcription, DNA-dependent, regulation of transcription, DNA-dependent |
| TNFSF10 | Tumor necrosis factor (ligand) superfamily, member 10 | Apoptosis, induction of apoptosis, inflammatory response, signal transduction, cell-cell signaling |
| DKFZp434L142 | Hypothetical protein DKFZp434L142 | |
| LOC115294 (PCMTD1) | Protein-L-isoaspartate (D-aspartate) O-methyltransferase domain containing 1 | Protein modification |
| LOC201895 | Hypothetical protein LOC201895 | Protein binding |
| PAG1 | Phosphoprotein associated with glycosphingolipid microdomains 1 | Negative regulation of T cell activation, intracellular signaling cascade, regulation of T cell activation |

TABLE 13B-continued

Description of Genes Listed in Table 13A

| Gene Symbol | | Go description |
|---|---|---|
| DMXL1 | Protein binding | |
| CX3CR1 | Chemokine (C-X3-C motif) receptor 1 | Chemotaxis, cellular defense response, cell adhesion, signal transduction |

The dendritic cell genes were further normalized to expression of two housekeeping genes shown to remain constant between DCs produced from fresh and day old monocytes. The average expression of each gene (normalized) was divided by the average expression (normalized) of GAPDH (glyceraldehyde-3-phosphate dehydrogenase) or β-actin to produce a ratio of expression relative to the housekeeping gene. The results for six genes are shown in Table 14. "$DC_{do}$" refers to DCs prepared from day old monocytes. "$DC_f$" refers to DCs prepared from fresh monocytes.

TABLE 14

Steady State RNA Expression Ratios of Certain RNAs to GAPDH or β-Actin in DCs prepared from Day Old or Fresh Monocytes

| Gene | Gene:GAPDH $DC_{do}$ | Gene:GAPDH $DC_f$ | Gene:Actin $DC_{do}$ | Gene:Actin $DC_f$ |
|---|---|---|---|---|
| ALOX15 | 0.45 | 1.5 | 0.45 | 1.52 |
| 1L1β | 0.58 | 1.38 | 0.57 | 1.37 |
| TLR1 | 0.68 | 1.49 | 0.68 | 1.48 |
| TLR2 | 0.67 | 1.34 | 0.66 | 1.33 |
| CD69 | 0.66 | 1.61 | 0.65 | 1.60 |
| CD52 | 1.86 | 0.74 | 1.85 | 0.74 |

Additional verification, to date, of differential expression in monocytes of two of the candidate genes was performed by Quantitative Real-Time PCR (QPCR) using the primers shown in Table 15. First strand cDNA was generated from each total RNA (identical to that used in the GeneChip analysis) using oligo(dT) primers and SuperScript™ III First-Strand Synthesis System for RT-PCR according to the manufacturer's instructions (Invitrogen, Carlsbad, Calif.). QPCR was performed using an ABI Prism® 7900HT Sequence Detection System (Applied Biosystems, Foster City, Calif.) according to the manufacturer's instruction (ABI Prism® 7900HT Sequence Detection System User Guide). TaqMan® Gene Expression Assays or Custom TaqMan® Gene Expression Assays (Applied Biosystems, Foster City, Calif.) were used as TaqMan® probes. PCR reactions were performed in triplicate using ABsolute™ QPCR ROX Mix (ABgene, Surrey, UK). Quantitation of relative cDNA concentrations was done using the relative standard curve method as described in ABI Prism® 7700 Sequence Detection System User Bulletin #2 (Applied Biosystems, Foster City, Calif.). One cDNA with the most expression of each gene in the GeneChip analysis was used for generating the relative standard curve. All data are shown as expression relative to internal GAPDH expression. APAF-1 and CDCA2 effector protein 2 were demonstrated to decrease, relative to GAPDH, at least 2.5 fold and 3 fold, respectively between fresh and day old monocytes.

TABLE 15

Primers

| Gene | TaqMan ® Gene Expression Assays ID |
|---|---|
| GAPDH | Hs99999905_m1 |
| CDC42 effector protein 2 | Hs00198943_m1 |
| APAF1 | Hs00185508_m1 |

Example 10

Comparison of Dendritic Cells Prepared from PBMCs Incubated at Room Temperature for 23, 48 or 71 Hours from the Time of Isolation from a Donor Methods:

'Healthy donor' leukapheresis products from two donors were received after overnight shipping. Approximately one third of each product was processed for DC generation at the specified times post apheresis collection as follows. The leukopheresis product (i.e., PBMCs) was incubated at room temperature for 23, 48 or 71 hours prior to ficoll-histopaque density gradient centrifugation and the adherence step described below. After the room temperature incubation period, the viability of the PBMCs and the percentages of B cells, T cells, monocytes and NK cells were determined. The results are shown in Table 16.

TABLE 16

Characterization of cellular product on Day 0 of culture

| | Donor 1 | | | Donor 2 | | |
|---|---|---|---|---|---|---|
| | 23 hrs | 48 hrs | 71 hrs | 23 hrs | 48 hrs | 71 hrs |
| PBMC viability (%) | 97 | 99 | 97 | 98 | 99 | 97 |
| % B-cells | 4 | 3.8 | 4.4 | 5.15 | 4.55 | 5.45 |
| % T-cells | 38.9 | 35.5 | 27.4 | 49.3 | 42.7 | 46.4 |
| % Monocytes | 41.9 | 37.7 | 41.2 | 29.5 | 24.4 | 28.7 |
| % NK-cells | 6.4 | 11.3 | 10.9 | 4.7 | 2.54 | 5.7 |

Generation of DC Products

PBMCs were prepared by ficoll-histopaque density centrifugation, and washed four times in PBS at room temperature. $2 \times 10^8$ PBMCs were re-suspended in 30 ml AIM-V medium (Invitrogen) and allowed to adhere to 150 cm³ plastic flasks for 2 hours at 37° C. Non-adherent cells were removed and remaining cells cultured in X-VIVO 15 medium, supplemented with 1000 U/ml GM-CSF (Leukine) and 1000 U/ml IL-4 (R&D systems), for 5 days at 37° C., 5% $CO_2$. Immature DCs were initially matured by addition of TNF-α (10 ng/ml), IFN-γ (1000 U/ml) and $PGE_2$ (1 μg/ml). After overnight culture, the TIP-DC intermediate products were harvested by removal of media, and a cold PBS wash. TIP-DC were phenotyped to confirm the generation of a mature population of cells. To generate antigen-loaded, fully mature DC, the TIP-DC were electroporated: Cells were re-suspended in chilled Viaspan at 4×10$^7$/ml in 0.5 ml and placed on ice. DCs were mixed with amplified total tumor renal cell carcinoma mRNA at 1 μg/10$^6$ cells, as a model antigen-encoding payload, plus 4 μg/10$^6$ CD40L mRNA, and placed in a 4 mm gap electroporation cuvette, followed by electroporation using a Biorad GenePulsar Xcell system. Immediately after electroporation, DCs were washed in X-VIVO 15 medium and finally re-suspended in 20 ml of X-VIVO 15 supplemented with GM-CSF (800 U/ml) and IL-4 (500 U/ml) at 1×10$^6$/ml, and cultured for 4 hours at 37° C. in low adherence T75 flasks. Cell counts and viability determinations were made using propidium iodide and CalTag counting beads as described by the manufacturer. Post-ficoll PBMC samples, day 6 TIP-DC, DCs recovered 4 hrs after electroporation and culture (PME-CD40L DC), and post thaw of the final product, were all subjected to cell count and viability analysis. The results are shown in Table 17.

TABLE 17

Recovery and Yield of DC during the generation of PME-CD40L DC

| | No. of seeded PBMCs/flask | Percent of input PBMC recovered Day 6/viability | 4 hr post electroporation % Recovery/viability | Freeze/thaw % Recovery/viability of final product |
|---|---|---|---|---|
| Donor 1 | | | | |
| 23 hrs | 2 × 10$^8$ | 27%/96% viable | 60%/93% viable | 78%/86% viable |
| 48 hrs | 2 × 10$^8$ | 17%/98% viable | 58%/95% viable | 85%/94% viable |
| 72 hrs | 2 × 10$^8$ | 9%/97% viable | 50%/96% viable | 71%/93% viable |
| Donor 2 | | | | |
| 19 hrs | 2 × 10$^8$ | 6.6%/95% viable | 68%/95% viable | 68.9%/91% viable |
| 41 hrs | 2 × 10$^8$ | 12%/96% viable | 62%/93% viable | 78.5%/89% viable |
| 66 hrs | 2 × 10$^8$ | 3.1%/97% viable | 41%/91% viable | 86.3%/90% viable |

Phenotyping of PBMC and DC Products

All antibodies were sourced from BD Biosciences and used at dilutions recommended by the manufacturer. PBMCs: 3×10$^5$ cells were each stained with CD19-PE, CD14-PE and CD3-PE, or matched isotype conjugated controls by incubation in antibody for 30 minutes at 4 C. After incubation, the stained cells were washed 3 times in cold 1% FBS/PBS and resuspended in PBS for fluorescence analysis using a FACScalibur flow cytometer (BD Biosciences) using CellQuest software (BD Biosciences). 3 minutes prior to acquisition, propidium iodide (1 ug/ml) was added to each sample as a viability dye for gating purposes. DCs: 1×10$^6$ cells (TIP-DC and PME-CD40L DC) were re-suspended in chilled PBS/1% FBS. PE or FITC conjugated antibodies specific for MHC molecules (HLA-ABC, HLA-DR), or co-stimulatory molecules (CD80, CD86), or maturation markers (CD83) or monocyte/DC lineage markers (CD14, CD209) were mixed with 1×10$^5$ DCs per and incubated at 4° C. for 30 minutes. Isotype matched antibodies were used as controls. After thorough washing cells were subjected to flow cytometry as described above. Intracellular CD40L was determined as follows: 2×10$^5$ PME-CD40L DCs re-suspended in 250 μL of Cytofix/Cytoperm solution (BD Biosciences) for a minimum of 10 minutes up to 2 hours at 4° C. Cells were washed twice with 2 ml staining buffer (PBS, BSA, NaN$_3$, and EDTA), re-suspended in 0.5 ml staining buffer and stored over night at 4° C. Cells were re-suspended in 2.0 ml Perm/Wash solution (BD Biosciences) for 15 minutes, centrifuged and re-suspended in 100 μl Penn/Wash solution. 20 μL of mouse anti-human CD40L APC or mouse IgG1 APC was added to each DC preparation and incubated at 4° C. for 30 minutes in the dark. Cells were washed twice with 1 ml Penn/Wash solution and re-suspended in staining buffer prior to flow cytometric analysis. The results are shown in Table 18.

TABLE 18

Phenotype of intermediate TIP-DC and final PME-CD40L DC product

| | Donor 1 | | | Donor 2 | | |
|---|---|---|---|---|---|---|
| | 23 hrs | 48 hrs | 71 hrs | 23 hrs | 48 hrs | 71 hrs |
| Day 6 TIP-DC (%) | | | | | | |
| CD14 | 4.1 | 1.23 | .62 | .16 | 1.38 | .89 |
| CD80 | 96.92 | 97.9 | 98.3 | 99.4 | 99.5 | 87.8 |
| CD83 | 84.19 | 88 | 93 | 92.2 | 88.5 | 62.1 |
| CD86 | 99.31 | 99.6 | 98.4 | 99.8 | 99.9 | 99.4 |
| HLA-I | 95.65 | 94.6 | 96.1 | 95.6 | 97.4 | 82.6 |

TABLE 18-continued

Phenotype of intermediate TIP-DC and final PME-CD40L DC product

| | Donor 1 | | | Donor 2 | | |
|---|---|---|---|---|---|---|
| | 23 hrs | 48 hrs | 71 hrs | 23 hrs | 48 hrs | 71 hrs |
| HLA-II | 99.55 | 99.7 | 98.5 | 99.8 | 99.8 | 96.9 |
| Final PME-CD40L product (%) | | | | | | |
| CD14 | 1.19 | 1.36 | 1.3 | .43 | .66 | 1.08 |
| CD209 | 97.98 | 97.60 | 98.23 | 89.9 | 98.2 | 96.3 |

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications, and in particular relevant portions thereof, are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Data in Table 16, from two independent experiments, show that apheresis products that are held for up to 72 hrs post collection from the patient can yield highly viable PBMC populations, without significant bias in the recovered leukocyte subsets. Seeding of flasks with PBMCs from each time point, and culture for the generation of mature DCs (TIP-DCs) results in a high frequency of viable cells, although the total recovery of DCs using apheresis products held for extended time periods does decline (Table 17). Nevertheless, sufficient DCs can be generated for further processing by electroporation with total amplified tumor RNA, and CD40L RNA. Most importantly, Tables 17 and 18 show that TIP-DCs generated from the various starting products are equally amenable to electroporation, and recovery, with full maturation into the final product, PME-CD40L DC. PME-CD40L DC generated from this study can be formulated as 'vaccine' and frozen and thawed without any deterioration of the DC preparations. In conclusion, apheresis products held for up to 72 hrs post collection are a viable raw material for centralized manufacturing of DC vaccines for application in the clinic.

What is claimed is:

1. A method for producing dendritic cells from monocytes, comprising:
   a) providing monocytes that have been incubated without culturing at a temperature maintained between 1° C.-34° C. for a period of approximately 6 to 96 hours from the time they are isolated from a subject; and
   b) inducing the differentiation of said monocytes into dendritic cells.

2. The method of claim 1, wherein the monocytes are human monocytes.

3. The method of claim 1, wherein the incubation temperature is maintained between 6° C.-28° C.

4. The method of claim 1, wherein the incubation temperature is maintained between 8° C.-26° C.

5. The method of claim 1, wherein the period of incubation is 8 to 48 hours.

6. The method of claim 5, wherein the period of incubation is 10 to 30 hours.

7. The method of claim 1, wherein the period of incubation is 26 to 72 hours.

8. The method of claim 1, wherein the period of incubation is 48 to 80 hours.

9. The method of claim 1, wherein the differentiation is induced by contacting the monocytes in a culture medium comprising an effective amount of a composition that induces the differentiation of monocytes into immature dendritic cells.

10. The method of claim 1, wherein the monocytes are present together with peripheral blood mononuclear cells (PBMCs) during all or a portion of the incubation period.

11. The method of claim 10, wherein the PBMCs are isolated from the subject by leukapheresis.

12. The method of claim 10, wherein the monocytes are enriched from the PBMCs during or following the incubation period.

13. The method of claim 9, further comprising a step of maturing the immature dendritic cells into mature dendritic cells.

14. The method of claim 13, further comprising loading one or more antigens into said mature dendritic cells.

15. The method of claim 1, wherein the incubation temperature is between 1° C.-20° C.

16. The method of claim 12, further comprising the step of freezing said enriched monocytes.

* * * * *

UNITED STATES PATENT AND TRADEMARK OFFICE
CERTIFICATE OF CORRECTION

PATENT NO. : 8,153,425 B2  
APPLICATION NO. : 11/918076  
DATED : April 10, 2012  
INVENTOR(S) : Pogue-Caley et al.

Page 1 of 1

It is certified that error appears in the above-identified patent and that said Letters Patent is hereby corrected as shown below:

On the title page, please insert item 60 under the Prior Publication Data:

--Related U.S. Application Data  
Provisional application No. 60/669,468, filed on April 8, 2005.--

Signed and Sealed this  
Twelfth Day of May, 2015

Michelle K. Lee  
*Director of the United States Patent and Trademark Office*

SEQUENCE LISTING

<160> NUMBER OF SEQ ID NOS: 121

<210> SEQ ID NO 1
<211> LENGTH: 2707
<212> TYPE: DNA
<213> ORGANISM: Homo sapiens
<220> FEATURE:
<221> NAME/KEY: misc_feature
<222> LOCATION: (15)..(2003)
<223> OTHER INFORMATION: ALOX-15 Coding Sequence

<400> SEQUENCE: 1

```
catctttgag caagatgggt ctctaccgca tccgcgtgtc cactggggcc tcgctctatg      60
ccggttccaa caaccaggtg cagctgtggc tggtcggcca gcacggggag gcggcgctcg     120
ggaagcgact gtggcccgca cggggcaagg agacagaact caaggtggaa gtaccggagt     180
atctggggcc gctgctgttt gtgaaactgc gcaaacggca cctccttaag gacgacgcct     240
ggttctgcaa ctggatctct gtgcagggcc ccggagccgg ggacgaggtc aggttccctt     300
gttaccgctg ggtggagggc aacggcgtcc tgagcctgcc tgaaggcacc ggccgcactg     360
tgggcgagga ccctcagggc ctgttccaga aacaccggga agaagagctg gaagagagaa     420
ggaagttgta ccggtgggga aactggaagg acgggttaat tctgaatatg gctggggcca     480
aactatatga cctccctgtg gatgagcgat ttctggaaga caagagagtt gactttgagg     540
tttcgctggc caagggggctg gccgacctcg ctatcaaaga ctctctaaat gttctgactt     600
gctggaagga tctagatgac ttcaaccgga ttttctggtg tggtcagagc aagctggctg     660
agcgcgtgcg ggactcctgg aaggaagatg ccttatttgg gtaccagttt cttaatggcg     720 ccaacccgt ggtgctgagg cgctctgctc accttcctgc tcgcctagtg ttccctccag      780
gcatggagga actgcaggcc cagctggaga aggagctgga gggaggcaca ctgttcgaag     840
ctgacttctc cctgctggat gggatcaagg ccaacgtcat tctctgtagc cagcagcacc     900
tggctgcccc tctagtcatg ctgaaattgc agcctgatgg gaaactcttg cccatggtca     960
tccagctcca gctgccccgc acaggatccc caccacctcc cctttttcttg cctacggatc    1020 ccccaatggc ctggcttctg gccaaatgct gggtgcgcag ctctgacttc cagctccatg    1080
agctgcagtc tcatcttctg aggggacact tgatggctga ggtcattgtt gtggccacca    1140
```

-continued

```
tgaggtgcct gccgtcgata catcctatct tcaagcttat aattccccac ctgcgataca    1200
ccctggaaat taacgtccgg gccaggactg ggctggtctc tgacatggga attttcgacc    1260
agataatgag cactggtggg ggaggccacg tgcagctgct caagcaagct ggagccttcc    1320
taacctacag ctccttctgt cccccctgatg acttggccga ccgggggctc ctgggagtga    1380
agtcttcctt ctatgcccaa gatgcgctgc ggctctggga aatcatctat cggtatgtgg    1440
aaggaatcgt gagtctccac tataagacag acgtggctgt gaaagacgac ccagagctgc    1500
agacctggtg tcgagagatc actgaaatcg ggctgcaagg ggcccaggac cgagggtttc    1560
ctgtctcttt acaggctcgg gaccaggttt gccactttgt caccatgtgt atcttcacct    1620
gcaccggcca acacgcctct gtgcacctgg gccagctgga ctggtactct gggtgcctta    1680
atgcaccctg cacgatgcgg ctgcccccgc caaccaccaa ggatgcaacg ctggagacag    1740
tgatggcgac actgcccaac ttccaccagg cttctctcca gatgtccatc acttggcagc    1800
tgggcagacg ccagcccgtt atggtggctg tgggccagca tgaggaggag tattttttcgg    1860 gccctgagcc taaggctgtg ctgaagaagt tcagggagga gctggctgcc ctggataagg    1920
aaattgagat ccggaatgca aagctggaca tgccctacga gtacctgcgg cccagcgtgg    1980
tggaaaacag tgtggccatc taagcgtcgc caccctttgg ttatttcagc ccccatcacc    2040
caagccacaa gctgacccct tcgtggttat agccctgccc tcccaagtcc caccctcttc    2100
ccatgtccca ccctccctag aggggcacct tttcatggtc tctgcaccca gtgaacacat    2160
tttactctag aggcatcacc tgggaccttta ctcctctttc cttccttcct cctttcctat    2220
cttccttcct ctctctcttc ctctttcttc attcagatct atatggcaaa tagccacaat    2280
tatataaatc atttcaagac tagaataggg ggatataata catattactc cacaccttt    2340 atgaatcaaa tatgattttt ttgttgttgt taagacagag tctcactttg acacccaggc    2400
tggagtgcag tggtgccatc accacggctc actgcagcct cagcgtcctg ggctcaaatg    2460
atcctcccac ctcagcctcc tgagtagctg ggactacagg ctcatgccat catgcccagc    2520
taatattttt ttattttcgt ggagacgggg cctcactatg ttgcctaggc tggaaatagg    2580
attttgaacc caaattgagt ttaacaataa taaaaagttg ttttacgcta aagatggaaa    2640
agaactagga ctgaactatt ttaaataaaa tattggcaaa agaaaaaaaa aaaaaaaaa    2700 aaaaaaa                                                              2707
```

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2

```
ccctagaggg gcacctttc atggt                                              25
```

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 3

```
tagaggggca ccttttcatg gtctc                                             25
```

<210> SEQ ID NO 4

```
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
tttactctag aggcatcacc tggga                                            25

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
tagaggcatc acctgggacc ttact                                            25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
tcctctttct tcattcagat ctata                                            25

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
cttcattcag atctatatgg caaat                                            25

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
tagccacaat tatataaatc atttc                                            25

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 9
atattactcc acacctttta tgaat                                            25

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
```

-continued actccacacc ttttatgaat caaat                                              25

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
tattttcgtg gagacggggc ctcac                                              25

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12
ggctggaaat aggattttga accca                                              25

<210> SEQ ID NO 13
<211> LENGTH: 1498
<212> TYPE: DNA
<213> ORGANISM: Homo sapiens
<220> FEATURE:
<221> NAME/KEY: misc_feature
<222> LOCATION: (88)..(897)
<223> OTHER INFORMATION: IL-1B Coding Sequence

<400> SEQUENCE: 13
accaaacctc ttcgaggcac aaggcacaac aggctgctct gggattctct tcagccaatc         60
ttcattgctc aagtgtctga agcagccatg gcagaagtac ctgagctcgc cagtgaaatg        120
atggcttatt acagtggcaa tgaggatgac ttgttctttg aagctgatgg ccctaaacag        180
atgaagtgct ccttccagga cctggacctc tgccctctgg atggcggcat ccagctacga        240
atctccgacc accactacag caagggcttc aggcaggccg cgtcagttgt tgtggccatg        300
gacaagctga ggaagatgct ggttccctgc ccacagacct ccaggagaa tgacctgagc        360 accttctttc ccttcatctt tgaagaagaa cctatcttct tcgacacatg ggataacgag        420
gcttatgtgc acgatgcacc tgtacgatca ctgaactgca cgctccggga ctcacagcaa        480
aaaagcttgg tgatgtctgg tccatatgaa ctgaaagctc tccacctcca gggacaggat        540
atggagcaac aagtggtgtt ctccatgtcc tttgtacaag agaagaaag taatgacaaa        600 atacctgtgg ccttgggcct caaggaaaag aatctgtacc tgtcctgcgt gttgaaagat        660
gataagccca ctctacagct ggagagtgta gatcccaaaa attacccaaa gaagaagatg        720
gaaaagcgat ttgtcttcaa caagatagaa atcaataaca agctggaatt tgagtctgcc        780
cagttcccca actggtacat cagcacctct caagcagaaa acatgcccgt cttcctggga        840
gggaccaaag gcggccagga tataactgac ttcaccatgc aatttgtgtc ttcctaaaga        900
gagctgtacc cagagagtcc tgtgctgaat gtggactcaa tccctagggc tggcagaaag        960
ggaacagaaa ggtttttgag tacggctata gcctggactt tcctgttgtc tacaccaatg       1020
cccaactgcc tgcctttaggg tagtgctaag aggatctcct gtccatcagc caggacagtc       1080
agctctctcc tttcagggcc aatccccagc ccttttgttg agccaggcct ctctcacctc       1140
tcctactcac ttaaagcccg cctgacagaa accacggcca catttggttc taagaaaccc       1200
tctgtcattc gctcccacat tctgatgagc aaccgcttcc ctatttattt atttatttgt       1260

```
ttgtttgttt tattcattgg tctaatttat tcaaaggggg caagaagtag cagtgtctgt    1320
aaaagagcct agttttaat agctatggaa tcaattcaat ttggactggt gtgctctctt    1380
taaatcaagt cctttaatta agactgaaaa tatataagct cagattattt aaatgggaat    1440
atttataaat gagcaaatat catactgttc aatggttctg aaataaactt cactgaag      1498
```

```
<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
agctgtaccc agagagtcct gtgct                                            25

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
tggactcaat ccctagggct ggcag                                            25

<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 16
ggtttttgag tacggctata gcctg                                            25

<210> SEQ ID NO 17
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 17
tatagcctgg actttcctgt tgtct                                            25

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
ccaactgcct gccttagggt agtgc                                            25

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 19
ctaagaggat ctcctgtcca tcagc                                            25
```

```
<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 20
cacttaaagc ccgcctgaca gaaac                                          25

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 21
gacagaaacc acggccacat ttggt                                          25

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 22
cattcgctcc cacattctga tgagc                                          25

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 23
cacattctga tgagcaaccg cttcc                                          25

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 24
ggtgtgctct ctttaaatca agtcc                                          25

<210> SEQ ID NO 25
<211> LENGTH: 2867
<212> TYPE: DNA
<213> ORGANISM: Homo sapiens
<220> FEATURE:
<221> NAME/KEY: misc_feature
<222> LOCATION: (275)..(2635)
<223> OTHER INFORMATION: TLR1 Coding Sequence

<400> SEQUENCE: 25
acagactgcc aaatggaaca gacaagcagg ttgtcttgtg ttaaagaaaa tgagatataa     60
gtcagttact cccggaggca atgctgctgt tcagctcttc tgttttttgtg gccagggtct   120 tcatgaacac taatagggggt accaggccct cttcctcgtt agaagaaatc aggataacaa   180
aggcatattg ggcaccccta caaaaggaat ctgtatctgt atcaagatga tctgaagaac   240
```

```
agcttctacc tttaggaatg tctagtgttc caaaatgact agcatcttcc attttgccat    300
tatcttcatg ttaatacttc agatcagaat acaattatct gaagaaagtg aattttagt    360
tgataggtca aaaaacggtc tcatccacgt tcctaaagac ctatcccaga aaacaacaat    420
cttaaatata tcgcaaaatt atatatctga gctttggact tctgcatct tatcactgtc    480
aaaactgagg atttttgataa tttctcataa tagaatccag tatcttgata tcagtgtttt    540
caaattcaac caggaattgg aatacttgga tttgtcccac aacaagttgg tgaagatttc    600
ttgccaccct actgtgaacc tcaagcactt ggacctgtca tttaatgcat ttgatgccct    660
gcctatatgc aaagagtttg gcaatatgtc tcaactaaaa tttctggggt tgagcaccac    720
acacttagaa aaatctagtg tgctgccaat tgctcatttg aatatcagca aggtcttgct    780
ggtcttagga gagacttatg gggaaaaaga agaccctgag ggccttcaag actttaacac    840
tgagagtctg cacattgtgt tccccacaaa caaagaattc cattttatttt tggatgtgtc    900
agtcaagact gtagcaaatc tggaactatc taatatcaaa tgtgtgctag aagataacaa    960
atgttcttac ttcctaagta ttctggcgaa acttcaaaca aatccaaagt tatcaaatct   1020
taccttaaac aacattgaaa caacttggaa ttctttcatt aggatcctcc agctggtttg   1080
gcatacaact gtatggtatt tctcaatttc aaacgtgaag ctacagggtc agctggactt   1140
cagagatttt gattattctg gcacttcctt gaaggccttg tctatacacc aagttgtcag   1200
cgatgtgttc ggttttccgc aaagttatat ctatgaaatc ttttcgaata tgaacatcaa   1260
aaatttcaca gtgtctggta cacgcatggt ccacatgctt tgcccatcca aaattagccc   1320
gttcctgcat ttggattttt ccaataatct cttaacagac acggttttg aaaattgtgg   1380
gcaccttact gagttggaga cacttatttt acaaatgaat caattaaaag aactttcaaa   1440
aatagctgaa atgactacac agatgaagtc tctgcaacaa ttggatatta gccagaattc   1500
tgtaagctat gatgaaaaga aaggagactg ttcttggact aaaagtttat taagtttaaa   1560
tatgtcttca aatatactta ctgacactat tttcagatgt ttacctccca ggatcaaggt   1620
acttgatctt cacagcaata aaataaagag cattcctaaa caagtcgtaa aactggaagc   1680
tttgcaagaa ctcaatgttg ctttcaattc tttaactgac cttcctggat gtggcagctt   1740
tagcagcctt tctgtattga tcattgatca caattcagtt tcccacccat cggctgattt   1800
cttccagagc tgccagaaga tgaggtcaat aaaagcaggg gacaatccat tccaatgtac   1860
ctgtgagcta ggagaatttg tcaaaaatat agaccaagta tcaagtgaag tgttagaggg   1920
ctggcctgat tcttataagt gtgactaccc ggaaagttat agaggaaccc tactaaagga   1980
cttcacatg tctgaattat cctgcaacat aactctgctg atcgtcacca tcgttgccac   2040
catgctggtt ttggctgtga ctgtgacctc cctctgcagc tacttggatc tgccctggta   2100
tctcaggatg gtgtgccagt ggacccagac ccggcgcagg gccaggaaca tacccttaga   2160
agaactccaa agaaatctcc agtttcatgc atttatttca tatagtgggc acgattcttt   2220
ctgggtgaag aatgaattat tgccaaacct agagaagaa ggtatgcaga tttgccttca   2280
tgagagaaac tttgttcctg caagagcat tgtggaaaat atcatcacct gcattgagaa   2340
gagttacaag tccatctttg ttttgtctcc caactttgtc cagagtgaat ggtgccatta   2400
tgaactctac tttgcccatc acaatctctt tcatgaagga tctaatagct taatcctgat   2460
cttgctggaa cccattccgc agtactccat tcctagcagt tatcacaagc tcaaaagtct   2520
catggccagg aggacttatt tggaatggcc caaggaaaag agcaaacgtg gccttttttg   2580
ggctaactta agggcagcca ttaatattaa gctgacagag caagcaaaga aatagattac   2640
```

-continued

```
acatcaagtg aaaaatattc ctcctgttga tattgctgct tttggaagtt ccaacaatga    2700
ctttattttg catcagcata gatgtaaaca caattgtgag tgtatgatgt aggtaaaaat    2760
atataccttc gggtcgcagt tcaccattta tatgtggtat taaaaattaa tgaaatgata    2820
taactttgat ttaaacagtt ctgacacata aaaaaaaaaa aaaaaaa                  2867
```

```
<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
ggcacgattc tttctgggtg aagaa                                            25

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 27
aaggtatgca gatttgcctt catga                                            25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28
aatggtgcca ttatgaactc tactt                                            25

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 29
atagcttaat cctgatcttg ctgga                                            25

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 30
gtactccatt cctagcagtt atcac                                            25

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 31
aagctcaaaa gtctcatggc cagga                                            25
```

```
<210> SEQ ID NO 32
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 32
ggaggactta tttggaatgg cccaa                                              25

<210> SEQ ID NO 33
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 33
gagcaaacgt ggccttttt gggct                                               25

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 34
ttgggctaac ttaagggcag ccatt                                              25

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 35
tattcctcct gttgatattg ctgct                                              25

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 36
gactttattt tgcatcagca tagat                                              25

<210> SEQ ID NO 37
<211> LENGTH: 3417
<212> TYPE: DNA
<213> ORGANISM: Homo sapiens
<220> FEATURE:
<221> NAME/KEY: misc_feature
<222> LOCATION: (220)..(2574)
<223> OTHER INFORMATION: TLR-2 Coding Sequence

<400> SEQUENCE: 37
cggaggcagc gagaaagcgc agccaggcgg ctgctcggcg ttctctcagg tgactgctcg        60
gagttctccc agtgtttggt gttgcaagca ggatccaaag gagacctata gtgactccca       120
ggagctctta gtgaccaagt gaaggtacct gtggggctca ttgtgccat tgctctttca        180 ctgctttcaa ctggtagttg tgggttgaag cactggacaa tgccacatac tttgtggatg       240
```

```
gtgtgggtct tggggggtcat catcagcctc tccaaggaag aatcctccaa tcaggcttct    300
ctgtcttgtg accgcaatgg tatctgcaag ggcagctcag gatctttaaa ctccattccc    360
tcagggctca cagaagctgt aaaaagcctt gacctgtcca acaacaggat cacctacatt    420
agcaacagtg acctacagag gtgtgtgaac ctccaggctc tggtgctgac atccaatgga    480
attaacacaa tagaggaaga ttcttttttct tccctgggca gtcttgaaca tttagactta    540
tcctataatt acttatctaa tttatcgtct tcctggttca agccccttc ttctttaaca    600 ttcttaaact tactgggaaa tccttacaaa accctagggg aaacatctct ttttctcat    660 ctcacaaaat tgcaaatcct gagagtggga aatatggaca ccttcactaa gattcaaaga    720
aaagattttg ctggacttac cttccttgag gaacttgaga ttgatgcttc agatctacag    780
agctatgagc caaaaagttt gaagtcaatt cagaatgtaa gtcatctgat ccttcatatg    840
aagcagcata ttttactgct ggagattttt gtagatgtta caagttccgt ggaatgtttg    900
gaactgcgag atactgattt ggacactttc cattttttcag aactatccac tggtgaaaca    960
aattcattga ttaaaaagtt tacatttaga aatgtgaaaa tcaccgatga agtttgttt   1020 caggttatga aacttttgaa tcagatttct ggattgttag aattagagtt tgatgactgt   1080
acccttaatg gagttggtaa ttttagagca tctgataatg acagagttat agatccaggt   1140
aaagtggaaa cgttaacaat ccggaggctg catattccaa ggttttactt attttatgat   1200
ctgagcactt tatattcact tacagaaaga gttaaaagaa tcacagtaga aacagtaaa   1260 gttttctgg ttccttgttt actttcacaa catttaaaat cattagaata cttggatctc   1320
agtgaaaatt tgatggttga agaatacttg aaaaattcag cctgtgagga tgcctggccc   1380
tctctacaaa ctttaatttt aaggcaaaat catttggcat cattggaaaa aaccggagag   1440
actttgctca ctctgaaaaa cttgactaac attgatatca gtaagaatag ttttcattct   1500
atgcctgaaa cttgtcagtg ccagaaaag atgaaatatt tgaacttatc cagcacacga   1560
atacacagtg taacaggctg cattcccaag acactggaaa ttttagatgt tagcaacaac   1620
aatctcaatt tattttcttt gaatttgccg caactcaaag aactttatat ttccagaaat   1680
aagttgatga ctctaccaga tgcctccctc ttacccatgt tactagtatt gaaaatcagt   1740
aggaatgcaa taactacgtt ttctaaggag caacttgact catttcacac actgaagact   1800
ttggaagctg tggcaataa cttcatttgc tcctgtgaat tcctctcctt cactcaggag   1860
cagcaagcac tggccaaagt cttgattgat tggccagcaa attacctgtg tgactctcca   1920
tcccatgtgc gtggccagca ggttcaggat gtccgcctct cggtgtcgga atgtcacagg   1980
acagcactgg tgtctggcat gtgctgtgct ctgttcctgc tgatcctgct cacggggtc   2040 ctgtgccacc gttccatgg cctgtggtat atgaaaatga tgtgggcctg gctccaggcc   2100
aaaaggaagc ccaggaaagc tcccagcagg aacatctgct atgatgcatt tgtttcttac   2160
agtgagcggg atgcctactg ggtggagaac cttatggtcc aggagctgga gaacttcaat   2220 cccccccttca agttgtgtct tcataagcgg gacttcattc ctggcaagtg gatcattgac   2280
aatatcattg actccattga aaagagccac aaaactgtct ttgtgctttc tgaaaacttt   2340
gtgaagagtg agtggtgcaa gtatgaactg gacttctccc atttccgtct ttttgatgag   2400
aacaatgatg ctgccattct cattcttctg gagcccattg agaaaaaagc cattcccag   2460 cgcttctgca agctgcggaa gataatgaac accaagacct acctggagtg gcccatggac   2520
gaggctcagc gggaaggatt tggggtaaat ctgagagctg cgataaagtc ctaggttccc   2580
atatttaaga ccagtctttg tctagttggg atctttatgt cactagttat agttaagttc   2640
```

```
attcagacat aattatataa aaactacgtg gatgtaccgt catttgagga cttgcttact    2700
aaaactacaa aacttcaaat tttgtctggg gtgctgtttt ataaacatat gccagattta    2760
aaaattggtt tttggttttt cttttttcta tgagataacc atgatcataa gtctattact    2820
gatatctgaa tatagtccct tggtatccaa gggaattggt tgcaggatcc tcgtggatat    2880
caaaattcat agatgatcaa gtcccttata agagtggcat agtatttgca tataacctgt    2940
gtacattctc ctgtatactt taaatcatct ctagattact tatgataccc aatacaatgt    3000
aaatactatg taaatagttg tactgtcttt ttatttatat tattattgtt attttttatt    3060
ttcaaaattt ttaaaacata cttttgatcc acagttggtt gacttcatgg atgcagaacc    3120
catggatata gagggccaac tgtaatctgt agcaactggc ttagttcatt aggaaacagc    3180
acaaatgaac ttaagattct caatgactgt gtcattcttt cttcctgcta agagactcct    3240
ctgtggccac aaaaggcatt ctctgtccta cctagctgtc acttctctgt gcagctgatc    3300
tcaagagcaa caaggcaaag tatttggggc actccccaaa acttgttgct attcctagaa    3360
aaaagtgctg tgtatttcct attaaacttt acaggatgag aaaaaaaaaa aaaaaaa     3417
```

<210> SEQ ID NO 38
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 38
gtttcttaca gtgagcggga tgcct                                           25

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 39
gagaacctta tggtccagga gctgg                                           25

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 40
ataagcggga cttcattcct ggcaa                                           25

<210> SEQ ID NO 41
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 41
gtatgaactg gacttctccc atttc                                           25

<210> SEQ ID NO 42
<211> LENGTH: 25
<212> TYPE: DNA
<213> ORGANISM: Artificial Sequence
<220> FEATURE:

<223> OTHER INFORMATION: Synthetic oligonucleotide

<400> SEQUENCE: 42
ctcccatttc cgtcttttg aagag                                           25

<210> SEQ ID NO 43
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 43
aatgatgctg ccattctcat tcttc                                          25

<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 44
agcgcttctg caagctgcgg aagat                                          25

<210> SEQ ID NO 45
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 45
acaccaagac ctacctggag tggcc                                          25

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 46
tggagtggcc catggacgag gctca                                          25

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 47
agctgcgata aagtcctagg ttccc                                          25

<210> SEQ ID NO 48
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 48
gaccagtctt tgtctagttg ggatc                                          25

<210> SEQ ID NO 49

<211> LENGTH: 1702
<212> TYPE: DNA
<213> ORGANISM: Homo sapiens
<220> FEATURE:
<221> NAME/KEY: misc_feature
<222> LOCATION: (82)..(681)
<223> OTHER INFORMATION: CD69 Coding Sequence

<400> SEQUENCE: 49

```
agactcaaca agagctccag caaagacttt cactgtagct tgacttgacc tgagattaac      60
tagggaatct tgagaataaa gatgagctct gaaaattgtt tcgtagcaga aacagctct     120
ttgcatccgg agagtggaca agaaaatgat gccaccagtc cccatttctc aacacgtcat    180
gaagggtcct tccaagttcc tgtcctgtgt gctgtaatga atgtggtctt catcaccatt    240
ttaatcatag ctctcattgc cttatcagtg ggccaataca attgtccagg ccaatacaca    300
ttctcaatgc catcagacag ccatgtttct tcatgctctg aggactgggt tggctaccag    360
aggaaatgct actttatttc tactgtgaag aggagctgga cttcagccca aaatgcttgt    420
tctgaacatg gtgctactct tgctgtcatt gattctgaaa aggacatgaa ctttctaaaa    480
cgatacgcag gtagagagga acactgggtt ggactgaaaa aggaacctgg tcacccatgg    540
aagtggtcaa atggcaaaga atttaacaac tggttcaacg ttacagggtc tgacaagtgt    600
gtttttctga aaaacacaga ggtcagcagc atggaatgtg agaagaattt atactggata    660
tgtaacaaac cttacaaata taaggaaac atgttcactt attgactatt atagaatgga    720
actcaaggaa atctgtgtca gtggatgctg ctctgtggtc cgaagtcttc catagagact    780
ttgtgaaaaa aaatttttata gtgtcttggg aatttttcttc caaacagaac tatggaaaaa    840
aaggaagaaa ttccaggaaa atctgcactg tgggctttta ttgccatgag ctagaagcat    900
cacaggttga ccaataacca tgcccaagaa tgagaagaat gactatgcaa cctttggatg    960
cactttatat tattttgaat ccagaaataa tgaaataact aggcgtggac ttactattta   1020
ttgctgaatg actaccaaca gtgagagccc ttcatgcatt tgcactactg gaaggagtta   1080
gatgttggta ctagatactg aatgtaaaca aaggaattat ggctggtaac ataggttttt   1140
agtctaattg aatcccttaa actcagggag catttataaa tggacaaatg cttatgaaac   1200
taagatttgt aatatttctc tctttttaga gaaatttgcc aatttacttt gttattttc   1260
cccaaaaaga atgggatgat cgtgtattta ttttttact tcctcagctg tagacaggtc    1320
cttttcgatg gtacatattt ctttgccttt ataatctttt atacagtgtc ttacagagaa   1380
aagacataag caaagactat gaggaatatt tgcaagacat agaatagtgt tggaaaatgt   1440
gcaatatgtg atgtggcaaa tctctattag gaaatattct gtaatcttca gacctagaat   1500
aatactagtc ttataatagg tttgtgactt tcctaaatca attctattac gtgcaatact   1560
tcaatacttc atttaaaata ttttttatgtg caataaaatg tatttgtttg tattttgtgt   1620
tcagtacaat tataagctgt ttttatatat gtgaaataaa agtagaataa acacaaaaaa   1680
aaaaaaaaaa aaaaaaaaaa aa                                            1702
```

<210> SEQ ID NO 50
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 50

```
tagtctaatt gaatccctta aactc                                           25
```

```
<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 51
atgggatgat cgtgtattta ttttt                                       25

<210> SEQ ID NO 52
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 52
tttttacttt cctcagctgt agaca                                       25

<210> SEQ ID NO 53
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 53
acttcctcag ctgtagacag gtcct                                       25

<210> SEQ ID NO 54
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 54
gacaggtcct tttcgatggt acata                                       25

<210> SEQ ID NO 55
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 55
tggtacatat ttctttgcct ttata                                       25

<210> SEQ ID NO 56
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 56
tataatcttt tatacagtgt cttac                                       25

<210> SEQ ID NO 57
<211> LENGTH: 25
<212> TYPE: DNA
<213> ORGANISM: Artificial Sequence
<220> FEATURE:
<223> OTHER INFORMATION: Synthetic oligonucleotide
```

```
<400> SEQUENCE: 57
gtgatgtggc aaatctctat tagga                                    25

<210> SEQ ID NO 58
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 58
atattctgta atcttcagac ctaga                                    25

<210> SEQ ID NO 59
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 59
aggtttgtga ctttcctaaa tcaat                                    25

<210> SEQ ID NO 60
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 60
tacgtgcaat acttcaatac ttcat                                    25

<210> SEQ ID NO 61
<211> LENGTH: 523
<212> TYPE: DNA
<213> ORGANISM: Homo sapiens
<220> FEATURE:
<221> NAME/KEY: misc_feature
<222> LOCATION: (99)..(284)
<223> OTHER INFORMATION: CDW52 Coding Sequence

<400> SEQUENCE: 61
ctcctggttc aaaagcagct aaaccaaaag aagcctccag acagccctga gatcacctaa     60
aaagctgcta ccaagacagc cacgaagatc ctaccaaaat gaagcgcttc ctcttcctcc    120
tactcaccat cagcctcctg gttatggtac agatacaaac tggactctca ggacaaaacg    180
acaccagcca aaccagcagc ccctcagcat ccagcaacat aagcggaggc atttcccttt    240
tcttcgtggc caatgccata tccacctct tctgcttcag ttgaggtgac acgtctcagc    300
cttagccctg tgcccctga aacagctgcc accatcactc gcaagagaat ccctccatc     360 tttgggaggg gttgatgcca gacatcacca ggttgtagaa gttgacaggc agtgccatgg    420
gggcaacagc caaaatagggg ggtaatgat gtaggggcca agcagtgccc agctgggggt    480
caataaagtt acccttgtac ttgcaaaaaa aaaaaaaaa aaa                       523

<210> SEQ ID NO 62
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 62
```

-continued taatcggctc actataggaa tttgc                                    25

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 63
aagcagctaa accaaaagaa gcctc                                    25

<210> SEQ ID NO 64
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 64
cagatacaaa ctggactctc aggac                                    25

<210> SEQ ID NO 65
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 65
caaactggac tctcaggaca aaacg                                    25

<210> SEQ ID NO 66
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 66
tcaggacaaa acgacaccag ccaaa                                    25

<210> SEQ ID NO 67
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 67 ttcctttttct tcgtggccaa tgcca                                   25

<210> SEQ ID NO 68
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 68
ttcttcgtgg ccaatgccat aatcc                                    25

<210> SEQ ID NO 69
<211> LENGTH: 25
<212> TYPE: DNA
<213> ORGANISM: Artificial Sequence
<220> FEATURE:

<223> OTHER INFORMATION: Synthetic oligonucleotide

<400> SEQUENCE: 69
ttctgcttca gttgaggtga cacgt                                25

<210> SEQ ID NO 70
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 70
ttcagttgag gtgacacgtc tcagc                                25

<210> SEQ ID NO 71
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 71
gtgacacgtc tcagccttag ccctg                                25

<210> SEQ ID NO 72
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 72
ggttgatgcc agacatcacc aggtt                                25

<210> SEQ ID NO 73
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 73
atcaccaggt tgtagaagtt gacag                                25

<210> SEQ ID NO 74
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 74
caccaggttg tagaagttga caggc                                25

<210> SEQ ID NO 75
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 75
atgtaggggc caagcagtgc ccagc                                25

<210> SEQ ID NO 76

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 76
tgtaggggcc aagcagtgcc cagct                                         25

<210> SEQ ID NO 77
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 77
gtcaataaag ttacccttgt acttg                                         25

<210> SEQ ID NO 78
<211> LENGTH: 1310
<212> TYPE: DNA
<213> ORGANISM: Homo sapiens
<220> FEATURE:
<221> NAME/KEY: misc_feature
<222> LOCATION: (103)..(1110)
<223> OTHER INFORMATION: Gapdh Coding Sequence

<400> SEQUENCE: 78
aaattgagcc cgcagcctcc cgcttcgctc tctgctcctc ctgttcgaca gtcagccgca     60
tcttcttttg cgtcgccagc cgagccacat cgctcagaca ccatggggaa ggtgaaggtc    120
ggagtcaacg gatttggtcg tattgggcgc ctggtcacca gggctgcttt taactctggt    180
aaagtggata ttgttgccat caatgacccc ttcattgacc tcaactacat ggtttacatg    240
ttccaatatg attccaccca tggcaaattc catggcaccg tcaaggctga gaacgggaag    300
cttgtcatca atggaaatcc catcaccatc ttccaggagc gagatccctc caaaatcaag    360
tggggcgatg ctggcgctga gtacgtcgtg gagtccactg gcgtcttcac caccatggag    420
aaggctgggg ctcatttgca gggggagcc aaaagggtca tcatctctgc ccctctgct    480 gatgccccca tgttcgtcat gggtgtgaac catgagaagt atgacaacag cctcaagatc    540
atcagcaatg cctcctgcac caccaactgc ttagcacccc tggccaaggt catccatgac    600
aactttggta tcgtggaagg actcatgacc acagtccatg ccatcactgc cacccagaag    660 actgtgatg ccctccgg gaaactgtgg cgtgatggcc gcggggctct ccagaacatc    720
atccctgcct ctactggcgc tgccaaggct gtgggcaagg tcatccctga gctgaacggg    780
aagctcactg gcatggcctt ccgtgtcccc actgccaacg tgtcagtggt ggacctgacc    840
tgccgtctag aaaaacctgc caaatatgat gacatcaaga aggtggtgaa gcaggcgtcg    900 gagggcccc tcaagggcat cctgggctac actgagcacc aggtggtctc ctctgacttc    960
aacagcgaca cccactcctc cacctttgac gctgggctg gcattgccct caacgaccac   1020
tttgtcaagc tcatttcctg gtatgacaac gaatttggct acagcaacag ggtggtggac   1080
ctcatggccc acatggcctc caaggagtaa gacccctgga ccaccagccc cagcaagagc   1140
acaagaggaa gagagagacc ctcactgctg gggagtccct gccacactca gtcccccacc   1200
acactgaatc tcccctcctc acagttgcca tgtagacccc ttgaagaggg gaggggccta   1260
gggagccgca ccttgtcatg taccatcaat aaagtaccct gtgctcaacc                 1310

<210> SEQ ID NO 79
```

```
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 79
cctctgactt caacagcgac accca                                          25

<210> SEQ ID NO 80
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 80
gggctggcat tgccctcaac gacca                                          25

<210> SEQ ID NO 81
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 81
ccctcaacga ccactttgtc aagct                                          25

<210> SEQ ID NO 82
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 82
accactttgt caagctcatt tcctg                                          25

<210> SEQ ID NO 83
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 83
ttgtcaagct catttcctgg tatga                                          25

<210> SEQ ID NO 84
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 84
tcatttcctg gtatgacaac gaatt                                          25

<210> SEQ ID NO 85
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 85
```

-continued acaacgaatt tggctacagc aacag                                         25

<210> SEQ ID NO 86
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 86
gggtggtgga cctcatggcc cacat                                         25

<210> SEQ ID NO 87
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 87
tcatggccca catggcctcc aagga                                         25

<210> SEQ ID NO 88
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 88
acatggcctc caaggagtaa gaccc                                         25

<210> SEQ ID NO 89
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 89
aggagtaaga cccctggacc accag                                         25

<210> SEQ ID NO 90
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 90
gccccagcaa gagcacaaga ggaag                                         25

<210> SEQ ID NO 91
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 91
gagagagacc ctcactgctg gggag                                         25

<210> SEQ ID NO 92
<211> LENGTH: 25
<212> TYPE: DNA
<213> ORGANISM: Artificial Sequence
<220> FEATURE:

```
<223> OTHER INFORMATION: Synthetic oligonucleotide

<400> SEQUENCE: 92
cctcactgct ggggagtccc tgcca                                    25

<210> SEQ ID NO 93
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 93
cctcctcaca gttgccatgt agacc                                    25

<210> SEQ ID NO 94
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 94
agttgccatg tagacccctt gaaga                                    25

<210> SEQ ID NO 95
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 95
catgtagacc ccttgaagag gggag                                    25

<210> SEQ ID NO 96
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 96
tagggagccg caccttgtca tgtac                                    25

<210> SEQ ID NO 97
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 97
gccgcacctt gtcatgtacc atcaa                                    25

<210> SEQ ID NO 98
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 98
tgtcatgtac catcaataaa gtacc                                    25

<210> SEQ ID NO 99
```

<211> LENGTH: 1793
<212> TYPE: DNA
<213> ORGANISM: Homo sapiens
<220> FEATURE:
<221> NAME/KEY: misc_feature
<222> LOCATION: (74)..(1201)
<223> OTHER INFORMATION: B-actin Coding Sequence

<400> SEQUENCE: 99

| | | | | | |
|---|---|---|---|---|---|
| cgcgtccgcc | ccgcgagcac | agagcctcgc | ctttgccgat | ccgccgcccg | tccacacccg | 60 |
| ccgccagctc | accatggatg | atgatatcgc | cgcgctcgtc | gtcgacaacg | gctccggcat | 120 |
| gtgcaaggcc | ggcttcgcgg | gcgacgatgc | ccccgggcc | gtcttcccct | ccatcgtggg | 180 |
| gcgccccagg | caccagggcg | tgatggtggg | catgggtcag | aaggattcct | atgtgggcga | 240 |
| cgaggcccag | agcaagagag | gcatcctcac | cctgaagtac | cccatcgagc | acggcatcgt | 300 |
| caccaactgg | gacgacatgg | agaaaatctg | gcaccacacc | ttctacaatg | agctgcgtgt | 360 |
| ggctcccgag | gagcaccccg | tgctgctgac | cgaggccccc | ctgaacccca | aggccaaccg | 420 |
| cgagaagatg | acccagatca | tgtttgagac | cttcaacacc | ccagccatgt | acgttgctat | 480 |
| ccaggctgtg | ctatccctgt | acgcctctgg | ccgtaccact | ggcatcgtga | tggactccgg | 540 |
| tgacggggtc | acccacactg | tgcccatcta | cgaggggtat | gccctccccc | atgccatcct | 600 |
| gcgtctggac | ctggctggcc | gggacctgac | tgactacctc | atgaagatcc | tcaccgagcg | 660 |
| cggctacagc | ttcaccacca | cggccgagcg | ggaaatcgtg | cgtgacatta | aggagaagct | 720 |
| gtgctacgtc | gccctggact | tcgagcaaga | gatggccacg | gctgcttcca | gctcctccct | 780 |
| ggagaagagc | tacgagctgc | ctgacggcca | ggtcatcacc | attggcaatg | agcggttccg | 840 |
| ctgccctgag | gcactcttcc | agccttcctt | cctgggcatg | gagtcctgtg | gcatccacga | 900 |
| aactaccttc | aactccatca | tgaagtgtga | cgtggacatc | cgcaaagacc | tgtacgccaa | 960 |
| cacagtgctg | tctggcggca | ccaccatgta | ccctggcatt | gccgacagga | tgcagaagga | 1020 |
| gatcactgcc | ctggcaccca | gcacaatgaa | gatcaagatc | attgctcctc | ctgagcgcaa | 1080 |
| gtactccgtg | tggatcggcg | gctccatcct | ggcctcgctg | tccaccttcc | agcagatgtg | 1140 |
| gatcagcaag | caggagtatg | acgagtccgg | cccctccatc | gtccaccgca | aatgcttcta | 1200 |
| ggcggactat | gacttagttg | cgttacaccc | tttcttgaca | aaacctaact | tgcgcagaaa | 1260 |
| acaagatgag | attggcatgg | ctttatttgt | tttttttgtt | ttgttttggt | ttttttttt | 1320 |
| tttttggctt | gactcaggat | ttaaaaactg | gaacggtgaa | ggtgacagca | gtcggttgga | 1380 |
| gcgagcatcc | cccaaagttc | acaatgtggc | cgaggacttt | gattgcacat | tgttgttttt | 1440 |
| ttaatagtca | ttccaaatat | gagatgcatt | gttacaggaa | gtcccttgcc | atcctaaaag | 1500 |
| ccacccact | tctctctaag | gagaatggcc | cagtcctctc | ccaagtccac | acaggggagg | 1560 |
| tgatagcatt | gctttcgtgt | aaattatgta | atgcaaaatt | tttttaatct | tcgccttaat | 1620 |
| actttttat | tttgttttat | tttgaatgat | gagccttcgt | gccccccctt | ccccttttt | 1680 |
| gtcccccaac | ttgagatgta | tgaaggcttt | tggtctccct | gggagtgggt | ggaggcagcc | 1740 |
| agggcttacc | tgtacactga | cttgagacca | gttgaataaa | agtgcacacc | tta | 1793 |

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 100
tcttgacaaa acctaacttg cgcag 25

<210> SEQ ID NO 101
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 101
atgagattgg catggcttta tttgt 25

<210> SEQ ID NO 102
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 102
gcagtcggtt ggagcgagca tcccc 25

<210> SEQ ID NO 103
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 103
ccaaagttca caatgtggcc gagga 25

<210> SEQ ID NO 104
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 104
aagttcacaa tgtggccgag gactt 25

<210> SEQ ID NO 105
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 105
atgtggccga ggactttgat tgcac 25

<210> SEQ ID NO 106
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 106
ccgaggactt tgattgcaca ttgtt 25

<210> SEQ ID NO 107
<211> LENGTH: 25
<212> TYPE: DNA
<213> ORGANISM: Artificial Sequence
<220> FEATURE:

<223> OTHER INFORMATION: Synthetic oligonucleotide

<400> SEQUENCE: 107
tttaatagtc attccaaata tgaga    25

<210> SEQ ID NO 108
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 108
agtcattcca aatatgagat gcatt    25

<210> SEQ ID NO 109
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 109
tgttacagga agtcccttgc catcc    25

<210> SEQ ID NO 110
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 110
tacaggaagt cccttgccat cctaa    25

<210> SEQ ID NO 111
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 111
tcccttgcca tcctaaaagc caccc    25

<210> SEQ ID NO 112
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 112
cttctctcta aggagaatgg cccag    25

<210> SEQ ID NO 113
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 113
gaggtgatag cattgctttc gtgta    25

<210> SEQ ID NO 114

```
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 114
tattttgaat gatgagcctt cgtgc                                  25

<210> SEQ ID NO 115
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 115
tttgaatgat gagccttcgt gcccc                                  25

<210> SEQ ID NO 116
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 116
gtatgaaggc ttttggtctc cctgg                                  25

<210> SEQ ID NO 117
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 117
ggtggaggca gccagggctt acctg                                  25

<210> SEQ ID NO 118
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 118
cagggcttac ctgtacactg acttg                                  25

<210> SEQ ID NO 119
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 119
ttacctgtac actgacttga gacca                                  25

<210> SEQ ID NO 120
<211> LENGTH: 1816
<212> TYPE: DNA
<213> ORGANISM: Homo sapiens
<220> FEATURE:
<221> NAME/KEY: misc_feature
<222> LOCATION: (40)..(825)
<223> OTHER INFORMATION: CD40L Coding Sequence
```

<400> SEQUENCE: 120

```
cttctctgcc agaagatacc atttcaactt taacacagca tgatcgaaac atacaaccaa      60
acttctcccc gatctgcggc cactggactg cccatcagca tgaaaatttt tatgtattta     120
cttactgttt ttcttatcac ccagatgatt gggtcagcac ttttttgctgt gtatcttcat    180
agaaggttgg acaagataga agatgaaagg aatcttcatg aagattttgt attcatgaaa    240
acgatacaga gatgcaacac aggagaaaga tccttatcct tactgaactg tgaggagatt    300
aaaagccagt ttgaaggctt tgtgaaggat ataatgttaa caaagagga gacgaagaaa     360
gaaaacagct ttgaaatgca aaaggtgat cagaatcctc aaattgcggc acatgtcata    420
agtgaggcca gcagtaaaac aacatctgtg ttacagtggg ctgaaaaagg atactacacc    480
atgagcaaca acttggtaac cctggaaaat gggaaacagc tgaccgttaa agacaagga    540
ctctattata tctatgccca agtcaccttc tgttccaatc gggaagcttc gagtcaagct    600
ccatttatag ccagcctctg cctaaagtcc cccggtagat tcgagagaat cttactcaga    660
gctgcaaata cccacagttc cgccaaacct tgcgggcaac aatccattca cttgggagga    720
gtatttgaat tgcaaccagg tgcttcggtg tttgtcaatg tgactgatcc aagccaagtg    780
agccatggca ctggcttcac gtcctttggc ttactcaaac tctgaacagt gtcaccttgc    840
aggctgtggt ggagctgacg ctgggagtct tcataataca gcacagcggt taagcccacc    900
ccctgttaac tgcctattta taaccctagg atcctcctta tggagaacta tttattatac    960
actccaaggc atgtagaact gtaataagtg aattacaggt cacatgaaac caaaacgggc   1020
cctgctccat aagagcttat atatctgaag cagcaacccc actgatgcag acatccagag   1080
agtcctatga aaagacaagg ccattatgca caggttgaat tctgagtaaa cagcagataa   1140
cttgccaagt tcagttttgt ttcttttgcgt gcagtgtctt tccatggata atgcatttga   1200
tttatcagtg aagatgcaga agggaaatgg ggagcctcag ctcacattca gttatggttg   1260
actctgggtt cctatggcct tgttggaggg ggccaggctc tagaacgtct aacacagtgg   1320
agaaccgaaa ccccccccccc ccccccgcc accctctcgg acagttattc attctctttc   1380
aatctctctc tctccatctc tctctttcag tctctctctc tcaacctctt tcttccaatc   1440
tctcttctc aatctctctg tttcccttttg tcagtctctt ccctccccca gtctctcttc    1500
tcaatccccc tttctaacac acacacacac acacacacac acacacacac acacacacac    1560
acacacacac acacacacac agagtcaggc cgttgctagt cagttctctt ctttccaccc    1620
tgtccctatc tctaccacta tagatgaggg tgaggagtag ggagtgcagc cctgagcctg    1680
cccactcctc attacgaaat gactgtattt aaaggaaatc tattgtatct acctgcagtc    1740
tccattgttt ccagagtgaa cttgtaatta tcttgttatt tatttttga ataataaaga    1800
cctcttaaca ttaaaa                                                   1816
```

<210> SEQ ID NO 121
<211> LENGTH: 261
<212> TYPE: PRT
<213> ORGANISM: Homo sapiens

<400> SEQUENCE: 121

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45
```

-continued

```
Arg Leu Asp Lys Ile Glu Asp Glu Arg Asn Leu His Glu Asp Phe Val
        50              55              60

Phe Met Lys Thr Ile Gln Arg Cys Asn Thr Gly Glu Arg Ser Leu Ser
65              70              75              80

Leu Leu Asn Cys Glu Glu Ile Lys Ser Gln Phe Glu Gly Phe Val Lys
            85              90              95

Asp Ile Met Leu Asn Lys Glu Glu Thr Lys Lys Glu Asn Ser Phe Glu
            100             105             110

Met Gln Lys Gly Asp Gln Asn Pro Gln Ile Ala Ala His Val Ile Ser
        115             120             125

Glu Ala Ser Ser Lys Thr Thr Ser Val Leu Gln Trp Ala Glu Lys Gly
    130             135             140

Tyr Tyr Thr Met Ser Asn Asn Leu Val Thr Leu Glu Asn Gly Lys Gln
145             150             155             160

Leu Thr Val Lys Arg Gln Gly Leu Tyr Tyr Ile Tyr Ala Gln Val Thr
                165             170             175

Phe Cys Ser Asn Arg Glu Ala Ser Ser Gln Ala Pro Phe Ile Ala Ser
            180             185             190

Leu Cys Leu Lys Ser Pro Gly Arg Phe Glu Arg Ile Leu Leu Arg Ala
        195             200             205

Ala Asn Thr His Ser Ser Ala Lys Pro Cys Gly Gln Gln Ser Ile His
    210             215             220

Leu Gly Gly Val Phe Glu Leu Gln Pro Gly Ala Ser Val Phe Val Asn
225             230             235             240

Val Thr Asp Pro Ser Gln Val Ser His Gly Thr Gly Phe Thr Ser Phe
            245             250             255

Gly Leu Leu Lys Leu
            260
```